US012570741B2

(12) United States Patent
Arboleda-Velasquez

(10) Patent No.: US 12,570,741 B2
(45) Date of Patent: Mar. 10, 2026

(54) NOTCH3 AGONIST COMPOSITIONS AND METHODS FOR TREATING SMALL VESSEL DISEASES

(71) Applicant: Massachusetts Eye and Ear Infirmary, Boston, MA (US)

(72) Inventor: Joseph F. Arboleda-Velasquez, Newton, MA (US)

(73) Assignee: Massachusetts Eye and Ear Infirmary, Boston, MA (US)

( * ) Notice: Subject to any disclaimer, the term of this patent is extended or adjusted under 35 U.S.C. 154(b) by 347 days.

(21) Appl. No.: 17/823,824

(22) Filed: Aug. 31, 2022

(65) Prior Publication Data

US 2023/0107235 A1 Apr. 6, 2023

Related U.S. Application Data

(63) Continuation of application No. 16/499,225, filed as application No. PCT/US2018/024397 on Mar. 26, 2018, now Pat. No. 11,453,718.

(60) Provisional application No. 62/477,289, filed on Mar. 27, 2017.

(51) Int. Cl.

| | |
|---|---|
| ***C07K 16/28*** | (2006.01) |
| ***A61K 38/00*** | (2006.01) |
| ***C07K 14/705*** | (2006.01) |
| ***C12Q 1/6883*** | (2018.01) |

(52) U.S. Cl.

CPC ............ *C07K 16/28* (2013.01); *C07K 14/705* (2013.01); *C12Q 1/6883* (2013.01); *A61K 38/00* (2013.01); *C07K 2317/75* (2013.01)

(58) Field of Classification Search

None

See application file for complete search history.

(56) References Cited

U.S. PATENT DOCUMENTS

| | | | |
|---|---|---|---|
| 7,915,390 | B2 | 3/2011 | Li et al. |
| 7,935,791 | B2 | 5/2011 | Fung et al. |
| 8,187,839 | B2 | 5/2012 | Li et al. |
| 8,226,943 | B2 | 7/2012 | Gurney et al. |
| 2002/0182733 | A1 | 12/2002 | Naldini et al. |
| 2003/0186290 | A1 | 10/2003 | Tournier-Lasserve et al. |
| 2008/0131908 | A1 | 6/2008 | Li et al. |
| 2011/0223183 | A1 | 9/2011 | Kitajewski et al. |
| 2012/0100536 | A1 | 4/2012 | Tsuji et al. |
| 2013/0129743 | A1 | 5/2013 | Wu et al. |
| 2013/0323266 | A1 | 12/2013 | Hoey et al. |
| 2013/0324468 | A1 | 12/2013 | Cipolla et al. |
| 2014/0045198 | A1 | 2/2014 | Montaner Villalonga et al. |
| 2014/0323413 | A1 | 10/2014 | Hageman et al. |
| 2015/0119278 | A1 | 4/2015 | Goetzl |
| 2015/0268251 | A1 | 9/2015 | Zaugg et al. |
| 2016/0115453 | A1 | 4/2016 | Mummery et al. |
| 2016/0185852 | A1 | 6/2016 | Okamura et al. |
| 2016/0305959 | A1 | 10/2016 | Levy et al. |
| 2017/0023576 | A1 | 1/2017 | Cancilla |
| 2019/0350961 | A1 | 11/2019 | Arboleda-Velasquez et al. |
| 2020/0103419 | A1 | 4/2020 | Arboleda-Velasquez et al. |
| 2020/0375899 | A1 | 12/2020 | Kim et al. |
| 2020/0377888 | A1 | 12/2020 | Kim et al. |
| 2023/0190764 | A1 | 6/2023 | Arboleda-Velasquez et al. |
| 2023/0190959 | A1 | 6/2023 | Arboleda-Velasquez |
| 2023/0310446 | A1 | 10/2023 | Kim et al. |

FOREIGN PATENT DOCUMENTS

| | | |
|---|---|---|
| WO | WO 2016046053 | 3/2016 |

OTHER PUBLICATIONS

Benjamin and Hill, "Tonicity of human tear fluid sampled from the cul-de-sac," British Journal of Ophthalmology, Aug. 1989, 73(8):624-627.

GenBank Accession No. BC063833.1, "*Homo sapiens* collagen, type XVIII, alpha 1, mRNA (cDNA clone MGC:74745 IMAGE:6181818), complete cds," dated Aug. 4, 2006, 3 pages.

Altobelli et al., "HtrA1: Its future potential as a novel biomarker for cancer," Oncol Rep, 2015, 34(2):555-66.

Arboleda-Velasquez et al., "C455R notch3 mutation in a Colombian CADASIL kindred with early onset of stroke," Neurology, 2002, 59(2):277-279.

Arboleda-Velasquez et al., "CADASIL mutations impair Notch3 glycosylation by Fringe," Hum Mol Genet., 2005, 14(12):1631-1639.

Arboleda-Velasquez et al., "Hypomorphic Notch 3 alleles link Notch signaling to ischemic cerebral small-vessel disease," Proc Natl Acad Sci USA, May 2011, 108(21):E128-E135.

Arboleda-Velasquez et al., "Linking Notch signaling to ischemic stroke," Proc Natl Acad Sci USA, 2008, 105(12):4856-4861.

Arboleda-Velasquez et al., "Notch Signaling Functions in Retinal Pericyte Survival," Invest Ophthalmol Vis Sci., 2014, 55(8):5191-5199.

Bae et al., "Regulation of IGFBP-1 in metabolic diseases," J Lifestyle Med., 2013, 3(2):73-79.

Baudrimont et al., "Autosomal Dominant Leukoencephalopathy and Subcortical Ischemic Stroke. A Clinicopathological study," Stroke, 1993, 24:122-125.

Beaufort et al., "Cerebral small vessel disease-related protease HtrA1 processes latent TGF-β binding protein 1 and facilitates TGF-β signaling," Proc Natl Acad Sci USA, 2014, 111(46):16496-16501.

(Continued)

*Primary Examiner* — Ruixiang Li

(74) *Attorney, Agent, or Firm* — Fish & Richardson P.C.

(57) ABSTRACT

The present subject matter provides, inter alia, compositions, formulations, and methods for inhibiting, treating, and preventing small vessel diseases.

15 Claims, 6 Drawing Sheets

Specification includes a Sequence Listing.

(56) References Cited

OTHER PUBLICATIONS

Brass et al., "Case 12-2009: A 46-Year-Old Man with Migraine, Aphasia, and Hemiparesis and Similarly Affected Family Members," N Engl J Med, 2009, 360(16): 656-1665.
Cade, "Diabetes-Related Microvascular and Macrovascular Diseases in the Physical therapy setting," Phys Ther, 2008, 88(11):1322-1335.
Chabriat et al., "CADASIL," Lancet Neurol., 2009, 8:643-653.
Charidimou, "Book review: 'Cerebral small vessel disease'. What's the big deal about small vessels?," Front Neurol., 2015, 6:175, 2 pages.
Damico et al., "Serum endostatin is a genetically determined predictor of survival in pulmonary arterial hypertension," Am J Respir Crit Care Med, 2015, 191(2):208-218.
Dichgans et al., "Small in-frame deletions and missense mutations in CADASIL: 3D models predict misfolding of Notch3 EGF-like repeat domains," European Journal of Human Genetics, 2000, 8:280-285.
Dichgans et al., "The Phenotypic Spectrum of CADASIL: Clinical Findings in 102 Cases," Annals of Neurology, 1998, 44(5):731-739.
Dotti et al., "A Novel NOTCH3 Frameshift Deletion and Mitochondrial Abnormalities in a Patient With CADASIL," Arch Neurol., 2004, 61(6):942-945.
Erro et al., "Are granular osmiophilic material deposits an epiphenomenon in CADASIL?" Folia Neuropathol., 2015, 53:168-171.
Evans et al., "Cardiovascular comorbidities, inflammation, and cerebral small vessel disease," Cardiovasc Res, Nov. 2021, 117(13):2575-2588.
Fouillade et al., "Activating NOTCH3 Mutation in a Patient with Small-vessel-disease of the Brain," Human Mutation, 2008, 29(3):452, 9 pages.
Funatsu et al., "Outcome of vitreous surgery and the balance between vascular endothelial growth factor and endostatin," Invest Ophthalmol Vis Sci, 2003, 44(3):1042-1047.
Fung et al., "Delta-like 4 induces notch signaling in macrophages: implications for inflammation," Circulation, 2007, 115(23):2948-2956.
Ghosh et al., "Pericytes are involved in the pathogenesis of cerebral autosomal dominant arteriopathy with subcortical infarcts and leukoencephalopathy," Ann Neurol., 2015, 78(6):887-900.
Giau et al., "Genetic factors of cerebral small vessel disease and their potential clinical outcome," Int J Mol Sci, Sep. 2019, 20(17):4298, 27 pages.
Gould et al., "Role of COL4A1 in Small-Vessel Disease and Hemorrhagic Stroke," N Engl J Med, 2006, 354:1489-1496.
Gouya et al., "Association of endostatin with mortality in patients with chronic heart failure," Eur J Clin Invest, 2014, 44(2):125-35.
Hakim, "Silent, but preventable, perils," Nature, 2014, 510:S12.
Haque et al., "Inhibition of Tau Aggregation by a Rosamine Derivative that Blocks Tau Intermolecular Disulfide Cross-Linking", Amyloid, 2014, 21(3):185-190.
Hara et al., "Association of HTRA1 Mutations and Familial Ischemic Cerebral Small-Vessel Disease," N Engl J Med, 2009, 360:1729-1739.
Henshall et al., "Notch3 Is Necessary for Blood Vessel Integrity in the Central Nervous System," Arterioscler Thromb Vasc Biol., 2015, 35(2):409-420.
Iadecola, "The Pathobiology of Vascular Dementia," Neuron, 2013, 80(4):844-866.
Inagaki et al., "Upregulation of HtrA4 in the placentas of patients with severe pre-eclampsia," Placenta, 2012, 33(11):919-926.
International Preliminary Report on Patentability in International Appln. No. PCT/US2018/024394, dated Oct. 1, 2019, 16 pages.
International Preliminary Report on Patentability in International Appln. No. PCT/US2018/024397, dated Oct. 10, 2019, 10 pages.
International Preliminary Report on Patentability in International Appln. No. PCT/US2018/024407, dated Oct. 10, 2019, 12 pages.
International Search Report and Written Opinion in International Appln. No. PCT/US2018/024394, dated Aug. 8, 2018, 22 pages.
International Search Report and Written Opinion in International Appln. No. PCT/US2018/024397, dated Aug. 3, 2018, 14 pages.
International Search Report and Written Opinion in International Appln. No. PCT/US2018/024407, dated Sep. 18, 2018, 17 pages.
Ishiko et al., "Notch3 ectodomain is a major component of granular osmiophilic material (GOM) in CADASIL," Acta Neuropathol, 2006, 112:333-339.
Joutel and Faraci, "Cerebral Small Vessel Disease: Insights and Opportunities From Mouse Models of Collagen IV-Related Small Vessel Disease and Cerebral Autosomal Dominant Arteriopathy With Subcortical Infarcts and Leukoencephalopathy," Stroke, 2014, 45(4):1215-1221.
Joutel et al., "Cerebrovascular dysfunction and microcirculation rarefaction precede white matter lesions in a mouse genetic model of cerebral ischemic small vessel disease," J Clin Invest., 2010, 120(2):433-445.
Joutel et al., "Notch3 mutations in CADASIL, a hereditary adult-onset condition causing stroke and dementia," Nature, 1996, 383:707-710.
Joutel et al., "Pathogenic Mutations Associated with Cerebral Autosomal Dominant Arteriopathy with Subcortical Infarcts and Leukoencephalopathy Differently Affect Jagged1 Binding and Notch3 Activity via the RBP/JK Signaling Pathway," Am J Hum Genet., 2004, 74:338-347.
Joutel et al., "Perturbations of the cerebrovascular matrisome: A convergent mechanism in small vessel disease of the brain?," J Cereb Blood Flow Metab, 2016, 36(1):143-157.
Joutel et al., "Skin biopsy immunostaining with a Notch3 monoclonal antibody for CADASIL diagnosis," Lancet, Dec. 2001, 358(9298):2049-2051.
Joutel et al., "Strong clustering and stereotyped nature of Notch3 mutations in CADASIL patients," Lancet, 1997, 350(9090):1511-1515.
Joutel et al., "The ectodomain of the Notch3 receptor accumulates within the cerebrovasculature of CADASIL patients," J Clin Invest, Mar. 2000, 105(5):597-605.
Kalaria, "Cerebrovascular Disease and Mechanisms of Cognitive Impairment," Stroke, 2012, 43(9):2526-2534.
Klueg and Muskavitch, "Ligand-receptor interactions and trans-endocytosis of Delta, Serrate and Notch: members of the Notch signalling pathway in *Drosophila*," J Cell Sci., 1999, 112(Pt 19):3289-3297.
Kodadek, "Protein microarrays: prospects and problems," Chem Biol., 2001, 8:105-115.
Kofler et al., "Combined deficiency of Notch1 and Notch3 causes pericyte dysfunction, models CADASIL and results in arteriovenous malformations," Sci Rep., 2015, 5:16449, 13 pages.
Kopan, "Notch signaling," Cold Spring Harb Perspect Biol., 2012, 4(10):a011213, 5 pages.
Lafkas et al., "NOTCH3 marks clonogenic mammary luminal progenitor cells in vivo," J Cell Biol., 2013, 203(1):47-56.
Li et al., "The Human Homolog of Rat Jagged1 Expressed by Marrow Stroma Inhibits Differentiation of 32D Cells through Interaction with Notch1," Immunity, 1998, 8:43-55.
Louvi et al., "CADASIL: A Critical Look at a Notch Disease," Dev Neurosci, 2006, 28:5-12.
Louvi et al., "Notch and disease: a growing field," Semin Cell Dev Biol., 2012, 23(4):473-480.
MayoClinic.org [online], "Small vessel disease," available on or before Mar. 29, 2016, via Internet Archive: Wayback Machine URL <http://web.archive.org/web/20160329050842/http://www.mayoclinic.org/diseases-conditions/small-vessel-disease/home/ovc-20198376>, retrieved on Feb. 11, 2021, URL <http://www.mayoclinic.org/diseases-conditions/small-vessel-disease/home/ovc-20198376>, 3 pages.
Meng et al., "Biochemical Characterization and Cellular Effects of CADASIL Mutants of NOTCH3," PLoS ONE, Sep. 2012, 7(9):1-13.
Moccia et al., "Hypomorphic NOTCH3 mutation in an Italian family with CADASIL features," Neurobiol Aging, 2015, 36(1):547.e5-547.e11.

(56) References Cited

OTHER PUBLICATIONS

Monet-Lepretre et al., "Abnormal recruitment of extracellular matrix proteins by excess Notch3ECD: a new pathomechanism in CADASIL," Brain, 2013, 136(6):1830-1845.
Navarro-Sobrino et al., "A large screening of angiogenesis biomarkers and their association with neurological outcome after ischemic stroke," Atherosclerosis, 2011, 216:205-211.
Nickoloff et al., "Jagged-1 mediated activation of notch signaling induces complete maturation of human keratinocytes through NF-κB and PPARγ," Cell Death Different., 2002, 9:842-855.
O'Reilly et al., "Endostatin: An Endogenous Inhibitor of Angiogenesis and Tumor Growth," Cell, 1997, 88(2):277-285.
Pippucci et al., "Homozygous NOTCH3 null mutation and impaired NOTCH3 signaling in recessive early onset arteriopathy and cavitating leukoencephalopathy," EMBO Mol Med., 2015, 7(6):848-858.
Primo et al., "Blood Biomarkers in a Mouse Model of CADASIL," Brain Research, 2016, 1644:118-126.
Rana et al., "Neurofilament Light Chain as an Early and Sensitive Predictor of Long-Term Neurological Outcome in Patients after Cardiac Arrest", International Journal of Cardiology, 2013, 168(2):1322-1327.
Robinson et al., "Retinal Findings in Cerebral Autosomal Dominant Arteriopathy with Subcortical Infarcts and Leukoencephalopathy (CADASIL)," Surv Ophthalmol., 2001, 45:445-448.
Rosenberg et al., "Consensus statement for diagnosis of subcortical small vessel disease," J Cereb Blood Flow Metab., 2015, 36(1):6-25.
Ruchoux and Maurage, "Cerebral autosomal dominant arteriopathy with subcortical infarcts and leukoencephalopathy," Journal of Neuropathology and Experimental Neurology, 1997, 56(9):947-964.
Ruchoux et al., "Systemic vascular smooth muscle cell impairment in cerebral autosomal dominant arteriopathy with subcortical infarcts and leukoencephalopathy," Acta Neuropathol., 1995, 89:500-512.
Rufa et al., "Retinal Nerve Fiber Layer Thinning in CADASIL: An Optical Coherence Tomography and MRI Study ," Cerebrovasc Dis., 2011, 31:77-82.
Rutten et al., "Hypomorphic NOTCH3 alleles do not cause CADASIL in humans," Hum Mutat., 2013, 34(11):1486-1489.
Rutten et al., "The NOTCH3 score: a pre-clinical CADASIL biomarker in a novel human genomic NOTCH3 transgenic mouse model with early progressive vascular NOTCH3 accumulation," Acta Neuropathol Commun., Dec. 2015, 3(1):89, 10 pages.
Rutten et al., "Therapeutic NOTCH3 cysteine correction in CADASIL using exon skipping: in vitro proof of concept," Brain, 2016, 139(4):1123-1135.
Silva et al., "Predictive value of vascular disease biomarkers for digital ulcers in systemic sclerosis patients," Clin Exp Rheumatol, 2015, 33(4 Suppl 91):S127-S130.
Snyder et al., "Vascular Contributions to Cognitive Impairment and Dementia Including Alzheimer's Disease," Alzheimers Dement., 2015, 11(6):710-717.
Tan et al., "New insights into mechanisms of small vessel disease stroke from genetics," Clin Sci, Apr. 2017, 131(7):515-531.
Teoh et al., "Serum HtrA1 is differentially regulated between early-onset and late-onset preeclampsia," Placenta, 2015, 36(9):990-995.
Thompson et al., "Living Beyond Our Physiological Means: Small Vessel Disease of the Brain Is an Expression of a Systemic Failure in Arteriolar Function: A Unifying Hypothesis," Stroke, 2009, 40:e322-e330.
Tikka et al., "Congruence between NOTCH3 mutations and GOM in 131 CADASIL patients," Brain, 2009, 132:933-939.
Tikka et al., "MINI-SYMPOSIUM: Pathology & Genetics of (non-CAA) Cerebral Microvascular Disease, CADASIL and CARASIL," Brain Pathology, 2014, 24(5):525-544.
Velasquez et al., "Hypomorphic Notch 3 alleles link Notch signaling to ischemic cerebral small-vessel disease," Proc Natl Acad Sci USA, 2011, 108(21):E128-E135.
Verdura et al., "Heterozygous HTRAI Mutations are Associated with Autosomal Dominant Cerebral Small Vessel Disease", Brain, Aug. 2015, 138:2347-2358.
Vermeer et al., "Silent brain infarcts: a systematic review," Lancet Neurol., 2007, 6(7):611-619.
Wardlaw et al., "Small vessel disease: mechanisms and clinical implications," Lancet Neurol, Jul. 2019, 18(7):684-696, 13 pages.
Wollenweber et al., "Cysteine-sparing CADASIL mutations in NOTCH3 show proaggregatory properties in vitro," Stroke, 2015, 46(3):786-792.
Xu et al., "Insights into Autoregulation of Notch3 from Structural and Functional Studies of Its Negative Regulatory Region," Structure, 2015, 23:1227-1235.
Yamamura et al., "Activation of Notch signaling by short-term treatment with Jagged-1 enhances store-operated $Ca2^{2+}$entry in human pulmonary arterial smooth muscle cells," Am J Physiol Cell Physiol., 2014, 306(9):C871-878.
Yoon et al., "NOTCH3 variants in patients with subcortical vascular cognitive impairment: a comparison with typical CADASIL patients," Neurobiol Aging, 2015, 36:2443.e1-2443.e7.
Zaucker et al., "notch3 is essential for oligodendrocyte development and vascular integrity in zebrafish," Dis Models Mech, Sep. 2013, 6(5):1246-1259.

Retina
N3WT
N3KO
hN3WT
C455R
MC
BM
EC
Lu

Brain

SEQUENCE LISTING

```
Sequence total quantity: 33
SEQ ID NO: 1            moltype = AA  length = 17
FEATURE                 Location/Qualifiers
source                  1..17
                        mol_type = protein
                        organism = synthetic construct
SEQUENCE: 1
CDDYYYGFGC NKFCRPR                                                   17

SEQ ID NO: 2            moltype = AA  length = 23
FEATURE                 Location/Qualifiers
source                  1..23
```

```
                       mol_type = protein
                       organism = synthetic construct
SEQUENCE: 2
CDDYYYGFGC NKFCRPRDDF FGH                                          23

SEQ ID NO: 3           moltype = AA  length = 17
FEATURE                Location/Qualifiers
source                 1..17
                       mol_type = protein
                       organism = synthetic construct
SEQUENCE: 3
CDENYYSATC NKFCRPR                                                 17

SEQ ID NO: 4           moltype = AA  length = 23
FEATURE                Location/Qualifiers
source                 1..23
                       mol_type = protein
                       organism = synthetic construct
SEQUENCE: 4
CDENYYSATC NKFCRPRNDF FGH                                          23

SEQ ID NO: 5           moltype = AA  length = 17
FEATURE                Location/Qualifiers
source                 1..17
                       mol_type = protein
                       organism = synthetic construct
SEQUENCE: 5
CDEHYYGEGC SVFCRPR                                                 17

SEQ ID NO: 6           moltype = AA  length = 23
FEATURE                Location/Qualifiers
source                 1..23
                       mol_type = protein
                       organism = synthetic construct
SEQUENCE: 6
CDEHYYGEGC SVFCRPRDDA FGH                                          23

SEQ ID NO: 7           moltype = AA  length = 17
FEATURE                Location/Qualifiers
source                 1..17
                       mol_type = protein
                       organism = synthetic construct
SEQUENCE: 7
CEPPAVGTAC TRLCRPR                                                 17

SEQ ID NO: 8           moltype = AA  length = 17
FEATURE                Location/Qualifiers
source                 1..17
                       mol_type = protein
                       organism = synthetic construct
SEQUENCE: 8
CSDNYYGDNC SRLCKKR                                                 17

SEQ ID NO: 9           moltype = AA  length = 23
FEATURE                Location/Qualifiers
source                 1..23
                       mol_type = protein
                       organism = synthetic construct
SEQUENCE: 9
CSDNYYGDNC SRLCKKRNDH FGH                                          23

SEQ ID NO: 10          moltype = AA  length = 2321
FEATURE                Location/Qualifiers
source                 1..2321
                       mol_type = protein
                       organism = Homo sapiens
SEQUENCE: 10
MGPGARGRRR RRRPMSPPPP PPPVRALPLL LLLAGPGAAA PPCLDGSPCA NGGRCTQLPS  60
REAACLCPPG WVGERCQLED PCHSGPCAGR GVCQSSVVAG TARFSCRCPR GFRGPDCSLP  120
DPCLSSPCAH GARCSVGPDG RFLCSCPPGY QGRSCRSDVD ECRVGEPCRH GGTCLNTPGS  180
FRCQCPAGYT GPLCENPAVP CAPSPCRNGG TCRQSGDLTY DCACLPGFEG QNCEVNVDDC  240
PGHRCLNGGT CVDGVNTYNC QCPPEWTGQF CTEDVDECQL QPNACHNGGT CFNTLGGHSC  300
VCVNGWTGES CSQNIDDCAT AVCFHGATCH DRVASFYCAC PMGKTGLLCH LDDACVSNPC  360
HEDAICDTNP VNGRAICTCP PGFTGGACDQ DVDECSIGAN PCEHLGRCVN TQGSFLCQCG  420
RGYTGPRCET DVNECLSGPC RNQATCLDRI GQFTCICMAG FTGTYCEVDI DECQSSPCVN  480
GGVCKDRVNG FSCTCPSGFS GSTCQLDVDE CASTPCRNGA KCVDQPDGYE CRCAEGFEGT  540
LCDRNVDDCS PDPCHHGRCV DGIASFSCAC APGYTGTRCE SQVDECRSQP CRHGGKCLDL  600
VDKYLCRCPS GTTGVNCEVN IDDCASNPCT FGVCRDGINR YDCVCQPGFT GPLCNVEINE  660
CASSPCGEGG SCVDGENGFR CLCPPGSLPP LCLPPSHPCA HEPCSHGICY DAPGGFRCVC  720
```

```
EPGWSGPRCS QSLARDACES QPCRAGGTCS SDGMGFHCTC PPGVQGRQCE LLSPCTPNPC  780
EHGGRCESAP GQLPVCSCPQ GWQGPRCQQD VDECAGPAPC GPHGICTNLA GSFSCTCHGG  840
YTGPSCDQDI NDCDPNPCLN GGSCQDGVGS FSCSCLPGFA GPRCARDVDE CLSNPCGPGT  900
CTDHVASFTC TCPPGYGGFH CEQDLPDCSP SSCFNGGTCV DGVNSFSCLC RPGYTGAHCQ  960
HEADPCLSRP CLHGGVCSAA HPGFRCTCLE SFTGPQCQTL VDWCSRQPCQ NGGRCVQTGA  1020
YCLCPPGWSG RLCDIRSLPC REAAAQIGVR LEQLCQAGGQ CVDEDSSHYC VCPEGRTGSH  1080
CEQEVDPCLA QPCQHGGTCR GYMGGYMCEC LPGYNGDNCE DDVDECASQP CQHGGSCIDL  1140
VARYLCSCPP GTLGVLCEIN EDDCGPGPPL DSGPRCLHNG TCVDLVGGFR CTCPPGYTGL  1200
RCEADINECR SGACHAAHTR DCLQDPGGGF RCLCHAGFSG PRCQTVLSPC ESQPCQHGGQ  1260
CRPSPGPGGG LTFTCHCAQP FWGPRCERVA RSCRELQCPV GVPCQQTPRG PRCACPPGLS  1320
GPSCRSFPGS PPGASNASCA AAPCLHGGSC RPAPLAPFFR CACAQGWTGP RCEAPAAAPE  1380
VSEEPRCPRA ACQAKRGDQR CDRECNSPGC GWDGGDCSLS VGDPWRQCEA LQCWRLFNNS  1440
RCDPACSSPA CLYDNFDCHA GGRERTCNPV YEKYCADHFA DGRCDQGCNT EECGWDGLDC  1500
ASEVPALLAR GVLVLTVLLP PEELLRSSAD FLQRLSAILR TSLRFRLDAH GQAMVFPYHR  1560
PSPGSEPRAR RELAPEVIGS VVMLEIDNRL CLQSPENDHC FPDAQSAADY LGALSAVERL  1620
DFPYPLRDVR GEPLEPPEPS VPLLPLLVAG AVLLLVILVL GVMVARRKRE HSTLWFPEGF  1680
SLHKDVASGH KGRREPVGQD ALGMKNMAKG ESLMGEVATD WMDTECPEAK RLKVEEPGMG  1740
AEEAVDCRQW TQHHLVAADI RVAPAMALTP PQGDADADGM DVNVRGPDGF TPLMLASFCG  1800
GALEPMPTEE DEADDTSASI ISDLICQGAQ LGARTDRTGE TALHLAARYA RADAAKRLLD  1860
AGADTNAQDH SGRTPLHTAV TADAQGVFQI LIRNRSTDLD ARMADGSTAL ILAARLAVEG  1920
MVEELIASHA DVNAVDELGK SALHWAAAVN NVEATLALLK NGANKDMQDS KEETPLFLAA  1980
REGSYEAAKL LLDHFANREI TDHLDRLPRD VAQERLHQDI VRLLDQPSGP RSPPGPHGLG  2040
PLLCPPGAFL PGLKAAQSGS KKSRRPPGKA GLGPQGPRGR GKKLTLACPG PLADSSVTLS  2100
PVDSLDSPRP FGGPPASPGG FPLEGPYAAA TATAVSLAQL GGPGRAGLGR QPPGGCVLSL  2160
GLLNPVAVPL DWARLPPPAP PGPSFLLPLA PGPQLLNPGT PVSPQERPPP YLAVPGHGEE  2220
YPAAGAHSSP PKARFLRVPS EHPYLTPSPE SPEHWASPSP PSLSDWSEST PSPATATGAM  2280
ATTTGALPAQ PLPLSVPSSL AQAQTQLGPQ PEVTPKRQVL A                       2321

SEQ ID NO: 11           moltype = DNA  length = 8091
FEATURE                 Location/Qualifiers
source                  1..8091
                        mol_type = genomic DNA
                        organism = Homo sapiens
SEQUENCE: 11
acgcggcgcg gaggctggcc cgggacgcgc ccggagccca gggaaggagg gaggagggga  60
gggtcgcggc cggccgccat ggggccgggg gcccgtggcc gccgccgccg ccgtcgcccg  120
atgtcgccgc caccgccacc gccacccgtg cgggcgctgc ccctgctgct gctgctagcg  180
gggccggggg ctgcagcccc cccttgcctg gacggaagcc cgtgtgcaaa tggaggtcgt  240
tgcacccagc tgccctcccg ggaggctgcc tgcctgtgcc cgcctggctg ggtgggtgag  300
cggtgtcagc tggaggaccc ctgtcactca ggcccctgtg ctggccgtgg tgtctgccag  360
agttcagtgg tggctggcac cgcccgattc tcatgccggt gcccccgtgg cttccgaggc  420
cctgactgct ccctgccaga tccctgcctc agcagccctt gtgcccacgg tgcccgctgc  480
tcagtggggc ccgatggacg cttcctctgc tcctgcccac ctggctacca gggccgcagc  540
tgccgaagcg acgtggatga gtgccgggtg ggtgagccct gccgccatgg tggcacctgc  600
ctcaacacac ctggctcctt ccgctgccag tgtccagctg gctacacagg gccactatgt  660
gagaaccccg cggtgccctg tgcgccctca ccatgccgta acgggggcac ctgcaggcag  720
agtggcgacc tcacttacga ctgtgcctgt cttcctgggt ttgagggtca gaattgtgaa  780
gtgaacgtgg acgactgtcc aggacaccga tgtctcaatg gggggacatg cgtggatggc  840
gtcaacacct ataactgcca gtgccctcct gagtggacag gccagttctg cacggaggac  900
gtggatgagt gtcagctgca gcccaacgcc tgccacaatg gggtacctg cttcaacacg  960
ctgggtggcc acagctgcgt gtgtgtcaat ggctggacag gtgagagctg cagtcagaat  1020
atcgatgact gtgccacagc cgtgtgcttc catggggcca cctgccatga ccgcgtggct  1080
tctttctact gtgcctgccc catgggcaag actggcctcc tgtgtcacct ggatgacgcc  1140
tgtgtcagca acccctgcca cgaggatgct atctgtgaca caaatccggt gaacggccgg  1200
gccatttgca cctgtcctcc cggcttcacg ggtggggcat gtgaccagga tgtggacgag  1260
tgctctatcg gcgccaaccc ctgcgagcac ttgggcaggt gcgtgaacac gcagggctcc  1320
ttcctgtgcc agtgcggtcg tggctacact ggacctcgct gtgagaccga tgtcaacgag  1380
tgtctgtcgg ggccctgccg aaaccaggcc acgtgcctcg accgcatagg ccagttcacc  1440
tgtatctgta tggcaggctt cacaggaacc tattgcgagg tggacattga cgagtgtcag  1500
agtagcccct gtgtcaacgg tggggtctgc aaggaccgag tcaatggctt cagctgcacc  1560
tgccccctcgg gcttcagcgg ctccacgtgt cagctggacg tggacgaatg cgccagcacg  1620
ccctgcagga atggcgccaa atgcgtggac cagcccgatg gctacgagtg ccgctgtgcc  1680
gagggctttg agggcacgct gtgtgatcgc aacgtggacg actgctcccc tgacccatgc  1740
caccatggtc gctgcgtgga tggcatcgcc agcttctcat gtgcctgtgc tcctggctac  1800
acgggcacac gctgcgagag ccaggtggac gaatgccgca gccagccctg ccgccatggc  1860
ggcaaatgcc tagacctggt ggacaagtac ctctgccgct gcccttctgg gaccacaggt  1920
gtgaactgcg aagtgaacat tgacgactgt gccagcaacc cctgcacctt tggagtctgc  1980
cgtgatggca tcaaccgcta cgactgtgtc tgccaacctg gcttcacagg gccccctttgt  2040
aacgtggaga tcaatgagtg tgcttccagc ccatgcggcg agggaggttc ctgtgtggat  2100
ggggaaaatg gcttccgctg cctctgcccg cctggctcct tgccccccact ctgcctcccc  2160
ccgagccatc cctgtgccca tgagccctgc agtcacggca tctgctatga tgcacctggc  2220
gggttccgct gtgtgtgtga gcctggctgg agtggccccc gctgcagcca gagcctggcc  2280
cgagacgcct gtgagtccca gccgtgcagg gccggtggga catgcagcag cgatggaatg  2340
ggtttccact gcacctgccc gcctggtgtc cagggacgtc agtgtgaact cctctccccc  2400
tgcaccccga acccctgtga gcatgggggc cgctgcgagt ctgcccctgg ccagctgcct  2460
gtctgctcct gcccccaggg ctggcaaggc ccacgatgcc agcaggatgt ggacgagtgt  2520
gctggccccg caccctgtgg ccctcatggt atctgcacca acctggcagg gagtttcagc  2580
tgcacctgcc atggagggta cactggccct tcctgtgatc aggacatcaa tgactgtgac  2640
cccaacccat gcctgaacgg tggctcgtgc caagacggcg tgggctcctt ttcctgctcc  2700
```

-continued

```
tgcctccctg gtttcgccgg cccacgatgc gcccgcgatg tggatgagtg cctgagcaac  2760
ccctgcggcc cgggcacctg taccgaccac gtggcctcct tcacctgcac ctgcccgccg  2820
ggctacggag gcttccactg cgaacaggac ctgcccgact gcagccccag ctcctgcttc  2880
aatggcggga cctgtgtgga cggcgtgaac tcgttcagct gcctgtgccg tcccggctac  2940
acaggagccc actgccaaca tgaggcagac ccctgcctct cgcggccctg cctacacggg  3000
ggcgtctgca gcgccgccca ccctggcttc cgctgcacct gcctcgagag cttcacgggc  3060
ccgcagtgcc agacgctggt ggattggtgc agccgccagc cttgtcaaaa cgggggtcgc  3120
tgcgtccaga ctggggccta ttgcctttgt ccccctggat ggagcggacg cctctgtgac  3180
atccgaagct tgccctgcag ggaggccgca gcccagatcg ggtgcggct ggagcagctg  3240
tgtcaggcgg gtgggcagtg tgtggatgaa gacagctccc actactgcgt gtgcccagag  3300
ggccgtactg gtagccactg tgagcaggag gtggacccct gcttggccca gccctgccag  3360
catgggggga cctgccgtgg ctatatgggg ggctacatgt gtgagtgtct tcctggctac  3420
aatggtgata actgtgagga cgacgtggac gagtgtgcct cccagccctg ccagcacggg  3480
ggttcatgca ttgacctcgt ggcccgctat ctctgctcct gtcccccagg aacgctgggg  3540
gtgctctgcg agattaatga ggatgactgc ggcccaggcc caccgctgga ctcagggccc  3600
cggtgcctac acaatggcac ctgcgtggac ctggtgggtg gtttccgctg cacctgtccc  3660
ccaggataca ctggtttgcg ctgcgaggca gacatcaatg agtgtcgctc aggtgcctgc  3720
cacgcggcac acacccggga ctgcctgcag gacccaggcg gaggtttccg ttgcctttgt  3780
catgctggct tctcaggtcc tcgctgtcag actgtcctgt ctccctgcga gtcccagcca  3840
tgccagcatg gaggccagtg ccgtcctagc ccgggtcctg gggtgggct gaccttcacc  3900
tgtcactgtg cccagccgtt ctggggtccg cgttgcgagc gggtggcgcg ctcctgccgg  3960
gagctgcagt gcccggtggg cgtcccatgc cagcagacgc cccgcgggcc gcgctgcgcc  4020
tgcccccag ggttgtcggg accctcctgc cgcagcttcc cggggtcgcc gccgggggcc  4080
agcaacgcca gctgcgcggc cgccccctgt ctccacgggg gctcctgccg ccccgcgccg  4140
ctcgcgccct tcttccgctg cgcttgcgcg cagggctgga ccgggccgcg ctgcgaggcg  4200
cccgccgcgg cacccgaggt ctcggaggag ccgcggtgcc cgcgcgccgc ctgccaggcc  4260
aagcgcgggg accagcgctg cgaccgcgag tgcaacagcc caggctgcgg ctgggacggc  4320
ggcgactgct cgctgagcgt gggcgacccc tggcggcaat gcgaggcgct gcagtgctgg  4380
cgcctcttca acaacagccg ctgcgacccc gcctgcagct cgcccgcctg cctctacgac  4440
aacttcgact gccacgccgg tggccgcgag cgcacttgca acccggtgta cgagaagtac  4500
tgcgccgacc actttgccga cggccgctgc gaccagggct gcaacacgga ggagtgcggc  4560
tgggatgggc tggattgtgc cagcgaggtg ccggccctgc tggcccgcgg cgtgctggtg  4620
ctcacagtgc tgctgccgcc ggaggagcta ctgcgttcca gcgccgactt tctgcagcgg  4680
ctcagcgcca tcctgcgcac ctcgctgcgc ttccgcctgg acgcgcacgg ccaggccatg  4740
gtcttccctt accaccggcc tagtcctggc tccgaacccc gggcccgtcg ggagctggcc  4800
cccgaggtga tcggctcggt agtaatgctg gagattgaca accggctctg cctgcagtcg  4860
cctgagaatg atcactgctt ccccgatgcc cagagcgccg ctgactacct gggagcgttg  4920
tcagcggtgg agcgcctgga cttcccgtac ccactgcggg acgtgcgggg ggagccgctg  4980
gagcctccag aacccagcgt cccgctgctg ccactgctag tggcgggcgc tgtcttgctg  5040
ctggtcattc tcgtcctggg tgtcatggtg gcccggcgca agcgcgagca cagcaccctc  5100
tggttccctg agggcttctc actgcacaag gacgtggcct ctggtcacaa gggccggcgg  5160
gaacccgtgg gccaggacgc gctgggcatg aagaacatgg ccaagggtga gagcctgatg  5220
ggggaggtgg ccacagactg gatggacaca gagtgcccag aggccaagcg gctaaaggta  5280
gaggagccag gcatgggggc tgaggaggct gtggattgcc gtcagtggac tcaacaccat  5340
ctggttgctg ctgacatccg cgtggcacca gccatggcac tgacaccacc acagggcgac  5400
gcagatgctg atggcatgga tgtcaatgtg cgtggcccag atggcttcac cccgctaatg  5460
ctggcttcct tctgtggggg ggctctggag ccaatgccaa ctgaagagga tgaggcagat  5520
gacacatcag ctagcatcat ctccgacctg atctgccagg gggctcagct tggggcacgg  5580
actgaccgta ctggcgagac tgctttgcac ctggctgccc gttatgcccg tgctgatgca  5640
gccaagcggc tgctggatgc tggggcagac accaatgccc aggaccactc aggccgcact  5700
cccctgcaca cagctgtcac agccgatgcc cagggtgtct tccagattct catccgaaac  5760
cgctctacag acttggatgc ccgcatggca gatggctcaa cggcactgat cctggcggcc  5820
cgcctggcag tagagggcat ggtggaagag ctcatcgcca gccatgctga tgtcaatgct  5880
gtggatgagc ttgggaaatc agccttacac tgggctgcgg ctgtgaacaa cgtggaagcc  5940
actttggccc tgctcaaaaa tggagccaat aaggacatgc aggatagcaa ggaggagacc  6000
cccctattcc tggccgcccg cgagggcagc tatgaggctg ccaagctgct gttggaccac  6060
tttgccaacc gtgagatcac cgaccacctg gacaggctgc cgcgggacgt agcccaggag  6120
agactgcacc aggacatcgt gcgcttgctg gatcaaccca gtgggccccg cagcccccc  6180
ggtccccacg gcctggggcc tctgctctgt cctccagggg ccttcctccc tggcctcaaa  6240
gcggcacagt cggggtccaa gaagagcagg aggcccccg ggaaggcggg gctggggccg  6300
caggggcccc gggggcgggg caagaagctg acgctggcct gcccgggccc cctggctgac  6360
agctcggtca cgctgtcgcc cgtggactcg ctggactccc cgcggccttt cggtgggccc  6420
cctgcttccc ctggtggctt ccccttgag gggccctatg cagctgccac tgccactgca  6480
gtgtctctgg cacagcttgg tggcccaggc cgggcaggtc tagggcgcca gcccctgga  6540
ggatgtgtac tcagcctggg cctgctgaac cctgtggctg tgcccctcga ttgggcccgg  6600
ctgcccccac ctgcccctcc aggcccctcg ttcctgctgc cactggcgcc gggaccccag  6660
ctgctcaacc cagggacccc cgtctccccg caggagcggc cccgcctta cctggcagtc  6720
ccaggacatg gcgaggagta cccggtggct ggggcacaca gcagcccccc aaaggcccgc  6780
ttcctgcggg ttcccagtga gcacccttac ctgaccccat cccccgaatc ccctgagcac  6840
tgggccagcc cctcacctcc ctccctctca gactggtccg aatccacgcc tagcccagcc  6900
actgccactg gggccatggc caccaccact ggggcactgc ctgcccagcc acttcccttg  6960
tctgttccca gctcccttgc tcaggcccag acccagctgg ggccccagcc ggaagttacc  7020
cccaagaggc aagtgttggc ctgagacgct cgtcagttct tagatcttgg gggcctaaag  7080
agacccccgt cctgcctcct ttctttctct gtctcttcct tccttttagt ctttttcatc  7140
ctcttctctt tccaccaacc ctcctgcatc cttgccttgc agcgtgaccg agataggtca  7200
tcagcccagg gcttcagtct tcctttattt ataatgggtg gggctacca cccaccctct  7260
cagtcttgtg aagagtctgg gacctccttc ttccccactt ctctcttccc tcattccttt  7320
ctctctcctt ctggcctctc atttccttac actctgacat gaatgaatta ttattatttt  7380
tctttttctt tttttttta cattttgtat agaaacaaat tcatttaaac aaacttatta  7440
```

-continued ttattatttt ttacaaaata tatatatgga gatgctccct ccccctgtga accccccagt 7500
gcccccgtgg ggctgagtct gtgggcccat tcggccaagc tggattctgt gtacctagta 7560
cacaggcatg actgggatcc cgtgtaccga gtacacgacc caggtatgta ccaagtaggc 7620
acccttgggc gcacccactg gggccagggg tcgggggagt gttgggagcc tcctccccac 7680
cccacctccc tcacttcact gcattccaga ttggacatgt tccatagcct tgctggggaa 7740
gggcccactg ccaactccct ctgccccagc cccacccttg gccatctccc tttgggaact 7800
agggggctgc tggtgggaaa tgggagccag ggcagatgta tgcattcctt tatgtccctg 7860
taaatgtggg actacaagaa gaggagctgc ctgagtggta ctttctcttc ctggtaatcc 7920
tctggcccag ccttatggca gaatagaggt atttttaggc tatttttgta atatggcttc 7980
tggtcaaaat ccctgtgtag ctgaattccc aagccctgca ttgtacagcc ccccactccc 8040
ctcaccacct aataaaggaa tagttaacac tcaaaaaaaa aaaaaaaaaa a 8091

SEQ ID NO: 12 moltype = AA length = 1532
FEATURE Location/Qualifiers
source 1..1532
mol_type = protein
organism = Homo sapiens
SEQUENCE: 12
APPCLDGSPC ANGGRCTQLP SREAACLCPP GWVGERCQLE DPCHSGPCAG RGVCQSSVVA 60
GTARFSCRCP RGFRGPDCSL PDPCLSSPCA HGARCSVGPD GRFLCSCPPG YQGRSCRSDV 120
DECRVGEPCR HGGTCLNTPG SFRCQCPAGY TGPLCENPAV PCAPSPCRNG GTCRQSGDLT 180
YDCACLPGFE GQNCEVNVDD CPGHRCLNGG TCVDGVNTYN CQCPPEWTGQ FCTEDVDECQ 240
LQPNACHNGG TCFNTLGGHS CVCVNGWTGE SCSQNIDDCA TAVCFHGATC HDRVASFYCA 300
CPMGKTGLLC HLDDACVSNP CHEDAICDTN PVNGRAICTC PPGFTGGACD QDVDECSIGA 360
NPCEHLGRCV NTQGSFLCQC GRGYTGPRCE TDVNECLSGP CRNQATCLDR IGQFTCICMA 420
GFTGTYCEVD IDECQSSPCV NGGVCKDRVN GFSCTCPSGF SGSTCQLDVD ECASTPCRNG 480
AKCVDQPDGY ECRCAEGFEG TLCDRNVDDC SPDPCHHGRC VDGIASFSCA CAPGYTGTRC 540
ESQVDECRSQ PCRHGGKCLD LVDKYLCRCP SGTTGVNCEV NIDDCASNPC TFGVCRDGIN 600
RYDCVCQPGF TGPLCNVEIN ECASSPCGEG GSCVDGENGF RCLCPPGSLP PLCLPPSHPC 660
AHEPCSHGIC YDAPGGFRCV CEPGWSGPRC SQSLARDACE SQPCRAGGTC SSDGMGFHCT 720
CPPGVQGRQC ELLSPCTPNP CEHGGRCESA PGQLPVCSCP QGWQGPRCQQ DVDECAGPAP 780
CGPHGICTNL AGSFSCTCHG GYTGPSCDQD INDCDPNPCL NGGSCQDGVG SFSCSCLPGF 840
AGPRCARDVD ECLSNPCGPG TCTDHVASFT CTCPPGYGGF HCEQDLPDCS PSSCFNGGTC 900
VDGVNSFSCL CRPGYTGAHC QHEADPCLSR PCLHGGVCSA AHPGFRCTCL ESFTGPQCQT 960
LVDWCSRQPC QNGGRCVQTG AYCLCPPGWS GRLCDIRSLP CREAAAQIGV RLEQLCQAGG 1020
QCVDEDSSHY CVCPEGRTGS HCEQEVDPCL AQPCQHGGTC RGYMGGYMCE CLPGYNGDNC 1080
EDDVDECASQ PCQHGGSCID LVARYLCSCP PGTLGVLCEI NEDDCGPGPP LDSGPRCLHN 1140
GTCVDLVGGF RCTCPPGYTG LRCEADINEC RSGACHAAHT RDCLQDPGGG FRCLCHAGFS 1200
GPRCQTVLSP CESQPCQHGG QCRPSPGPGG GLTFTCHCAQ PFWGPRCERV ARSCRELQCP 1260
VGVPCQQTPR GPRCACPPGL SGPSCRSFPG SPPGASNASC AAAPCLHGGS CRPAPLAPFF 1320
RCACAQGWTG PRCEAPAAAP EVSEEPRCPR AACQAKRGDQ RCDRECNSPG CGWDGGDCSL 1380
SVGDPWRQCE ALQCWRLFNN SRCDPACSSP ACLYDNFDCH AGGRERTCNP VYEKYCADHF 1440
ADGRCDQGCN TEECGWDGLD CASEVPALLA RGVLVLTVLL PPEELLRSSA DFLQRLSAIL 1500
RTSLRFRLDA HGQAMVFPYH RPSPGSEPRA RR 1532

SEQ ID NO: 13 moltype = AA length = 1533
FEATURE Location/Qualifiers
source 1..1533
mol_type = protein
organism = Mus musculus
SEQUENCE: 13
APPCLDGSPC ANGGRCTHQQ PSLEAACLCL PGWVGERCQL EDPCHSGPCA GRGVCQSSVV 60
AGTARFSCRC LRGFQGPDCS QPDPCVSRPC VHGAPCSVGP DGRFACACPP GYQGQSCQSD 120
IDECRSGTTC RHGGTCLNTP GSFRCQCPLG YTGLLCENPV VPCAPSPCRN GGTCRQSSDV 180
TYDCACLPGF EGQNCEVNVD DCPGHRCLNG GTCVDGVNTY NCQCPPEWTG QFCTEDVDEC 240
QLQPNACHNG GTCFNLLGGH SCVCVNGWTG ESCSQNIDDC ATAVCFHGAT CHDRVASFYC 300
ACPMGKTGLL CHLDDACVSN PCHEDAICDT NPVSGRAICT CPPGFTGGAC DQDVDECSIG 360
ANPCEHLGRC VNTQGSFLCQ CGRGYTGPRC ETDVNECLSG PCRNQATCLD RIGQFTCICM 420
AGFTGTYCEV DIDECQSSPC VNGGVCKDRV NGFSCTCPSG FSGSMCQLDV DECASTPCRN 480
GAKCVDQPDG YECRCAEGFE GTLCERNVDD CSPDPCHHGR CVDGIASFSC ACAPGYTGIR 540
CESQVDECRS QPCRYGGKCL DLVDKYLCRC PPGTTGVNCE VNIDDCASNP CTFGVCRDGI 600
NRYDCVCQPG FTGPLCNVEI NECASSPCGE GGSCVDGENG FHCLCPPGSL PPLCLPANHP 660
CAHKPCSHGV CHDAPGGFRC VCEPGWSGPR CSQSLAPDAC ESQPCQAGGT CTSDGIGFRC 720
TCAPGFQGHQ CEVLSPCTPS LCEHGGHCES DPDRLTVCSC PPGWQGPRCQ QDVDECAGAS 780
PCGPHGTCTN LPGNFRCICH RGYTGPFCDQ DIDDCDPNPC LHGGSCQDGV GSFSCSCLDG 840
FAGPRCARDV DECLSSPCGP GTCTDHVASF TCACPPGYGG FHCEIDLPDC SPSSCFNGGT 900
CVDGVSSFSC LCRPGYTGTH CQYEADPCFS RPCLHGGICN PTHPGFECTC REGFTGSQCQ 960
NPVDWCSQAP CQNGGRCVQT GAYCICPPGW SGRLCDIQSL PCTEAAAQMG VRLEQLCQEG 1020
GKCIDKGRSH YCVCPEGRTG SHCEHEVDPC TAQPCQHGGT CRGYMGGYVC ECPAGYAGDS 1080
CEDNIDECAS QPCQNGGSCI DLVARYLCSC PPGTLGVLCE INEDDCDLGP SLDSGVQCLH 1140
NGTCVDLVGG FRCNCPPGYT GLHCEADINE CRPGACHAAH TRDCLQDPGG HFRCVCHPGF 1200
TGPRCQIALS PCESQPCQHG GQCRHSLGRG GGLTFTCHCV PPFWGLRCER VARSCRELQC 1260
PVGIPCQQTA RGPRCACPPG LSGPSCRVSR ASPSGATNAS CASAPCLHGG SCLPVQSVPF 1320
FRCVCAPGWG GPRCETPSAA PEVPEEPRCP RAACQAKRGD QNCDRECNTP GCGWDGGDCS 1380
LNVDDPWRQC EALQCWRLFN NSRCDPACSS PACLYDNFDC YSGGRDRTCN PVYEKYCADH 1440
FADGRCDQGC NTEECGWDGL DCASEVPALL ARGVLVLTVL LPPEELLRSS ADFLQRLSAI 1500
LRTSLRFRLD ARGQAMVFPY HRPSPGSESR VRR 1533

SEQ ID NO: 14 moltype = AA length = 1218

```
FEATURE              Location/Qualifiers
source               1..1218
                     mol_type = protein
                     organism = Homo sapiens
SEQUENCE: 14
MRSPRTRGRS GRPLSLLLAL LCALRAKVCG ASGQFELEIL SMQNVNGELQ NGNCCGGARN  60
PGDRKCTRDE CDTYFKVCLK EYQSRVTAGG PCSFGSGSTP VIGGNTFNLK ASRGNDRNRI  120
VLPFSFAWPR SYTLLVEAWD SSNDTVQPDS IIEKASHSGM INPSRQWQTL KQNTGVAHFE  180
YQIRVTCDDY YYGFGCNKFC RPRDDFFGHY ACDQNGNKTC MEGWMGPECN RAICRQGCSP  240
KHGSCKLPGD CRCQYGWQGL YCDKCIPHPG CVHGICNEPW QCLCETNWGG QLCDKDLNYC  300
GTHQPCLNGG TCSNTGPDKY QCSCPEGYSG PNCEIAEHAC LSDPCHNRGS CKETSLGFEC  360
ECSPGWTGPT CSTNIDDCSP NNCSHGGTCQ DLVNGFKCVC PPQWTGKTCQ LDANECEAKP  420
CVNAKSCKNL IASYYCDCLP GWMGQNCDIN INDCLGQCQN DASCRDLVNG YRCICPPGYA  480
GDHCERDIDE CASNPCLNGG HCQNEINRFQ CLCPTGFSGN LCQLDIDYCE PNPCQNGAQC  540
YNRASDYFCK CPEDYEGKNC SHLKDHCRTT PCEVIDSCTV AMASNDTPEG VRYISSNVCG  600
PHGKCKSQSG GKFTCDCNKG FTGTYCHENI NDCESNPCRN GGTCIDGVNS YKCICSDGWE  660
GAYCETNIND CSQNPCHNGG TCRDLVNDFY CDCKNGWKGK TCHSRDSQCD EATCNNGGTC  720
YDEGDAFKCM CPGGWEGTTC NIARNSSCLP NPCHNGGTCV VNGESFTCVC KEGWEGPICA  780
QNTNDCSPHP CYNSGTCVDG DNWYRCECAP GFAGPDCRIN INECQSSPCA FGATCVDEIN  840
GYRCVCPPGH SGAKCQEVSG RPCITMGSVI PDGAKWDDDC NTCQCLNGRI ACSKVWCGPR  900
PCLLHKGHSE CPSGQSCIPI LDDQCFVHPC TGVGECRSSS LQPVKTKCTS DSYYQDNCAN  960
ITFTFNKEMM SPGLTTEHIC SELRNLNILK NVSAEYSIYI ACEPSPSANN EIHVAISAED  1020
IRDDGNPIKE ITDKIIDLVS KRDGNSSLIA AVAEVRVQRR PLKNRTDFLV PLLSSVLTVA  1080
WICCLVTAFY WCLRKRRKPG SHTHSASEDN TTNNVREQLN QIKNPIEKHG ANTVPIKDYE  1140
NKNSKMSKIR THNSEVEEDD MDKHQQKARF AKQPAYTLVD REEKPPNGTP TKHPNWTNKQ  1200
DNRDLESAQS LNRMEYIV                                                1218

SEQ ID NO: 15        moltype = AA  length = 1034
FEATURE              Location/Qualifiers
source               1..1034
                     mol_type = protein
                     organism = Homo sapiens
SEQUENCE: 15
QFELEILSMQ NVNGELQNGN CCGGARNPGD RKCTRDECDT YFKVCLKEYQ SRVTAGGPCS  60
FGSGSTPVIG GNTFNLKASR GNDRNRIVLP FSFAWPRSYT LLVEAWDSSN DTVQPDSIIE  120
KASHSGMINP SRQWQTLKQN TGVAHFEYQI RVTCDDYYYG FGCNKFCRPR DDFFGHYACD  180
QNGNKTCMEG WMGPECNRAI CRQGCSPKHG SCKLPGDCRC QYGWQGLYCD KCIPHPGCVH  240
GICNEPWQCL CETNWGGQLC DKDLNYCGTH QPCLNGGTCS NTGPDKYQCS CPEGYSGPNC  300
EIAEHACLSD PCHNRGSCKE TSLGFECECS PGWTGPTCST NIDDCSPNNC SHGGTCQDLV  360
NGFKCVCPPQ WTGKTCQLDA NECEAKPCVN AKSCKNLIAS YYCDCLPGWM GQNCDININD  420
CLGQCQNDAS CRDLVNGYRC ICPPGYAGDH CERDIDECAS NPCLNGGHCQ NEINRFQCLC  480
PTGFSGNLCQ LDIDYCEPNP CQNGAQCYNR ASDYFCKCPE DYEGKNCSHL KDHCRTTPCE  540
VIDSCTVAMA SNDTPEGVRY ISSNVCGPHG KCKSQSGGKF TCDCNKGFTG TYCHENINDC  600
ESNPCRNGGT CIDGVNSYKC ICSDGWEGAY CETNINDCSQ NPCHNGGTCR DLVNDFYCDC  660
KNGWKGKTCH SRDSQCDEAT CNNGGTCYDE GDAFKCMCPG GWEGTTCNIA RNSSCLPNPC  720
HNGGTCVVNG ESFTCVCKEG WEGPICAQNT NDCSPHPCYN SGTCVDGDNW YRCECAPGFA  780
GPDCRININE CQSSPCAFGA TCVDEINGYR CVCPPGHSGA KCQEVSGRPC ITMGSVIPDG  840
AKWDDDCNTC QCLNGRIACS KVWCGPRPCL LHKGHSECPS GQSCIPILDD QCFVHPCTGV  900
GECRSSSLQP VKTKCTSDSY YQDNCANITF TFNKEMMSPG LTTEHICSEL RNLNILKNVS  960
AEYSIYIACE PSPSANNEIH VAISAEDIRD DGNPIKEITD KIIDLVSKRD GNSSLIAAVA  1020
EVRVQRRPLK NRTD                                                    1034

SEQ ID NO: 16        moltype = AA  length = 1238
FEATURE              Location/Qualifiers
source               1..1238
                     mol_type = protein
                     organism = Homo sapiens
SEQUENCE: 16
MRAQGRGRLP RRLLLLLALW VQAARPMGYF ELQLSALRNV NGELLSGACC DGDGRTTRAG  60
GCGHDECDTY VRVCLKEYQA KVTPTGPCSY GHGATPVLGG NSFYLPPAGA AGDRARARAR  120
AGGDQDPGLV VIPFQFAWPR SFTLIVEAWD WDNDTTPNEE LLIERVSHAG MINPEDRWKS  180
LHFSGHVAHL ELQIRVRCDE NYYSATCNKF CRPRNDFFGH YTCDQYGNKA CMDGWMGKEC  240
KEAVCKQGCN LLHGGCTVPG ECRCSYGWQG RFCDECVPYP GCVHGSCVEP WQCNCETNWG  300
GLLCDKDLNY CGSHHPCTNG GTCINAEPDQ YRCTCPDGYS GRNCEKAEHA CTSNPCANGG  360
SCHEVPSGFE CHCPSGWSGP TCALDIDECA SNPCAAGGTC VDQVDGFECI CPEQWVGATC  420
QLDANECEGK PCLNAFSCKN LIGGYYCDCI PGWKGINCHI NVNDCRGQCQ HGGTCKDLVN  480
GYQCVCPRGF GGRHCELERD ECASSPCHSG GLCEDLADGF HCHCPQGFSG PLCEVDVDLC  540
EPSPCRNGAR CYNLEGDYYC ACPDDFGGKN CSVPREPCPG GACRVIDGCG SDAGPGMPGT  600
AASGVCGPHG RCVSQPGGNF SCICDSGFTG TYCHENIDDC LGQPCRNGGT CIDEVDAFRC  660
FCPSGWEGEL CDTNPNDCLP DPCHSRGRCY DLVNDFYCAC DDGWKGKTCH SREFQCDAYT  720
CSNGGTCYDS GDTFRCACPP GWKGSTCAVA KNSSCLPNPC VNGGTCVGSG ASFSCICRDG  780
WEGRTCTHNT NDCNPLPCYN GGICVDGVNW FRCECAPGFA GPDCRINIDE CQSSPCAYGA  840
TCVDEINGYR CSCPPGRAGP RCQEVIGFGR SCWSRGTPFP HGSSWVEDCN SCRCLDGRRD  900
CSKVWCGWKP CLLAGQPEAL SAQCPLGQRC LEKAPGQCLR PPCEAWGECG AEEPPSTPCL  960
PRSGHLDNNC ARLTLHFNRD HVPQGTTVGA ICSGIRSLPA TRAVARDRLL VLLCDRASSG  1020
ASAVEVAVSF SPARDLPDSS LIQGAAHAIV AAITQRGNSS LLLAVTEVKV ETVVTGGSST  1080
GLLVPVLCGA FSVLWLACVV LCVWWTRKRR KERERSRLPR EESANNQWAP LNPIRNPIER  1140
PGGHKDVLYQ CKNFTPPPRR ADEALPGPAG HAAVREDEED EDLGRGEEDS LEAEKFLSHK  1200
FTKDPGRSPG RPAHWASGPK VDNRAVRSIN EARYAGKE                          1238
```

```
SEQ ID NO: 17          moltype = AA  length = 1054
FEATURE                Location/Qualifiers
source                 1..1054
                       mol_type = protein
                       organism = Homo sapiens
SEQUENCE: 17
MGYFELQLSA LRNVNGELLS GACCDGDGRT TRAGGCGHDE CDTYVRVCLK EYQAKVTPTG  60
PCSYGHGATP VLGGNSFYLP PAGAAGDRAR ARARAGGDQD PGLVVIPFQF AWPRSFTLIV  120
EAWDWDNDTT PNEELLIERV SHAGMINPED RWKSLHFSGH VAHLELQIRV RCDENYYSAT  180
CNKFCRPRND FFGHYTCDQY GNKACMDGWM GKECKEAVCK QGCNLLHGGC TVPGECRCSY  240
GWQGRFCDEC VPYPGCVHGS CVEPWQCNCE TNWGGLLCDK DLNYCGSHHP CTNGGTCINA  300
EPDQYRCTCP DGYSGRNCEK AEHACTSNPC ANGGSCHEVP SGFECHCPSG WSGPTCALDI  360
DECASNPCAA GGTCVDQVDG FECICPEQWV GATCQLDANE CEGKPCLNAF SCKNLIGGYY  420
CDCIPGWKGI NCHINVNDCR GQCQHGGTCK DLVNGYQCVC PRGFGGRHCE LERDECASSP  480
CHSGGLCEDL ADGFHCHCPQ GFSGPLCEVD VDLCEPSPCR NGARCYNLEG DYYCACPDDF  540
GGKNCSVPRE PCPGGACRVI DGCGSDAGPG MPGTAASGVC GPHGRCVSQP GGNFSCICDS  600
GFTGTYCHEN IDDCLGQPCR NGGTCIDEVD AFRCFCPSGW EGELCDTNPN DCLPDPCHSR  660
GRCYDLVNDF YCACDDGWKG KTCHSREFQC DAYTCSNGGT CYDSGDTFRC ACPPGWKGST  720
CAVAKNSSCL PNPCVNGGTC VGSGASFSCI CRDGWEGRTC THNTNDCNPL PCYNGGICVD  780
GVNWFRCECA PGFAGPDCRI NIDECQSSPC AYGATCVDEI NGYRCSCPPG RAGPRCQEVI  840
GFGRSCWSRG TPFPHGSSWV EDCNSCRCLD GRRDCSKVWC GWKPCLLAGQ PEALSAQCPL  900
GQRCLEKAPG QCLRPPCEAW GECGAEEPPS TPCLPRSGHL DNNCARLTLH FNRDHVPQGT  960
TVGAICSGIR SLPATRAVAR DRLLVLLCDR ASSGASAVEV AVSFSPARDL PDSSLIQGAA  1020
HAIVAAITQR GNSSLLLAVT EVKVETVVTG GSST                             1054

SEQ ID NO: 18          moltype = AA  length = 723
FEATURE                Location/Qualifiers
source                 1..723
                       mol_type = protein
                       organism = Homo sapiens
SEQUENCE: 18
MGSRCALALA VLSALLCQVW SSGVFELKLQ EFVNKKGLLG NRNCCRGGAG PPPCACRTFF  60
RVCLKHYQAS VSPEPPCTYG SAVTPVLGVD SFSLPDGGGA DSAFSNPIRF PFGFTWPGTF  120
SLIIEALHTD SPDDLATENP ERLISRLATQ RHLTVGEEWS QDLHSSGRTD LKYSYRFVCD  180
EHYYGEGCSV FCRPRDDAFG HFTCGERGEK VCNPGWKGPY CTEPICLPGC DEQHGFCDKP  240
GECKCRVGWQ GRYCDECIRY PGCLHGTCQQ PWQCNCQEGW GGLFCNQDLN YCTHHKPCKN  300
GATCTNTGQG SYTCSCRPGY TGATCELGID ECDPSPCKNG GSCTDLENSY SCTCPPGFYG  360
KICELSAMTC ADGPCFNGGR CSDSPDGGYS CRCPVGYSGF NCEKKIDYCS SSPCSNGAKC  420
VDLGDAYLCR CQAGFSGRHC DDNVDDCASS PCANGGTCRD GVNDFSCTCP PGYTGRNCSA  480
PVSRCEHAPC HNGATCHERG HRYVCECARG YGGPNCQFLL PELPPGPAVV DLTEKLEGQG  540
GPFPWVAVCA GVILVLMLLL GCAAVVVCVR LRLQKHRPPA DPCRGETETM NNLANCQREK  600
DISVSIIGAT QIKNTNKKAD FHGDHSADKN GFKARYPAVD YNLVQDLKGD DTAVRDAHSK  660
RDTKCQPQGS SGEEKGTPTT LRGGEASERK RPDSGCSTSK DTKYQSVYVI SEEKDECVIA  720
TEV                                                               723

SEQ ID NO: 19          moltype = AA  length = 528
FEATURE                Location/Qualifiers
source                 1..528
                       mol_type = protein
                       organism = Homo sapiens
SEQUENCE: 19
QVWSSGVFEL KLQEFVNKKG LLGNRNCCRG GAGPPPCACR TFFRVCLKHY QASVSPEPPC  60
TYGSAVTPVL GVDSFSLPDG GGADSAFSNP IRFPFGFTWP GTFSLIIEAL HTDSPDDLAT  120
ENPERLISRL ATQRHLTVGE EWSQDLHSSG RTDLKYSYRF VCDEHYYGEG CSVFCRPRDD  180
AFGHFTCGER GEKVCNPGWK GPYCTEPICL PGCDEQHGFC DKPGECKCRV GWQGRYCDEC  240
IRYPGCLHGT CQQPWQCNCQ EGWGGLFCNQ DLNYCTHHKP CKNGATCTNT GQGSYTCSCR  300
PGYTGATCEL GIDECDPSPC KNGGSCTDLE NSYSCTCPPG FYGKICELSA MTCADGPCFN  360
GGRCSDSPDG GYSCRCPVGY SGFNCEKKID YCSSSPCSNG AKCVDLGDAY LCRCQAGFSG  420
RHCDDNVDDC ASSPCANGGT CRDGVNDFSC TCPPGYTGRN CSAPVSRCEH APCHNGATCH  480
ERGHRYVCEC ARGYGGPNCQ FLLPELPPGP AVVDLTEKLE GQGGPFPW               528

SEQ ID NO: 20          moltype = AA  length = 618
FEATURE                Location/Qualifiers
source                 1..618
                       mol_type = protein
                       organism = Homo sapiens
SEQUENCE: 20
MVSPRMSGLL SQTVILALIF LPQTRPAGVF ELQIHSFGPG PGPGAPRSPC SARLPCRLFF  60
RVCLKPGLSE EAAESPCALG AALSARGPVY TEQPGAPAPD LPLPDGLLQV PFRDAWPGTF  120
SFIIETWREE LGDQIGGPAW SLLARVAGRR RLAAGGPWAR DIQRAGAWEL RFSYRARCEP  180
PAVGTACTRL CRPRSAPSRC GPGLRPCAPL EDECEAPLVC RAGCSPEHGF CEQPGECRCL  240
EGWTGPLCTV PVSTSSCLSP RGPSSATTGC LVPGPGPCDG NPCANGGSCS ETPRSFECTC  300
PRGFYGLRCE VSGVTCADGP CFNGGLCVGG ADPDSAYICH CPPGFQGSNC EKRVDRCSLQ  360
PCRNGGLCLD LGHALRCRCR AGFAGPRCEH DLDDCAGRAC ANGGTCVEGG GAHRCSCALG  420
FGGRDCRERA DPCAARPCAH GGRCYAHFSG LVCACAPGYM GARCEFPVHP DGASALPAAP  480
PGLRPGDPQR YLLPPALGLL VAAGVAGAAL LLVHVRRRGH SQDAGSRLLA GTPEPSVHAL  540
PDALNNLRTQ EGSGDGPSSS VDWNRPEDVD PQGIYVISAP SIYAREVATP LFPPLHTGRA  600
GQRQHLLFPY PSSILSVK                                               618
```

```
SEQ ID NO: 21          moltype = AA  length = 466
FEATURE                Location/Qualifiers
source                 1..466
                       mol_type = protein
                       organism = Homo sapiens
SEQUENCE: 21
AGVFELQIHS FGPGPGPGAP RSPCSARLPC RLFFRVCLKP GLSEEAAESP CALGAALSAR  60
GPVYTEQPGA PAPDLPLPDG LLQVPFRDAW PGTFSFIIET WREELGDQIG GPAWSLLARV  120
AGRRRLAAGG PWARDIQRAG AWELRFSYRA RCEPPAVGTA CTRLCRPRSA PSRCGPGLRP  180
CAPLEDECEA PLVCRAGCSP EHGFCEQPGE CRCLEGWTGP LCTVPVSTSS CLSPRGPSSA  240
TTGCLVPGPG PCDGNPCANG GSCSETPRSF ECTCPRGFYG LRCEVSGVTC ADGPCFNGGL  300
CVGGADPDSA YICHCPPGFQ GSNCEKRVDR CSLQPCRNGG LCLDLGHALR CRCRAGFAGP  360
RCEHDLDDCA GRACANGGTC VEGGGAHRCS CALGFGGRDC RERADPCAAR PCAHGGRCYA  420
HFSGLVCACA PGYMGARCEF PVHPDGASAL PAAPPGLRPG DPQRYL                 466

SEQ ID NO: 22          moltype = AA  length = 685
FEATURE                Location/Qualifiers
source                 1..685
                       mol_type = protein
                       organism = Homo sapiens
SEQUENCE: 22
MAAASRSASG WALLLLVALW QQRAAGSGVF QLQLQEFINE RGVLASGRPC EPGCRTFFRV  60
CLKHFQAVVS PGPCTFGTVS TPVLGTNSFA VRDDSSGGGR NPLQLPFNFT WPGTFSLIIE  120
AWHAPGDDLR PEALPPDALI SKIAIQGSLA VGQNWLLDEQ TSTLTRLRYS YRVICSDNYY  180
GDNCSRLCKK RNDHFGHYVC QPDGNLSCLP GWTGEYCQQP ICLSGCHEQN GYCSKPAECL  240
CRPGWQGRLC NECIPHNGCR HGTCSTPWQC TCDEGWGGLF CDQDLNYCTH HSPCKNGATC  300
SNSGQRSYTC TCRPGYTGVD CELELSECDS NPCRNGGSCK DQEDGYHCLC PPGYYGLHCE  360
HSTLSCADSP CFNGGSCRER NQGANYACEC PPNFTGSNCE KKVDRCTSNP CANGGQCLNR  420
GPSRMCRCRP GFTGTYCELH VSDCARNPCA HGGTCHDLEN GLMCTCPAGF SGRRCEVRTS  480
IDACASSPCF NRATCYTDLS TDTFVCNCPY GFVGSRCEFP VGLPPSFPWV AVSLGVGLAV  540
LLVLLGMVAV AVRQLRLRRP DDGSREAMNN LSDFQKDNLI PAAQLKNTNQ KKELEVDCGL  600
DKSNCGKQQN HTLDYNLAPG PLGRGTMPGK FPHSDKSLGE KAPLRLHSEK PECRISAICS  660
PRDSMYQSVC LISEERNECV IATEV                                        685

SEQ ID NO: 23          moltype = AA  length = 503
FEATURE                Location/Qualifiers
source                 1..503
                       mol_type = protein
                       organism = Homo sapiens
SEQUENCE: 23
SGVFQLQLQE FINERGVLAS GRPCEPGCRT FFRVCLKHFQ AVVSPGPCTF GTVSTPVLGT  60
NSFAVRDDSS GGGRNPLQLP FNFTWPGTFS LIIEAWHAPG DDLRPEALPP DALISKIAIQ  120
GSLAVGQNWL LDEQTSTLTR LRYSYRVICS DNYYGDNCSR LCKKRNDHFG HYVCQPDGNL  180
SCLPGWTGEY CQQPICLSGC HEQNGYCSKP AECLCRPGWQ GRLCNECIPH NGCRHGTCST  240
PWQCTCDEGW GGLFCDQDLN YCTHHSPCKN GATCSNSGQR SYTCTCRPGY TGVDCELELS  300
ECDSNPCRNG GSCKDQEDGY HCLCPPGYYG LHCEHSTLSC ADSPCFNGGS CRERNQGANY  360
ACECPPNFTG SNCEKKVDRC TSNPCANGGQ CLNRGPSRMC RCRPGFTGTY CELHVSDCAR  420
NPCAHGGTCH DLENGLMCTC PAGFSGRRCE VRTSIDACAS SPCFNRATCY TDLSTDTFVC  480
NCPYGFVGSR CEFPVGLPPS FPW                                          503

SEQ ID NO: 24          moltype = AA  length = 183
FEATURE                Location/Qualifiers
source                 1..183
                       mol_type = protein
                       organism = Homo sapiens
SEQUENCE: 24
HSHRDFQPVL HLVALNSPLS GGMRGIRGAD FQCFQQARAV GLAGTFRAFL SSRLQDLYSI  60
VRRADRAAVP IVNLKDELLF PSWEALFSGS EGPLKPGARI FSFDGKDVLR HPTWPQKSVW  120
HGSDPNGRRL TESYCETWRT EAPSATGQAS SLLGGRLLGQ SAASCHHAYI VLCIENSFMT  180
ASK                                                                183

SEQ ID NO: 25          moltype = DNA  length = 549
FEATURE                Location/Qualifiers
source                 1..549
                       mol_type = genomic DNA
                       organism = Homo sapiens
SEQUENCE: 25
cacagccacc gcgacttcca gccggtgctc cacctggttg cgctcaacag ccccctgtca  60
ggcggcatgc ggggcatccg cggggccgac ttccagtgct tccagcaggc gcgggccgtg  120
gggctggcgg gcaccttccg cgccttcctg tcctcgcgcc tgcaggacct gtacagcatc  180
gtgcgccgtg ccgaccgcgc agccgtgccc atcgtcaacc tcaaggacga gctgctgttt  240
cccagctggg aggctctgtt ctcaggctct gagggtccgc tgaagcccgg ggcacgcatc  300
ttctcctttg acggcaagga cgtcctgagg caccccacct ggccccagaa gagcgtgtgg  360
catggctcgg accccaacgg gcgcaggctg accgagagct actgtgagac gtggcggacg  420
gaggctccct cggccacggg ccaggcctcc tcgctgctgg ggggcaggct cctggggcag  480
agtgccgcga gctgccatca cgcctacatc gtgctctgca ttgagaacag cttcatgact  540
gcctccaag                                                          549
```

-continued

```
SEQ ID NO: 26          moltype = AA  length = 259
FEATURE                Location/Qualifiers
source                 1..259
                       mol_type = protein
                       organism = Homo sapiens
SEQUENCE: 26
MSEVPVARVW LVLLLLTVQV GVTAGAPWQC APCSAEKLAL CPPVSASCSE VTRSAGCGCC  60
PMCALPLGAA CGVATARCAR GLSCRALPGE QQPLHALTRG QGACVQESDA SAPHAAEAGS  120
PESPESTEIT EEELLDNFHL MAPSEEDHSI LWDAISTYDG SKALHVTNIK KWKEPCRIEL  180
YRVVESLAKA QETSGEEISK FYLPNCNKNG FYHSRQCETS MDGEAGLCWC VYPWNGKRIP  240
GSPEIRGDPN CQIYFNVQN                                                259

SEQ ID NO: 27          moltype = DNA  length = 1660
FEATURE                Location/Qualifiers
source                 1..1660
                       mol_type = genomic DNA
                       organism = Homo sapiens
SEQUENCE: 27
ggtgcactag caaaacaaac ttattttgaa cactcagctc ctagcgtgcg gcgctgccaa  60
tcattaacct cctggtgcaa gtggcgcggc ctgtgccctt tataaggtgc gcgctgtgtc  120
cagcgagcat cggccaccgc catcccatcc agcgagcatc tgccgccgcg ccgccgccac  180
cctcccagag agcactggcc accgctccac catcacttgc ccagagtttg ggccaccgcc  240
cgccgccacc agcccagaga gcatcggccc ctgtctgctg ctcgcgcctg gagatgtcag  300
aggtccccgt tgctcgcgtc tggctggtac tgctcctgct gactgtccag gtcggcgtga  360
cagccggcgc tccgtggcag tgcgcgccct gctccgccga gaagctcgcg ctctgcccgc  420
cggtgtccgc ctcgtgctcg gaggtcaccc ggtccgccgg ctgcggctgt tgcccgatgt  480
gcgccctgcc tctgggcgcc gcgtgcggcg tggcgactgc acgctgcgcc cggggactca  540
gttgccgcgc gctgccgggg gagcagcaac ctctgcacgc cctcacccgc ggccaaggcg  600
cctgcgtgca ggagtctgac gcctccgctc cccatgctgc agaggcaggg agccctgaaa  660
gcccagagag cacggagata actgaggagg agctcctgga taatttccat ctgatggccc  720
cttctgaaga ggatcattcc atcctttggg acgccatcag tacctatgat ggctcgaagg  780
ctctccatgt caccaacatc aaaaaatgga aggagccctg ccgaatagaa ctctacagag  840
tcgtagagag tttagccaag gcacaggaga catcaggaga agaaatttcc aaattttacc  900
tgccaaactg caacaagaat ggattttatc acagcagaca gtgtgagaca tccatggatg  960
gagaggcggg actctgctgg tgcgtctacc cttggaatgg gaagaggatc cctgggtctc  1020
cagagatcag gggagacccc aactgccaga tatattttaa tgtacaaaac tgaaaccaga  1080
tgaaataatg ttctgtcacg tgaaatattt aagtatatag tatatttata ctctagaaca  1140
tgcacattta tatatatatg tatatgtata tatatatagt aactactttt tatactccat  1200
acataacttg atatagaaag ctgtttattt attcactgta agtttatttt ttctacacag  1260
taaaaacttg tactatgtta ataacttgtc ctatgtcaat ttgtatatca tgaaacactt  1320
ctcatcatat tgtatgtaag taattgcatt tctgctcttc caaagctcct gcgtctgttt  1380
ttaaagagca tggaaaaata ctgcctagaa aatgcaaaat gaaataagag agagtagttt  1440
ttcagctagt ttgaaggagg acggttaact tgtatattcc accattcaca tttgatgtac  1500
atgtgtaggg aaagttaaaa gtgttgatta cataatcaaa gctacctgtg gtgatgttgc  1560
cacctgttaa aatgtacact ggatatgttg ttaaacacgt gtctataatg gaaacattta  1620
caataaatat tctgcatgga aatactgtta aaaaaaaaaa                        1660

SEQ ID NO: 28          moltype = AA  length = 480
FEATURE                Location/Qualifiers
source                 1..480
                       mol_type = protein
                       organism = Homo sapiens
SEQUENCE: 28
MQIPRAALLP LLLLLLAAPA SAQLSRAGRS APLAAGCPDR CEPARCPPQP EHCEGGRARD  60
ACGCCEVCGA PEGAACGLQE GPCGEGLQCV VPFGVPASAT VRRRAQAGLC VCASSEPVCG  120
SDANTYANLC QLRAASRRSE RLHRPPVIVL QRGACGQGQE DPNSLRHKYN FIADVVEKIA  180
PAVVHIELFR KLPFSKREVP VASGSGFIVS EDGLIVTNAH VVTNKHRVKV ELKNGATYEA  240
KIKDVDEKAD IALIKIDHQG KLPVLLLGRS SELRPGEFVV AIGSPFSLQN TVTTGIVSTT  300
QRGGKELGLR NSDMDYIQTD AIINYGNSGG PLVNLDGEVI GINTLKVTAG ISFAIPSDKI  360
KKFLTESHDR QAKGKAITKK KYIGIRMMSL TSSKAKELKD RHRDFPDVIS GAYIIEVIPD  420
TPAEAGGLKE NDVIISINGQ SVVSANDVSD VIKRESTLNM VVRRGNEDIM ITVIPEEIDP  480

SEQ ID NO: 29          moltype = AA  length = 22
FEATURE                Location/Qualifiers
source                 1..22
                       mol_type = protein
                       organism = synthetic construct
SEQUENCE: 29
MQIPRAALLP LLLLLLAAPA SA                                            22

SEQ ID NO: 30          moltype = AA  length = 161
FEATURE                Location/Qualifiers
source                 1..161
                       mol_type = protein
                       organism = synthetic construct
SEQUENCE: 30
GSGFIVSEDG LIVTNAHVVT NKHRVKVELK NGATYEAKIK DVDEKADIAL IKIDHQGKLP  60
VLLLGRSSEL RPGEFVVAIG SPFSLQNTVT TGIVSTTQRG GKELGLRNSD MDYIQTDAII  120
NYGNSGGPLV NLDGEVIGIN TLKVTAGISF AIPSDKIKKF L                       161
```

```
SEQ ID NO: 31          moltype = DNA  length = 2138
FEATURE                Location/Qualifiers
source                 1..2138
                       mol_type = genomic DNA
                       organism = Homo sapiens
SEQUENCE: 31
caatgggctg ggccgcgcgg ccgcgcgcac tcgcacccgc tgccccccgag gccctcctgc  60
actctccccg gcgccgctct ccggccctcg ccctgtccgc cgccaccgcc gccgccgcca  120
gagtcgccat gcagatcccg cgcgccgctc ttctcccgct gctgctgctg ctgctggcgg  180
cgcccgcctc ggcgcagctg tcccgggccg gccgctcggc gcctttggcc gccgggtgcc  240
cagaccgctg cgagccggcg cgctgcccgc cgcagccgga gcactgcgag ggcggccggg  300
cccgggacgc gtgcggctgc tgcgaggtgt gcggcgcgcc cgagggcgcc gcgtgcggcc  360
tgcaggaggg cccgtgcggc gaggggctgc agtgcgtggt gcccttcggg gtgccagcct  420
cggccacggt gcggcggcgc gcgcaggccg gcctctgtgt gtgcgccagc agcgagccgg  480
tgtgcggcag cgacgccaac acctacgcca acctgtgcca gctgcgcgcc gccagccgcc  540
gctccgagag gctgcaccgg ccgccggtca tcgtcctgca gcgcggagcc tgcggccaag  600
ggcaggaaga tcccaacagt ttgcgccata aatataactt tatcgcggac gtggtggaga  660
agatcgcccc tgccgtggtt catatcgaat tgtttcgcaa gcttccgttt tctaaacgag  720
aggtgccggt ggctagtggg tctgggttta ttgtgtcgga agatggactg atcgtgacaa  780
atgcccacgt ggtgaccaac aagcaccggg tcaaagttga gctgaagaac ggtgccactt  840
acgaagccaa aatcaaggat gtggatgaga aagcagacat cgcactcatc aaaattgacc  900
accagggcaa gctgcctgtc ctgctgcttg gccgctcctc agagctgcgg ccgggagagt  960
tcgtggtcgc catcggaagc ccgttttccc ttcaaaacac agtcaccacc gggatcgtga  1020
gcaccaccca gcgaggcggc aaagagctgg ggctccgcaa ctcagacatg gactacatcc  1080
agaccgacgc catcatcaac tatggaaact cgggaggccc gttagtaaac ctggacggtg  1140
aagtgattgg aattaacact ttgaaagtga cagctggaat ctcctttgca atcccatctg  1200
ataagattaa aaagttcctc acggagtccc atgaccgaca ggccaaagga aaagccatca  1260
ccaagaagaa gtatattggt atccgaatga tgtcactcac gtccagcaaa gccaaagagc  1320
tgaaggaccg gcaccgggac ttcccagacg tgatctcagg agcgtatata attgaagtaa  1380
ttcctgatac cccagcagaa gctggtggtc tcaaggaaaa cgacgtcata atcagcatca  1440
atggacagtc cgtggtctcc gccaatgatg tcagcgacgt cattaaaagg gaaagcaccc  1500
tgaacatggt ggtccgcagg ggtaatgaag atatcatgat cacagtgatt cccgaagaaa  1560
ttgacccata ggcagaggca tgagctggac ttcatgtttc cctcaaagac tctcccgtgg  1620
atgacggatg aggactctgg gctgctggaa taggacactc aagacttttg actgccattt  1680
tgtttgttca gtggagactc cctggccaac agaatccttc ttgatagttt gcaggcaaaa  1740
caaatgtaat gttgcagatc cgcaggcaga agctctgccc ttctgtatcc tatgtatgca  1800
gtgtgctttt tcttgccagc ttgggccatt cttgcttaga cagtcagcat ttgtctcctc  1860
ctttaactga gtcatcatct tagtccaact aatgcagtcg atacaatgcg tagatagaag  1920
aagccccacg ggagccagga tgggactggt cgtgtttgtg cttttctcca agtcagcacc  1980
caaaggtcaa tgcacagaga ccccgggtgg gtgagcgctg gcttctcaaa cggccgaagt  2040
tgcctctttt aggaatctct ttggaattgg gagcacgatg actctgagtt tgagctatta  2100
aagtacttct tacacattgc aaaaaaaaaa aaaaaaaa                        2138

SEQ ID NO: 32          moltype = DNA  length = 8089
FEATURE                Location/Qualifiers
source                 1..8089
                       mol_type = genomic DNA
                       organism = Homo sapiens
SEQUENCE: 32
gcggcgcgga ggctggcccg ggacgcgccc ggagcccagg gaaggaggga ggaggggagg  60
gtcgcggccg gccgccatgg ggccgggggc ccgtggccgc cgccgccgcc gtcgcccgat  120
gtcgccgcca ccgccaccgc cacccgtgcg ggcgctgccc ctgctgctgc tgctagcggg  180
gccgggggct gcagcccccc cttgcctgga cggaagcccg tgtgcaaatg gaggtcgttg  240
cacccagctg ccctcccggg aggctgcctg cctgtgcccg cctggctggg tgggtgagcg  300
gtgtcagctg gaggacccct gtcactcagg cccctgtgct ggccgtggtg tctgccagag  360
ttcagtggtg gctggcaccg cccgattctc atgccggtgc ccccgtggct tccgaggccc  420
tgactgctcc ctgccagatc cctgcctcag cagcccttgt gcccacggtg cccgctgctc  480
agtggggccc gatggacgct tcctctgctc ctgcccacct ggctaccagg gccgcagctg  540
ccgaagcgac gtggatgagt gccgggtggg tgagccctgc cgccatggtg gcacctgcct  600
caacacacct ggctccttcc gctgccagtg tccagctggc tacacagggc cactatgtga  660
gaaccccgcg gtgccctgtg caccctcacc atgccgtaac gggggcacct gcaggcagag  720
tggcgacctc acttacgact gtgcctgtct tcctgggttt gagggtcaga attgtgaagt  780
gaacgtggac gactgtccag gacaccgatg tctcaatggg gggacatgcg tggatggcgt  840
caacacctat aactgccagt gccctcctga gtggacaggc cagttctgca cggaggacgt  900
ggatgagtgt cagctgcagc ccaacgcctg ccacaatggg ggtacctgct tcaacacgct  960
gggtggccac agctgcgtgt gtgtcaatgg ctggacaggc gagagctgca gtcagaatat  1020
cgatgactgt gccacagccg tgtgcttcca tggggccacc tgccatgacc gcgtggcttc  1080
tttctactgt gcctgcccca tgggcaagac tggcctcctg tgtcacctgg atgacgcctg  1140
tgtcagcaac ccctgccacg aggatgctat ctgtgacaca aatccggtga acggccgggc  1200
catttgcacc tgtcctcccg gcttcacggg tggggcatgt gaccaggatg tggacgagtg  1260
ctctatcggc gccaacccct gcgagcactt gggcaggtgc gtgaacacgc agggctcctt  1320
cctgtgccag tgcggtcgtg gctacactgg acctcgctgt gagaccgatg tcaacgagtg  1380
tctgtcgggg ccctgccgaa accaggccac gtgcctcgac cgcataggcc agttcacctg  1440
tatctgtatg gcaggcttca caggaaccta ttgcgaggtg gacattgacg agtgtcagag  1500
tagcccctgt gtcaacggtg gggtctgcaa ggaccgagtc aatggcttca gctgcacctg  1560
cccctcgggc ttcagcggct ccacgtgtca gctggacgtg gacgaatgcg ccagcacgcc  1620
ctgcaggaat ggcgccaaat gcgtggacca gcccgatggc tacgagtgcc gctgtgccga  1680
gggctttgag ggcacgctgt gtgatcgcaa cgtggacgac tgctcccctg acccatgcca  1740
```

-continued

```
ccatggtcgc tgcgtggatg gcatcgccag cttctcatgt gcctgtgctc ctggctacac  1800
gggcacacgc tgcgagagcc aggtggacga atgccgcagc cagccctgcc gccatggcgg  1860
caaatgccta gacctggtgg acaagtacct ctgccgctgc ccttctggga ccacaggtgt  1920
gaactgcgaa gtgaacattg acgactgtgc cagcaacccc tgcacctttg gagtctgccg  1980
tgatggcatc aaccgctacg actgtgtctg ccaacctggc ttcacagggc cccctttgtaa  2040
cgtggagatc aatgagtgtg cttccagccc atgcggcgag ggaggttcct gtgtggatgg  2100
ggaaaatggc ttccgctgcc tctgcccgcc tggctccttg cccccactct gcctcccccc  2160
gagccatccc tgtgcccatg agccctgcag tcacggcatc tgctatgatg cacctggcgg  2220
gttccgctgt gtgtgtgagc ctggctggag tggcccccgc tgcagccaga gcctggcccg  2280
agacgcctgt gagtcccagc cgtgcagggc cggtgggaca tgcagcagcg atggaatggg  2340
tttccactgc acctgcccgc ctggtgtcca gggacgtcag tgtgaactcc tctcccccctg  2400
caccccgaac ccctgtgagc atgggggccg ctgcgagtct gcccctggcc agctgcctgt  2460
ctgctcctgc ccccagggct ggcaaggccc acgatgccag caggatgtgg acgagtgtgc  2520
tggccccgca ccctgtggcc ctcatggtat ctgcaccaac ctggcaggga gtttcagctg  2580
cacctgccat ggagggtaca ctggcccttc ctgcgatcag gacatcaatg actgtgaccc  2640
caacccatgc ctgaacggtg gctcgtgcca agacggcgtg ggctcctttt cctgctcctg  2700
cctccctggt ttcgccggcc cacgatgcgc ccgcgatgtg gatgagtgcc tgagcaaccc  2760
ctgcggcccg ggcacctgta ccgaccacgt ggcctccttc acctgcacct gcccgccagg  2820
ctacggaggc ttccactgcg aacaggacct gcccgactgc agccccagct cctgcttcaa  2880
tggcgggacc tgtgtggacg gcgtgaactc gttcagctgc ctgtgccgtc ccggctacac  2940
aggagcccac tgccaacatg aggcagaccc ctgcctctcg cggccctgcc tacacggggg  3000
cgtctgcagc gccgcccacc ctggcttccg ctgcacctgc ctcgagagct tcacgggccc  3060
gcagtgccag acgctggtgg attggtgcag ccgccagcct tgtcaaaacg gggtcgctg  3120
cgtccagact ggggcctatt gcctttgtcc ccctggatgg agcggacgcc tctgtgacat  3180
ccgaagcttg ccctgcaggg aggccgcagc ccagatcggg gtgcggctgg agcagctgtg  3240
tcaggcgggt gggcagtgtg tggatgaaga cagctcccac tactgcgtgt gcccagaggg  3300
ccgtactggt agccactgtg agcaggaggt ggacccctgc ttggcccagc cctgccagca  3360
tgggggggacc tgccgtggct atatgggggg ctacatgtgt gagtgtcttc ctggctacaa  3420
tggtgataac tgtgaggacg acgtggacga gtgtgcctcc cagccctgcc agcacggggg  3480
ttcatgcatt gacctcgtgg cccgctatct ctgctcctgt cccccaggaa cgctgggggt  3540
gctctgcgag attaatgagg atgactgcgg cccaggccca ccgctggact cagggccccg  3600
gtgcctacac aatggcacct gcgtggacct ggtgggtggt ttccgctgca cctgtccccc  3660
aggatacact ggtttgcgct gcgaggcaga catcaatgag tgtcgctcag gtgcctgcca  3720
cgcggcacac acccgggact gcctgcagga cccaggcgga ggtttccgtt gcctttgtca  3780
tgctggcttc tcaggtcctc gctgtcagac tgtcctgtct ccctgcgagt cccagccatg  3840
ccagcatgga ggccagtgcc gtcctagccc gggtcctggg ggtgggctga ccttcacctg  3900
tcactgtgcc cagccgttct ggggtccgcg ttgcgagcgg gtggcgcgct cctgccggga  3960
gctgcagtgc ccggtgggcg tcccatgcca gcagacgccc cgcgggccgc gctgcgcctg  4020
ccccccaggg ttgtcgggac cctcctgccg cagcttcccg gggtcgccgc cgggggccag  4080
caacgccagc tgcgcggccg cccccgtgtct ccacgggggc tcctgcgccc ccgcgccgct  4140
cgcgcccttc ttccgctgcg cttgcgcgca gggctggacc gggccgcgct gcgaggcgcc  4200
cgccgcggca cccgaggtct cggaggagcc gcggtgcccg cgcgccgcct gccaggccaa  4260
gcgcggggac cagcgctgcg accgcgagtg caacagccca ggctgcggct gggacggcgg  4320
cgactgctcg ctgagcgtgg gcgacccctg gcggcaatgc gaggcgctgc agtgctggcg  4380
cctcttcaac aacagccgct gcgaccccgc ctgcagctcg cccgcctgcc tctacgacaa  4440
cttcgactgc cacgccggtg gccgcgagcg cacttgcaac ccggtgtacg agaagtactg  4500
cgccgaccac tttgccgacg gccgctgcga ccagggctgc aacacggagg agtgcggctg  4560
ggatgggctg gattgtgcca gcgaggtgcc ggccctgctg gcccgcggcg tgctggtgct  4620
cacagtgctg ctgccgccag aggagctact gcgttccagc gccgactttc tgcagcggct  4680
cagcgccatc ctgcgcacct cgctgcgctt ccgcctggac gcgcacggcc aggccatggt  4740
cttcccttac caccggccta gtcctggctc cgaacccccgg gcccgtcggg agctggcccc  4800
cgaggtgatc ggctcggtag taatgctgga gattgacaac cggctctgcc tgcagtcgcc  4860
tgagaatgat cactgcttcc ccgatgccca gagcgccgct gactacctgg gagcgttgtc  4920
agcggtggag cgcctggact tcccgtaccc actgcgggac gtgcgggggg agccgctgga  4980
gcctccagaa cccagcgtcc cgctgctgcc actgctagtg gcgggcgctg tcttgctgct  5040
ggtcattctc gtcctgggtg tcatggtggc ccggcgcaag cgcgagcaca gcaccctctg  5100
gttccctgag ggcttctcac tgcacaagga cgtggcctct ggtcacaagg gccggcggga  5160
acccgtgggc caggacgcgc tgggcatgaa gaacatggcc aagggtgaga gcctgatggg  5220
ggaggtggcc acagactgga tggacacaga gtgcccagag gccaagcggc taaaggtaga  5280
ggagccaggc atgggggctg aggaggctgt ggattgccgt cagtggactc aacaccatct  5340
ggttgctgct gacatccgcg tggcaccagc catggcactg acaccaccac agggcgacgc  5400
agatgctgat ggcatggatg tcaatgtgcg tggcccagat ggcttcaccc cgctaatgct  5460
ggcttccttc tgtggggggg ctctggagcc aatgccaact gaagaggatg aggcagatga  5520
cacatcagct agcatcatct ccgacctgat ctgccagggg gctcagcttg gggcacggac  5580
tgaccgtact ggcgagactg ctttgcacct ggctgcccgt tatgcccgtg ctgatgcagc  5640
caagcggctg ctggatgctg gggcagacac caatgcccag gaccactcag gccgcactcc  5700
cctgcacaca gctgtcacag ccgatgccca gggtgtcttc cagattctca tccgaaaccg  5760
ctctacagac ttggatgccc gcatggcaga tggctcaacg gcactgatcc tggcggcccg  5820
cctggcagta gagggcatgg tggaagagct catcgccagc catgctgatg tcaatgctgt  5880
ggatgagctt gggaaatcag ccttacactg ggctgcggct gtgaacaacg tggaagccac  5940
tttggccctg ctcaaaaatg gagccaataa ggacatgcag gatagcaagg aggagaccccc  6000
cctattcctg gccgcccgcg agggcagcta tgaggctgcc aagctgctgt tggaccactt  6060
tgccaaccgt gagatcaccg accacctgga caggctgccg cgggacgtag cccaggagag  6120
actgcaccag gacatcgtgc gcttgctgga tcaacccagt gggccccgca gcccccccgg  6180
tccccacggc ctggggcctc tgctctgtcc tccaggggcc ttcctccctg gcctcaaagc  6240
ggcacagtcg gggtccaaga agagcaggag gcccccggg aaggcggggc tggggccgca  6300
ggggccccgg gggcggggca agaagctgac gctggcctgc ccgggccccc tggctgacag  6360
ctcggtcacg ctgtcgcccg tggactcgct ggactccccg cggcctttcg gtggcccccc  6420
tgcttcccct ggtggcttcc cccttgaggg gccctatgca gctgccactg ccactgcagt  6480
```

-continued

```
gtctctggca cagcttggtg gcccaggccg ggcgggtcta gggcgccagc cccctggagg  6540
atgtgtactc agcctgggcc tgctgaaccc tgtggctgtg cccctcgatt gggcccggct  6600
gcccccacct gcccctccag gcccctcgtt cctgctgcca ctggcgccgg gaccccagct  6660
gctcaaccca gggacccccg tctccccgca ggagcggccc ccgccttacc tggcagtccc  6720
aggacatggc gaggagtacc cggcggctgg ggcacacagc agccccccaa aggcccgctt  6780
cctgcgggtt cccagtgagc acccttacct gaccccatcc cccgaatccc ctgagcactg  6840
ggccagcccc tcacctccct ccctctcaga ctggtccgaa tccacgccta gcccagccac  6900
tgccactggg gccatggcca ccaccactgg ggcactgcct gcccagccac ttcccttgtc  6960
tgttcccagc tcccttgctc aggcccagac ccagctgggg ccccagccgg aagttacccc  7020
caagaggcaa gtgttggcct gagacgctcg tcagttctta gatcttgggg gcctaaagag  7080
acccccgtcc tgcctccttt ctttctctgt ctcttccttc cttttagtct ttttcatcct  7140
cttctctttc caccaaccct cctgcatcct tgccttgcag cgtgaccgag ataggtcatc  7200
agcccagggc ttcagtcttc ctttatttat aatgggtggg ggctaccacc caccctctca  7260
gtcttgtgaa gagtctggga cctccttctt ccccacttct ctcttccctc attcctttct  7320
ctctccttct ggcctctcat ttccttacac tctgacatga atgaattatt attattttta  7380
tttttctttt ttttttaca ttttgtatag aaacaaattc atttaaacaa acttattatt  7440
attatttttt acaaaatata tatatggaga tgctccctcc ccctgtgaac cccccagtgc  7500
ccccgtgggg ctgagtctgt gggcccattc ggccaagctg gattctgtgt acctagtaca  7560
caggcatgac tgggatcccg tgtaccgagt acacgaccca ggtatgtacc aagtaggcac  7620
ccttgggcgc acccactggg gccaggggtc gggggagtgt tgggagcctc ctccccaccc  7680
cacctccctc acttcactgc attccagatg ggacatgttc catagccttg ctggggaagg  7740
gccccactgcc aactccctct gccccagccc cacccttggc catctccctt tgggaactag  7800
ggggctgctg gtgggaaatg ggagccaggg cagatgtatg cattcctttg tgtccctgta  7860
aatgtgggac tacaagaaga ggagctgcct gagtggtact ttctcttcct ggtaatcctc  7920
tggcccagcc tcatggcaga atagaggtat ttttaggcta tttttgtaat atggcttctg  7980
gtcaaaatcc ctgtgtagct gaattcccaa gccctgcatt gtacagcccc ccactcccct  8040
caccacctaa taaaggaata gttaacactc aaaaaaaaaa aaaaaaaaa             8089

SEQ ID NO: 33          moltype = AA  length = 2321
FEATURE                Location/Qualifiers
source                 1..2321
                       mol_type = protein
                       organism = Homo sapiens
SEQUENCE: 33
MGPGARGRRR RRRPMSPPPP PPPVRALPLL LLLAGPGAAA PPCLDGSPCA NGGRCTQLPS  60
REAACLCPPG WVGERCQLED PCHSGPCAGR GVCQSSVVAG TARFSCRCPR GFRGPDCSLP  120
DPCLSSPCAH GARCSVGPDG RFLCSCPPGY QGRSCRSDVD ECRVGEPCRH GGTCLNTPGS  180
FRCQCPAGYT GPLCENPAVP CAPSPCRNGG TCRQSGDLTY DCACLPGFEG QNCEVNVDDC  240
PGHRCLNGGT CVDGVNTYNC QCPPEWTGQF CTEDVDECQL QPNACHNGGT CFNTLGGHSC  300
VCVNGWTGES CSQNIDDCAT AVCFHGATCH DRVASFYCAC PMGKTGLLCH LDDACVSNPC  360
HEDAICDTNP VNGRAICTCP PGFTGGACDQ DVDECSIGAN PCEHLGRCVN TQGSFLCQCG  420
RGYTGPRCET DVNECLSGPC RNQATCLDRI GQFTCICMAG FTGTYCEVDI DECQSSPCVN  480
GGVCKDRVNG FSCTCPSGFS GSTCQLDVDE CASTPCRNGA KCVDQPDGYE CRCAEGFEGT  540
LCDRNVDDCS PDPCHHGRCV DGIASFSCAC APGYTGTRCE SQVDECRSQP CRHGGKCLDL  600
VDKYLCRCPS GTTGVNCEVN IDDCASNPCT FGVCRDGINR YDCVCQPGFT GPLCNVEINE  660
CASSPCGEGG SCVDGENGFR CLCPPGSLPP LCLPPSHPCA HEPCSHGICY DAPGGFRCVC  720
EPGWSGPRCS QSLARDACES QPCRAGGTCS SDGMGFHCTC PPGVQGRQCE LLSPCTPNPC  780
EHGGRCESAP GQLPVCSCPQ GWQGPRCQQD VDECAGPAPC GPHGICTNLA GSFSCTCHGG  840
YTGPSCDQDI NDCDPNPCLN GGSCQDGVGS FSCSCLPGFA GPRCARDVDE CLSNPCGPGT  900
CTDHVASFTC TCPPGYGGFH CEQDLPDCSP SSCFNGGTCV DGVNSFSCLC RPGYTGAHCQ  960
HEADPCLSRP CLHGGVCSAA HPGFRCTCLE SFTGPQCQTL VDWCSRQPCQ NGGRCVQTGA  1020
YCLCPPGWSG RLCDIRSLPC REAAAQIGVR LEQLCQAGGQ CVDEDSSHYC VCPEGRTGSH  1080
CEQEVDPCLA QPCQHGGTCR GYMGGYMCEC LPGYNGDNCE DDVDECASQP CQHGGSCIDL  1140
VARYLCSCPP GTLGVLCEIN EDDCGPGPPL DSGPRCLHNG TCVDLVGGFR CTCPPGYTGL  1200
RCEADINECR SGACHAAHTR DCLQDPGGGF RCLCHAGFSG PRCQTVLSPC ESQPCQHGGQ  1260
CRPSPGPGGG LTFTCHCAQP FWGPRCERVA RSCRELQCPV GVPCQQTPRG PRCACPPGLS  1320
GPSCRSFPGS PPGASNASCA AAPCLHGGSC RPAPLAPFFR CACAQGWTGP RCEAPAAAPE  1380
VSEEPRCPRA ACQAKRGDQR CDRECNSPGC GWDGGDCSLS VGDPWRQCEA LQCWRLFNNS  1440
RCDPACSSPA CLYDNFDCHA GGRERTCNPV YEKYCADHFA DGRCDQGCNT EECGWDGLDC  1500
ASEVPALLAR GVLVLTVLLP PEELLRSSAD FLQRLSAILR TSLRFRLDAH GQAMVFPYHR  1560
PSPGSEPRAR RELAPEVIGS VVMLEIDNRL CLQSPENDHC FPDAQSAADY LGALSAVERL  1620
DFPYPLRDVR GEPLEPPEPS VPLLPLLVAG AVLLLVILVL GVMVARRKRE HSTLWFPEGF  1680
SLHKDVASGH KGRREPVGQD ALGMKNMAKG ESLMGEVATD WMDTECPEAK RLKVEEPGMG  1740
AEEAVDCRQW TQHHLVAADI RVAPAMALTP PQGDADADGM DVNVRGPDGF TPLMLASFCG  1800
GALEPMPTEE DEADDTSASI ISDLICQGAQ LGARTDRTGE TALHLAARYA RADAAKRLLD  1860
AGADTNAQDH SGRTPLHTAV TADAQGVFQI LIRNRSTDLD ARMADGSTAL ILAARLAVEG  1920
MVEELIASHA DVNAVDELGK SALHWAAAVN NVEATLALLK NGANKDMQDS KEETPLFLAA  1980
REGSYEAAKL LLDHFANREI TDHLDRLPRD VAQERLHQDI VRLLDQPSGP RSPPGPHGLG  2040
PLLCPPGAFL PGLKAAQSGS KKSRRPPGKA GLGPQGPRGR GKKLTLACPG PLADSSVTLS  2100
PVDSLDSPRP FGGPPASPGG FPLEGPYAAA TATAVSLAQL GGPGRAGLGR QPPGGCVLSL  2160
GLLNPVAVPL DWARLPPPAP PGPSFLLPLA PGPQLLNPGT PVSPQERPPP YLAVPGHGEE  2220
YPVAGAHSSP PKARFLRVPS EHPYLTPSPE SPEHWASPSP PSLSDWSEST PSPATATGAM  2280
ATTTGALPAQ PLPLSVPSSL AQAQTQLGPQ PEVTPKRQVL A                     2321
```

NOTCH3 AGONIST COMPOSITIONS AND METHODS FOR TREATING SMALL VESSEL DISEASES

RELATED APPLICATIONS

This application is a continuation of U.S. patent application Ser. No. 16/499,225, filed Sep. 27, 2019, which is a national stage application filed under 35 U.S.C. § 371, of International Patent Application No. PCT/US2018/024397, filed Mar. 26, 2018, which claims the benefit of and priority to U.S. Provisional Patent Application No. 62/477,289, filed Mar. 27, 2017, the entire contents of which are incorporated herein by reference.

STATEMENT AS TO FEDERALLY SPONSORED RESEARCH

This invention was made with government support under EY021624 and NS100121 awarded by the National Institutes of Health. The government has certain rights in the invention.

FIELD OF THE INVENTION

The present invention relates to small vessel diseases.

SEQUENCE LISTING

Incorporated by reference in its entirety is a computer-readable nucleotide/amino acid sequence listing submitted concurrently herewith and identified as follows: 66,813 byte xml file name "00633-0308002_SL_ST26.xml" created on Oct. 16, 2025.

BACKGROUND

Cerebral small vessel disease (SVD) is characterized by progressive degeneration of the small penetrating arteries and arterioles of the brain (Rosenberg et al., 2015, *J Cereb Blood Flow Metab*). Pathological changes in the small vessels include mural cell loss, thickening of basement membranes, and accumulation of deposits in vessel walls (Iadecola, 2013, *Neuron* 80:844-866; Rosenberg et al., 2015, *J Cereb Blood Flow Metab*). SVD is responsible for the vast majority of silent brain infarcts, is the most common cause of vascular cognitive impairment and vascular dementia, and is a major risk factor for clinically overt stroke (Hakim, 2014, *Nature* 510:S12; Iadecola, 2013, *Neuron* 80:844-866; Thompson and Hakim, 2009, *Stroke* 40:e322-330). There is increasing evidence that SVD exacerbates Alzheimer's disease pathology and vice versa; indeed, it is now clear that the most common etiology of dementia in older people includes a mixture of vascular (particularly small vessel) disease and Alzheimer's pathology (Snyder et al., 2015, *Alzheimers Dement* 11:710-717). SVD is accelerated and exacerbated by cardiovascular risk factors, including high blood pressure and diabetes, but one of the strongest risk factors for SVD is age (Iadecola, 2013, *Neuron* 80:844-866). Currently, SVD is treated via modification of cardiovascular risk factors without addressing vascular degeneration directly.

New compositions and methods for the treatment of SVDs are needed.

SUMMARY OF THE INVENTION

Provided herein are, inter alia, compositions, formulations, and methods for inhibiting, treating, preventing, and/ or reducing the symptoms of severity of SVDs. Aspects of the present subject matter relate to the use of NOTCH3 agonists for the treatment of a wide variety of SVDs including but not limited to cerebral small vessel disease, cerebral autosomal recessive arteriopathy with subcortical infarcts and leukoencephalopathy (CARASIL), age-related macular degeneration (AMD), cerebral autosomal-dominant arteriopathy with subcortical infarcts and leukoencephalopathy (CADASIL), NOTCH3 loss-of-function-associated SVD (e.g., a SVD associated with a mutation that reduces the expression and/or activity of NOTCH3), nephropathy, microangiopathy, heart failure, Alagille syndrome, familial tetralogy of Fallot, patent ductus arteriosus, cerebral cavernous malformation, and diabetic retinopathy.

Included herein is a method for treating or preventing a SVD in a subject. The method comprises administering to the subject an effective amount of a Neurogenic Locus Notch Homolog Protein 3 (NOTCH3) agonist such as an antibody that binds to the ectodomain (e.g., SEQ ID NO: 12). Such an antibody targets the extracellular domain and activates the receptor. In various embodiments, the SVD comprises cerebral SVD. In some embodiments, SVD comprises CADASIL. In certain embodiments, the SVD comprises CARASIL. In some embodiments, the SVD comprises diabetic retinopathy. In various embodiments, the SVD comprises a cerebral SVD, CARASIL, CADASIL, age-related macular degeneration (AMD), retinopathy, nephropathy or another SVD of the kidney, microangiopathy, proximal 19p13.12 microdeletion syndrome, myocardial ischemia, heart failure, NOTCH3 loss of function-associated SVD, Alagille syndrome, familial tetralogy of Fallot, patent ductus arteriosus, a cerebral cavernous malformation, or a HTRA1-associated small vessel disease.

Aspects provide methods of administering a NOTCH3 agonist to a person who has or is at risk of suffering from a SVD. In some embodiments, a subject who has or is at risk of suffering from a SVD has at least 1, 2, 3, or 4 grandparents, parents, aunts, uncles, cousins, or siblings who have the SVD. In various embodiments, the subject has diabetes (e.g., type 1 diabetes or type 2 diabetes). In certain embodiments, the subject is at least about 10, 20, 30, 40, 50, 60, 70, 80, or 90 years old. In some embodiments, the subject has Alzheimer's disease. In certain embodiments, the subject has dementia. In various embodiments, the subject has arterial hypertension.

In some embodiments, the subject comprises granular osmiophilic material (GOM) deposits. In certain embodiments, the subject does not comprise GOM deposits.

In certain embodiments, the lower the level of NOTCH3 activity is, the higher the dose of a NOTCH3 agonist is. In various embodiments, the lower the level of NOTCH3 protein or mRNA is, the higher the dose of a NOTCH3 agonist is.

In various embodiments, a subject who has or is at risk of suffering from a SVD has an abnormal level of NOTCH3, collagen18α1 or endostatin, insulin growth factor binding protein 1 (IGFBP-1), and/or High-Temperature Requirement A Serine Peptidase 1 (HTRA1) protein or mRNA. In some embodiments, a test sample obtained from the subject comprises a level of NOTCH3 protein or mRNA that is different than a normal control. For example, the test sample may comprise a level of NOTCH3 and/or collagen18α1 or endostatin protein or mRNA that is at least about 5%, 10%, 15%, 20%, 25%, 30%, 40%, 45%, 50%, 55%, 60%, 65%, 70%, 75%, 80%, 90%, 95%, 99%, 100%, 5-50%, 50-75%, or 75-100% lower in the test sample compared to a normal control. In some embodiments, the test sample comprises a level of collagen18α1 or endostatin and/or HTRA1 and/or IGFBP-1 protein or mRNA that is at least about 5%, 10%, 15%, 20%, 25%, 30%, 40%, 45%, 50%, 55%, 60%, 65%, 70%, 75%, 80%, 90%, 5-50%, 50-75%, 1-fold, 2-fold, 3-fold, 4-fold, or 5-fold higher in the test sample compared to a normal control. In certain embodiments, a test sample comprises a level of HTRA1 protein or mRNA that is at least about 5%, 10%, 15%, 20%, 25%, 30%, 40%, 45%, 50%, 55%, 60%, 65%, 70%, 75%, 80%, 90%, 95%, 99%, 100%, 5-50%, 50-75%, or 75-100% higher in the test sample compared to a normal control. In certain embodiments, a test sample comprises a level of HTRA1 protein or mRNA that is at least about 5%, 10%, 15%, 20%, 25%, 30%, 40%, 45%, 50%, 55%, 60%, 65%, 70%, 75%, 80%, 90%, 95%, 99%, 100%, 5-50%, 50-75%, or 75-100% lower in the test sample compared to a normal control. In some embodiments, the subject (e.g., a test sample from the subject) comprises a level of NOTCH3 protein bound to collagen18α1 and/or endostatin and/or HTRA1 and/or IGFBP-1 that is different than a normal control. For example, the test sample may comprise levels of NOTCH3 protein bound to collagen18α1 and/or endostatin and/or HTRA1 and/or IGFBP-1 that is at least about 5%, 10%, 15%, 20%, 25%, 30%, 40%, 45%, 50%, 55%, 60%, 65%, 70%, 75%, 80%, 90%, 5-50%, 50-75%, 1-fold, 2-fold, 3-fold, 4-fold, or 5-fold higher in the test sample compared to a normal control. Non-limiting examples of test samples include blood, serum, plasma, saliva, tears, vitreous, cerebrospinal fluid, sweat, cerebrospinal fluid, or urine.

In various embodiments, a test sample comprises a level of HTRA1 protein or mRNA that is at least about 5%, 10%, 15%, 20%, 25%, 30%, 40%, 45%, 50%, 55%, 60%, 65%, 70%, 75%, 80%, 90%, 95%, 99%, 100%, 5-50%, 50-75%, or 75-100% higher in the test sample compared to a normal control. In some embodiments, the subject has or is at risk of suffering from CADASIL.

In various embodiments, a test sample comprises a level of HTRA1 protein or mRNA that is at least about 5%, 10%, 15%, 20%, 25%, 30%, 40%, 45%, 50%, 55%, 60%, 65%, 70%, 75%, 80%, 90%, 95%, 99%, 100%, 5-50%, 50-75%, or 75-100% lower in the test sample compared to a normal control. In some embodiments, the subject has or is at risk of suffering from CARASIL.

In certain embodiments, an agonist is administered to a subject with an SVD until one or more biomarkers (e.g., NOTCH3 such as the extracellular domain thereof, a mutant thereof, or the wilt-type version thereof; GFBP-1; HTRA1; and/or collagen18α1/endostatin) reaches a level observed in a corresponding subject who does not have the SVD. In certain embodiments, the dose of the agonist is increased until one or more biomarkers (e.g., NOTCH3 such as the extracellular domain thereof, a mutant thereof, or the wilt-type version thereof; GFBP-1; HTRA1; and/or collagen18α1/endostatin) reaches a level observed in a corresponding subject who does not have the SVD.

In certain embodiments, the subject expresses NOTCH3 with any of the following CADASIL mutations: C43G, C49F, C49Y, R54C, S60C, C65S, C67Y, W71C, C76R, C76W, 77-82del, 80-84del, C87R, C87Y, R90C, C93F, C93Y, C106W, C108W, C108Y, R110C, 114-120del, C117F, S118C, C123F, C123Y, C128Y, R133C, C134W, R141C, F142C, C144S, C144Y, S145C, C146R, G149C, Y150C, 153-155del, R153C, C155S, C162S, R169C, G171C, C174F, C174R, C174Y, S180C, R182C, C183F, C183R, C183S, C185G, C185R, Y189C, C194F, C194R, C194S, C194Y, C201Y, C206Y, R207C, C212S, R213K, C222G, C222Y, C224Y, C233S, C233Y, 239-253del, C240S, C245R, C251R, Y258C, C260Y, C311G, A319C, R332C, S335C, Y337C, C349S, C379S, C395R, G420C, R421C, C428S, C428Y, C440G, C440R, C446S, R449C, C455R, C484F, C484Y, C495Y, C511R, C542Y, R544C, C549Y, R558C, R578C, R587C, R607C, C608Y, C624S, R635C, R640C, R717C, Y710C, R728C, C775S, G942C, R951C, G953C, F984C, R985C, R1006C, C1015R, Y1021C, R1031C, R1143C, D1063C, R1190C, R1201C, C1202S, R1210C, C1222G, R1231C, R1242C, C1261R, and C1261Y. In certain embodiments, the subject expresses NOTCH3 with a mutation that results in an extracellular domain of NOTCH3 having an odd number of cysteines according to the formula CnX or XnC where C stands for cysteine, n for an amino acid number in the NOTCH3 extracellular domain and X any amino replacing cysteine (for CnX) or replaced by cysteine (for XnC). In certain embodiments, n is the amino acid number (i.e., position) of any amino acid in the extracellular domain of NOTCH3. In certain embodiments, n is any one of positions 40-1643 of SEQ ID NO: 10. In certain embodiments, n is any one of positions 40-100, 100-250, 250-500, 500-750, 750-1000, 1000-1250, 1250-1500, or 1500-1643 of SEQ ID NO: 10. In certain embodiments, the subject express NOTCH3 with cysteine-sparing mutations either of the following: R61W, R75P, D80G 88-91del. See, e.g., Wollenweber et al., (2015) Cysteine-sparing CADASIL mutations in NOTCH3 show proaggregatory properties in vitro. Stroke 46(3):786-92, the entire content of which is incorporated herein by reference. In certain embodiments, the subject carries loss of function mutations in NOTCH 3 including frame shift, premature stop codon, out of frame insertions or deletions, or splicing mutations including any of the following mutations: p.R113Ter, p.R103Ter, p.R156Ter, p.Y220Ter, c.1951+2delT, p.C729Ter, p.R735Ter, p.C966Ter, p.G2035RfsTer60, p.T1816ITer3, c.2566+1G>C, p.C1110Ter, p.E1125Ter, p.Yl453Ter, p.R1851VfsTer60, c.5667+1G>A, p.R1893Ter, c.5914-2_5914-linsT, p.G2035RfsTer60, p.G2035VfsTer50. See, e.g., Pippucci et al., (2015) Homozygous NOTCH3 null mutation and impaired NOTCH3 signaling in recessive early-onset arteriopathy and cavitating leukoencephalopathy. EMBO Mol Med. 7(6):848-58; Moccia et al., (2015) Hypomorphic NOTCH3 mutation in an Italian family with CADASIL features. Neurobiol Aging 36(1):547.e5-11, the entire contents of each of which are incorporated herein by reference.

In some embodiments, a NOTCH3 agonist is administered as a monotherapy. In certain embodiments, especially where the SVD is CADASIL, the subject is not administered a thrombolytic agent.

Aspects include a NOTCH3 agonist, as well methods and compositions comprising a NOTCH3 agonist, where the NOTCH3 agonist comprises a polypeptide, an antibody or a fragment thereof, an aptamer, or a small molecule.

In various embodiments, the NOTCH3 agonist comprises a polypeptide. In some embodiments, the polypeptide comprises a fragment of a NOTCH3 ligand. In certain embodiments, the ligand comprises JAGGED1 or a fragment thereof, JAGGED2 or a fragment thereof, or DELTA-LIKE1 or a fragment thereof.

In certain embodiments, the NOTCH3 agonist comprises a fragment of JAGGED1. In some embodiments, the fragment of JAGGED1 is the extracellular domain of JAGGED1 or a fragment thereof comprising a stretch of amino acids having the sequence CDDYYYGFGCNKFCRPR (SEQ ID NO:1). In various embodiments, the fragment of JAGGED1 comprises a stretch of amino acids having the sequence (SEQ ID NO: 2)
CDDYYYGFGCNKFCRPRDDFFGH In some embodiments, the NOTCH3 agonist comprises a fragment of JAGGED2. In various embodiments, the fragment of JAGGED2 is the extracellular domain of JAGGED2 or a fragment thereof comprising a stretch of amino acids having the sequence CDENYYSATCNKFCRPR (SEQ ID NO:3). In certain embodiments, the fragment of JAGGED2 comprises a stretch of amino acids having the sequence (SEQ ID NO: 4)
CDENYYSATCNKFCRPRNDFFGH In various embodiments, the NOTCH3 agonist comprises a fragment of DELTA-LIKE1. In some embodiments, the fragment of DELTA-LIKE1 is the extracellular domain of DELTA-LIKE1 or a fragment thereof comprising a stretch of amino acids having the sequence CDEHYYGEGCSVFCRPR (SEQ ID NO:5). In various embodiments, the fragment of DELTA-LIKE1 comprises a stretch of amino acids having the sequence (SEQ ID NO: 6)
CDEHYYGEGCSVFCRPRDDAFGH In certain embodiments, the polypeptide comprises a fragment of DELTA-LIKE3. In some embodiments, the fragment of DELTA-LIKE3 is the extracellular domain of DELTA-LIKE3 or a fragment thereof comprising a stretch of amino acids having the sequence (SEQ ID NO: 7)
CEPPAVGTACTRLCRPR.

In various embodiments, the polypeptide comprises a fragment of DELTA-LIKE4. In certain embodiments, the fragment of DELTA-LIKE4 is the extracellular domain of DELTA-LIKE4 or a fragment thereof comprising a stretch of amino acids having the sequence CSDNYYGDNCSRLCKKR (SEQ ID NO:8). In some embodiments, the fragment of DELTA-LIKE4 comprises a stretch of amino acids having the sequence (SEQ ID NO: 9)
CSDNYYGDNCSRLCKKRNDHFGH.

In certain embodiments, the NOTCH3 agonist increases or decreases the expression or activity of a known modulator of NOTCH3 signaling. Non-limiting examples of NOTCH3 signaling modulators are described in Hicks et al. (2000) Nature Cell Biology 2, 515-520; Moloney et al. (2000) Nature 406(6794):369-75; and Matsuno et al. (1998) Nat Genet. 19(1):74-8, the entire contents of each of which are incorporated herein by reference. In some embodiments, the NOTCH3 agonist increases the expression or activity of a protein encoded by a gene within the fringe family of genes. In various embodiments, the NOTCH3 agonist increases the expression or activity of Lunatic fringe (LFNG). In certain embodiments, the NOTCH3 agonist increases the expression or activity of a Fringe protein that has glycosyltransferase activity. In various embodiments, the NOTCH3 agonist increases the expression or activity of a Fringe protein that has fucose-specific beta1,3 N-acetylglucosaminyltransferase activity. In some embodiments, the protein initiates elongation of O-linked fucose residues attached to a epidermal growth factor-like sequence repeat of NOTCH3. In some embodiments, the NOTCH3 agonist decreases the expression or activity of a protein encoded by a gene within the fringe family of genes. In various embodiments, the NOTCH3 agonist decreases the expression or activity of Lunatic fringe (LFNG). In certain embodiments, the NOTCH3 agonist decreases the expression or activity of a Fringe protein that has glycosyltransferase activity. In various embodiments, the NOTCH3 agonist decreases the expression or activity of a Fringe protein that has fucose-specific beta1,3 N-acetylglucosaminyltransferase activity. In some embodiments, the protein initiates elongation of O-linked fucose residues attached to an epidermal growth factor-like sequence repeat of NOTCH3. In certain embodiments, the NOTCH3 agonist increases the expression or activity of suppressor of hairless [Su(H)] or deltex (dx). In certain embodiments, the NOTCH3 agonist increases the expression or activity of RBPJ (recombining binding protein suppressor of hairless; UniProt No. Q06330) or DELTEX. In certain embodiments, the NOTCH3 agonist decreases the expression or activity of suppressor of hairless [Su(H)] or deltex (dx).

Aspects also include compositions comprising a NOTCH3 agonist and a pharmaceutically acceptable carrier for treating or preventing a SVD in a subject. Uses of a NOTCH3 agonist in the manufacture of a medicament for treating or preventing a SVD in a subject are also disclosed herein.

Also provided are compositions comprising an effective amount of a NOTCH3 agonist and an ophthalmically acceptable vehicle. In some embodiments, the composition is in the form of an aqueous solution comprising an osmolality of about 200 to about 400 milliosmoles/kilogram water.

Each embodiment disclosed herein is contemplated as being applicable to each of the other disclosed embodiments. Thus, all combinations of the various elements described herein are within the scope of the invention.

Other features and advantages of the invention will be apparent from the following description of the preferred embodiments thereof, and from the claims. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below.

DESCRIPTION OF THE DRAWINGS

(FIG. 1A) Schematic representation of four mouse strains utilized to study genetic rescue of Notch 3 signaling: wild type Notch 3 (N3WT, white), Notch 3 knockout (N3KO, light gray), mice N3KO conditionally expressing wild type human Notch 3 (hN3WT, dark gray) and N3KO mice conditionally expressing a human CADASIL mutant Notch 3 (C455R, black).

(FIG. 3A) Representative FA images from wild type Notch 3 (N3WT), Notch 3 knockout (N3KO), N3KO mice conditionally expressing wild type human Notch 3 (hN3WT), N3KO mice conditionally expressing a human CADASIL mutant Notch 3 (C455R), and N3KO mice conditionally expressing a human CADASIL mutant Notch 3 and a wild type human Notch 3 (C455R/hN3WT). Arrows indicate leakage events. (FIG. 3B) Graph shows quantification of leakage events in the listed genotypes: N3WT (n=6), N3KO (n=6), hN3WT (n=5), C455R (n=3), C455R/hN3WT (n=5). ** $p<0.05$. NS means non significant.

DETAILED DESCRIPTION

Figure 1A:
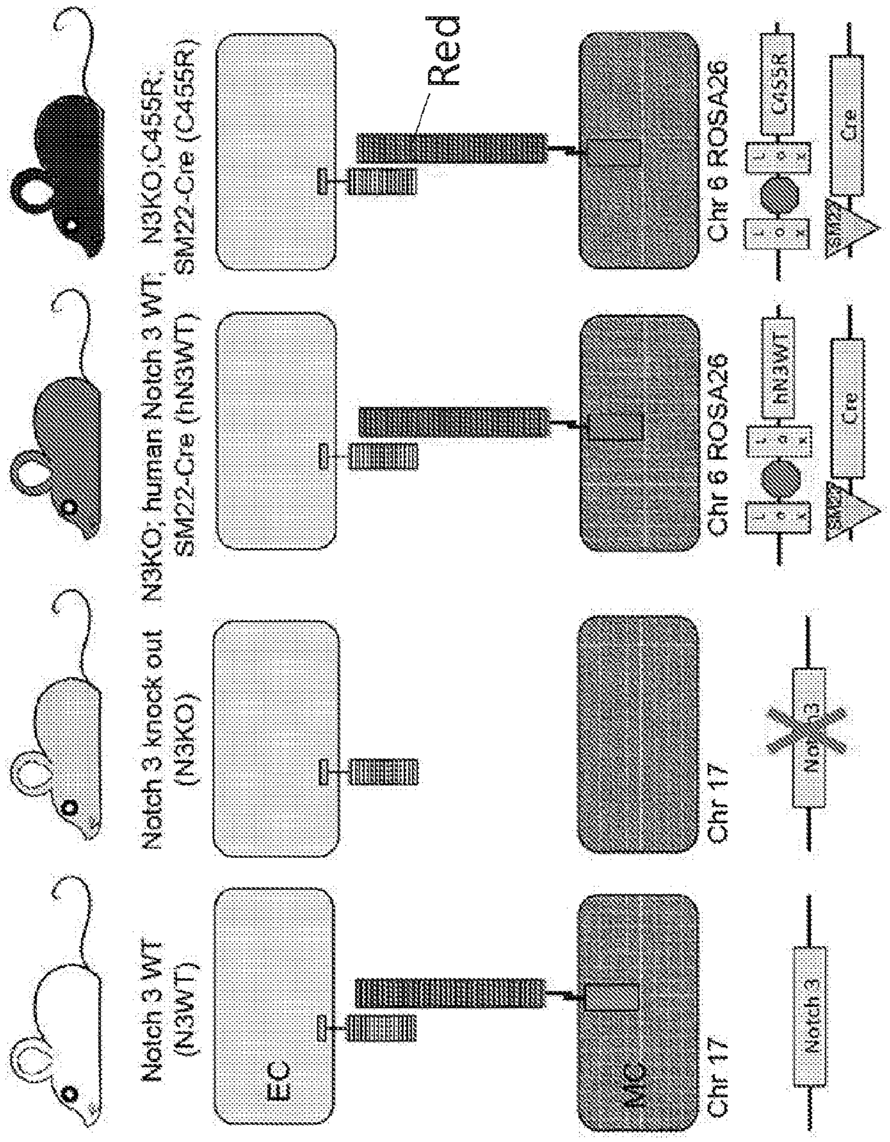
FIG. 1A is a cartoon.

Provided are methods of treating SVD, including CADASIL and NOTCH3 loss of function-associated SVD, with a Notch agonist. Exemplary agonists include antibodies, e.g., monoclonal antibodies that bind to the ectodomain (SEQ ID NO: 12) of NOTCH3. Such antibodies activate the receptor. Exemplary antibodies are described in U.S. Pat. No. 8,513,388, hereby incorporated by reference. Cerebral SVD affects about a third of individuals over 80 years of age, and is a leading cause of stroke, cognitive impairment, and dementia. No disease modifying therapies are available and most treatments focus on managing cardiovascular risk factors known to contribute to the disease. Loss of mural cells, which encompass pericytes and vascular smooth muscle cells, is a hallmark of SVD resulting in vascular instability. NOTCH3 signaling is both necessary and sufficient to support mural cell coverage in arteries using genetic rescue, and SVD may be treated by modulating NOTCH3 signaling. Additionally, the levels of NOTCH3 ectodomain and/or endostatin/collagen 18α1 in patient-derived tissue or bodily fluid samples can be used as surrogate markers of NOTCH3 activity in vivo.

Small vessel diseases are highly prevalent and impact highly vascularized tissues such as the brain, retina, and the kidney. In the brain, small vessel disease is the most prevalent neurological condition and a strong contributor to the susceptibility to stroke, vascular cognitive impairment, and dementia. In the retina, small vessel disease plays a critical role in early stage diabetic retinopathy, which is characterized by mural cell loss. Prior to the methods and compositions provided herein, there were no specific treatments to prevent mural cell degeneration in small vessel disease. Included herein are methods of treating SVD with Notch signaling activators. In some embodiments, mural cell degeneration is reduced or prevented in SVD, e.g., in vascularized tissues such as retina and brain.

CADASIL is a monogenic cause of cerebral small vessel disease associated with mutations in the NOTCH3 gene. There are no specific treatments for small vessels disease in general or CADASIL in particular. Methods and compositions provided herein solve this practical problem by using NOTCH3 signaling in mural cells as a therapeutic target to prevent mural cell loss in small vessel diseases. Prior to the present invention, there were no methods to address mural cell loss in SVD.

NOTCH3 loss of function-associated SVD is distinct from CADASIL because it lacks the characteristic accumulation of Notch 3 extracellular domain in vessels and it lacks granular osmiophilic deposits (GOMs). Prior to the present invention, there were no methods to address mural cell loss in NOTCH3 loss of function-associated SVD. In embodiments, a subject with such a SVD has symptoms that are similar to CADASIL. See, e.g., Moccia et al., (2015) Hypomorphic NOTCH3 mutation in an Italian family with CADASIL features. Neurobiol Aging 36(1):547.e5-11; the entire contents of which is incorporated herein by reference. In various embodiments, the subject has migraines. In some embodiments, the subject has migraines with aura. In certain embodiments, the skin of the subject comprises vascular damage. In various embodiments, the subject has cerebral SVD. A non-limiting example of a mutation that may result in a SVD symptoms similar to CADASIL is a C to U substitution at position 307 of the open reading frame of NOTCH3-encoding mRNA (a cDNA sequence is provided as SEQ ID NO: 11), which results in a truncation of the protein such that amino acids from position R103 to the wild-type C-terminus are missing.

In some embodiments, the subject comprises a R103X substitution mutation. In certain embodiments, the mutation results in a substitution or a truncation within an Epidermal Growth-Factor-like Repeat of NOTCH3. In various embodiments, the mutation is within one of exons 2-24 of the NOTCH3 gene. In some embodiments, the mutation is a missense mutation in exon 25 of NOTCH3. In some embodiments, the substitution is not a conservative substitution. In certain embodiments, the subject comprises an autosomal mutation in NOTCH3. In some embodiments, the mutation results in reduced NOTCH3 function. In some embodiments, the mutation comprises substitution in the extracellular domain of NOTCH3 that adds or removes a cysteine compared to wild-type NOTCH3. In certain embodiments, the mutation comprises a truncation beginning in the extracellular domain of the NOTCH3 protein. In embodiments, the subject is heterozygous for the mutation. In embodiments, the subject is homozygous for the mutation.

Without being bound by any scientific theory, the non-limiting data herein show for the first time that NOTCH3 signaling is both necessary and sufficient to sustain mural cell coverage in arteries via a cell autonomous effect. This finding is demonstrated, e.g. by rescuing mural degeneration in a NOTCH3 knockout by expressing the human NOTCH3 protein specifically in mural cells. This finding is demonstrated, e.g. by rescuing vascular leakage events in a NOTCH3 knockout by expressing the human NOTCH3 protein specifically in mural cells. This finding is demonstrated, e.g. by rescuing vascular leakage events in a NOTCH3 knockout expressing the C455R CADASIL mutation by also expressing the wild type human NOTCH3 protein specifically in mural cells. This finding is demonstrated, e.g. by the observation of indistinguishable levels of mural cell loss and frequency of vascular leakage events between NOTCH3 knockouts and NOTCH3 knockouts expressing the C455R CADASIL mutation. This finding shows that a gene replacement approach, in which a defective NOTCH3 is replaced by a wild-type NOTCH3 specifically in mural cells, results in a functional rescue. This is surprising because NOTCH3 is expressed in other cell types including monocytes/macrophages, other immune cells, and stem cells all of which have been shown to play roles in the vasculatures. See, e.g., Fung et al., (2007) Delta-like 4 induces notch signaling in macrophages: implications for inflammation. Circulation 115(23):2948-56; and Lafkas et al., (2013) NOTCH3 marks clonogenic mammary luminal progenitor cells in vivo. *J Cell Biol.* 203(1):47-56, the entire contents of which are hereby incorporated herein by reference. This is surprising because the predominant view is that CADASIL mutations in NOTCH3 operate via neomorphic toxic gain of function effects. It is therefore unexpected and surprising that by increasing NOTCH3 signaling in mural cells one can rescue vascular degeneration and thus bypass the neomorphic effects.

The following findings were unexpected:

(i) The discovery was made using a NOTCH3 mutation associated with the human small vessel disease called CADASIL (cerebral autosomal dominant arteriopathy with subcortical infarcts and leukoencephalopathy) (Arboleda-Velasquez et al., Neurology 59:277-279, 2002; Arboleda-Velasquez et al., Proc Natl Acad Sci USA 105:4856-4861, 2008; Arboleda-Velasquez et al., Proc Natl Acad Sci USA 108:E128-135, 2011). In that condition, the most widely accepted pathobiological mechanism is that of toxic neomorphism via accumulation of the NOTCH3 receptor extracellular domain whereas NOTCH3 signaling defects due to the mutations are not considered to be primary drivers of the disease (Joutel et al., J Cereb Blood Flow Metab, 36(1):143-57, 2016). In a challenge to this paradigm, the data herein shows that mural cell loss and vascular leakage in a model carrying the CADASIL mutation was similar to that of the mice lacking NOTCH3 (knockout), suggesting a negligible contribution of the toxic neomorphic effects. It is also surprising that the expression of the WT human Notch3 in the presence of a CADASIL mutant Notch 3 rescues the phenotype. This further supports the idea of a negligible contribution of the toxic neomorphic effects.

(ii) The discovery was made using a NOTCH3 knockout mouse model. NOTCH3 loss of function mutations including premature stop codons and frame shifts have been reported in individuals with SVD. See, e.g., Pippucci et al., (2015) Homozygous NOTCH3 null mutation and impaired NOTCH3 signaling in recessive early-onset arteriopathy and cavitating leukoencephalopathy. EMBO Mol Med. 7(6):848-58; Moccia et al., (2015) Hypomorphic NOTCH3 mutation in an Italian family with CADASIL features. Neurobiol Aging 36(1):547.e5-11, the entire contents of each of which are incorporated herein by reference. However, the clinical significance of these mutations has been highly debated and the most widely accepted view is that they represent variants of polymorphic nature. See, e.g., Rutten et al., (2013) Hypomorphic NOTCH3 alleles do not cause CADASIL in humans. Hum Mutat. 34(11): 1486-9, the entire content of which is incorporated herein by reference. In a challenge to this paradigm, the data herein shows that a NOTCH3 knockout develops an SVD phenotype that can be rescued by expression of wild type NOTCH3 in mural cells, unambiguously linking NOTCH3 deficiency to SVD in an experimental model.

(iii) Because Notch signaling regulates a developmental program, it is unexpected that a process resulting from defective signaling could be corrected or prevented from being fulfilled. Accordingly, the ability of NOTCH3 agonism to prevent or treat mural cell loss is surprising.

NOTCH3

The NOTCH3 gene encodes the third discovered human homologue of the *Drosophila melanogaster* type I membrane protein notch. In *Drosophila*, notch's interaction with its cell-bound ligands (delta, serrate) establishes an intercellular signaling pathway that plays a key role in neural development. Homologues of the notch-ligands have also been identified in humans, but precise interactions between these ligands and the human notch homologues remains to be determined. NOTCH3 functions as a receptor for membrane-bound ligands such as JAGGED1, JAGGED2 and DELTA-LIKE1 to regulate cell-fate determination. NOTCH3 has been proposed to affect the implementation of differentiation, proliferation and apoptotic programs. Mutations in NOTCH3 have been identified as the underlying cause of cerebral autosomal dominant arteriopathy with subcortical infarcts and leukoencephalopathy (CADASIL) and other SVD conditions similar to CADASIL.

The cytogenetic band of the NOTCH3 gene has been reported to be 19p13.12 by Ensembl, 19p13.12 by Entrez Gene, and 19p13.12 by the HUGO Gene Nomenclature Committee. According to Ensemble, the location of the NOTCH3 gene is Chromosome 19: 15,159,038-15,200,981 reverse strand (Ensembl release 87—Dec. 2016). Additionally, this gene maps to 15,269,849-15,311,792 in GRCh37 coordinates. Non-limiting examples of NOTCH3 genomic sequences are available from public databases such as Genbank (see, e.g., Accession Nos. NC_000019.10 and AH006054.2).

An amino acid sequence for human NOTCH3 is publically available in the UniProt database under accession number Q9UM47 (SEQ ID NO: 10) and is as follows (exemplary sites that may be substituted in subjects with SVD including CADASIL, cysteine-sparing mutations and Notch 3 loss of function mutations are bolded and underlined):

MGPGARGRRRRRRPMSPPPPPPPVRALPLLLLLAGPGAAAPPCLDGSPCANGGRCTQLP

SREAACLCPPGWVGERCQLEDPCHSGPCAGRGVCQSSVVAGTARFSCRCPRGFRGP

DCSLPDPCLSSPCAHGARCSVGPDGRFLCSCPPGYQGRSCRSDVDECRVGEPCRHGGT

CLNTPGSFRCQCPAGYTGPLCENPAVPCAPSPCRNGGTCRQSGDLTYDCACLPGFEGQ

NCEVNVDDCPGHRCLNGGTCVDGVNTYNCQCPPEWTGQFCTEDVDECQLQPNACHN

GGTCFNTLGGHSCVCVNGWTGESCSQNIDDCATAVCFHGATCHDRVASFYCACPMGK

TGLLCHLDDACVSNPCHEDAICDTNPVNGRAICTCPPGFTGGACDQDVDECSIGANPCE

HLGRCVNTQGSFLCQCGRGYTGPRCETDVNECLSGPCRNQATCLDRIGQFTCICMAGF

TGTYCEVDIDECQSSPCVNGGVCKDRVNGFSCTCPSGFSGSTCQLDVDECASTPCRNGA

KCVDQPDGYECRCAEGFEGTLCDRNVDDCSPDPCHHGRCVDGIASFSCACAPGYTGTR

CESQVDECRSQPCRHGGKCLDLVDKYLCRCPSGTTGVNCEVNIDDCASNPCTFGVCRD

GINRYDCVCQPGFTGPLCNVEINECASSPCGEGGSCVDGENGFRCLCPPGSLPPLCLPPSH

PCAHEPCSHGICYDAPGGFRCVCEPGWSGPRCSQSLARDACESQPCRAGGTCSSDGMG

FHCTCPPGVQGRQCELLSPCTPNPCEHGGRCESAPGQLPVCSCPQGWQGPRCQQDVDE

CAGPAPCGPHGICTNLAGSFSCTCHGGYTGPSCDQDINDCDPNPCLNGGSCQDGVGSFS

CSCLPGFAGPRCARDVDECLSNPCGPGTCTDHVASFTCTCPPGYGGFHCEQDLPDCSPSS

CFNGGTCVDGVNSFSCLCRPGYTGAHCQHEADPCLSRPCLHGGVCSAAHPGFRCTCLE

SFTGPQCQTLVDWCSRQPCQNGGRCVQTGAYCLCPPGWSGRLCDIRSLPCREAAAQIG

VRLEQLCQAGGQCVDEDSSHYCVCPEGRTGSHCEQEVDPCLAQPCQHGGTCRGYMGG

YMCECLPGYNGDNCEDDVDECASQPCQHGGSCIDLVARYLCSCPPGTLGVLCEINEDD

CGPGPPLDSGPRCLHNGTCVDLVGGFRCTCPPGYTGLRCEADINECRSGACHAAHTRD

CLQDPGGGFRCLCHAGFSGPRCQTVLSPCESQPCQHGGQCRPSPGPGGGLTFTCHCAQP

FWGPRCERVARSCRELQCPVGVPCQQTPRGPRCACPPGLSGPSCRSFPGSPPGASNASCA

AAPCLHGGSCRPAPLAPFFRCACAQGWTGPRCEAPAAAPEVSEEPRCPRAACQAKRGD

QRCDRECNSPGCGWDGGDCSLSVGDPWRQCEALQCWRLFNNSRCDPACSSPACLYDN

FDCHAGGRERTCNPVYEKYCADHFADGRCDQGCNTEECGWDGLDCASEVPALLARGV

LVLTVLLPPEELLRSSADFLQRLSAILRTSLRFRLDAHGQAMVFPYHRPSPGSEPRARREL

APEVIGSVVMLEIDNRLCLQSPENDHCFPDAQSAADYLGALSAVERLDFPYPLRDVRGE

PLEPPEPSVPLLPLLVAGAVLLLVILVLGVMVARRKREHSTLWFPEGFSLHKDVASGHK

GRREPVGQDALGMKNMAKGESLMGEVATDWMDTECPEAKRLKVEEPGMGAEEAVDC

RQWTQHHLVAADIRVAPAMALTPPQGDADADGMDVNVRGPDGFTPLMLASFCGGALE

PMPTEEDEADDTSASIISDLICQGAQLGARTDRTGETALHLAARYARADAAKRLLDAGA

DTNAQDHSGRTPLHTAVTADAQGVFQILIRNRSTDLDARMADGSTALILAARLAVEGM

VEELIASHADVNAVDELGKSALHWAAAVNNVEATLALLKNGANKDMQDSKEETPLFL

AAREGSYEAAKLLLDHFANREITDHLDRLPRDVAQERLHQDIVRLLDQPSGPRSPPGPH

GLGPLLCPPGAFLPGLKAAQSGSKKSRRPPGKAGLGPQGPRGRGKKLTLACPGPLADSS

VTLSPVDSLDSPRPFGGPPASPGGFPLEGPYAAATATAVSLAQLGGPGRAGLGRQPPGG

CVLSLGLLNPVAVPLDWARLPPPAPPGPSFLLPLAPGPQLLNPGTPVSPQERPPPYLAVPG

HGEEYPAAGAHSSPPKARFLRVPSEHPYLTPSPESPEHWASPSPPSLSDWSESTPSPATAT

GAMATTTGALPAQPLPLSVPSSLAQAQTQLGPQPEVTPKRQVLA

A nucleotide sequence that encodes human NOTCH3 is publically available in the GenBank database under accession number NM_000435.2 and is as follows (the start and stop codons are underlined and bolded):

```
                                           (SEQ ID No. 32)
GCGGCGCGGAGGCTGGCCCGGGACGCGCCCGGAGCCCAGGGAAGGAGGGAGGAGG

GGAGGGTCGCGGCCGGCCGCC**ATG**GGGCCGGGGGCCCGTGGCCGCCGCCGCCGCCG

TCGCCCGATGTCGCCGCCACCGCCACCGCCACCCGTGCGGGCGCTGCCCCTGCTGCT

GCTGCTAGCGGGGCCGGGGGCTGCAGCCCCCCCTTGCCTGGACGGAAGCCCGTGTG

CAAATGGAGGTCGTTGCACCCAGCTGCCCTCCCGGGAGGCTGCCTGCCTGTGCCCGC

CTGGCTGGGTGGGTGAGCGGTGTCAGCTGGAGGACCCCTGTCACTCAGGCCCCTGTG

CTGGCCGTGGTGTCTGCCAGAGTTCAGTGGTGGCTGGCACCGCCCGATTCTCATGCC

GGTGCCCCCGTGGCTTCCGAGGCCCTGACTGCTCCCTGCCAGATCCCTGCCTCAGCA

GCCCTTGTGCCCACGGTGCCCGCTGCTCAGTGGGGCCCGATGGACGCTTCCTCTGCT

CCTGCCCACCTGGCTACCAGGGCCGCAGCTGCCGAAGCGACGTGGATGAGTGCCGG

GTGGGTGAGCCCTGCCGCCATGGTGGCACCTGCCTCAACACACCTGGCTCCTTCCGC

TGCCAGTGTCCAGCTGGCTACACAGGGCCACTATGTGAGAACCCCGCGGTGCCCTGT

GCACCCTCACCATGCCGTAACGGGGGCACCTGCAGGCAGAGTGGCGACCTCACTTA

CGACTGTGCCTGTCTTCCTGGGTTTGAGGGTCAGAATTGTGAAGTGAACGTGGACGA

CTGTCCAGGACACCGATGTCTCAATGGGGGGACATGCGTGGATGGCGTCAACACCT

ATAACTGCCAGTGCCCTCCTGAGTGGACAGGCCAGTTCTGCACGGAGGACGTGGAT

GAGTGTCAGCTGCAGCCCAACGCCTGCCACAATGGGGGTACCTGCTTCAACACGCT

GGGTGGCCACAGCTGCGTGTGTGTCAATGGCTGGACAGGCGAGAGCTGCAGTCAGA

ATATCGATGACTGTGCCACAGCCGTGTGCTTCCATGGGGCCACCTGCCATGACCGCG

TGGCTTCTTTCTACTGTGCCTGCCCCATGGGCAAGACTGGCCTCCTGTGTCACCTGGA

TGACGCCTGTGTCAGCAACCCCTGCCACGAGGATGCTATCTGTGACACAAATCCGGT

GAACGGCCGGGCCATTTGCACCTGTCCTCCCGGCTTCACGGGTGGGGCATGTGACCA

GGATGTGGACGAGTGCTCTATCGGCGCCAACCCCTGCGAGCACTTGGGCAGGTGCG

TGAACACGCAGGGCTCCTTCCTGTGCCAGTGCGGTCGTGGCTACACTGGACCTCGCT

GTGAGACCGATGTCAACGAGTGTCTGTCGGGGCCCTGCCGAAACCAGGCCACGTGC

CTCGACCGCATAGGCCAGTTCACCTGTATCTGTATGGCAGGCTTCACAGGAACCTAT

TGCGAGGTGGACATTGACGAGTGTCAGAGTAGCCCCTGTGTCAACGGTGGGGTCTG

CAAGGACCGAGTCAATGGCTTCAGCTGCACCTGCCCCCTCGGGCTTCAGCGGCTCCAC

GTGTCAGCTGGACGTGGACGAATGCGCCAGCACGCCCTGCAGGAATGGCGCCAAAT

GCGTGGACCAGCCCGATGGCTACGAGTGCCGCTGTGCCGAGGGCTTTGAGGGCACG

CTGTGTGATCGCAACGTGGACGACTGCTCCCCTGACCCATGCCACCATGGTCGCTGC

GTGGATGGCATCGCCAGCTTCTCATGTGCCTGTGCTCCTGGCTACACGGGCACACGC

TGCGAGAGCCAGGTGGACGAATGCCGCAGCCAGCCCTGCCGCCATGGCGGCAAATG

CCTAGACCTGGTGGACAAGTACCTCTGCCGCTGCCCTTCTGGGACCACAGGTGTGAA

CTGCGAAGTGAACATTGACGACTGTGCCAGCAACCCCTGCACCTTTGGAGTCTGCCG

TGATGGCATCAACCGCTACGACTGTGTCTGCCAACCTGGCTTCACAGGGCCCCTTTG

TAACGTGGAGATCAATGAGTGTGCTTCCAGCCCATGCGGCGAGGGAGGTTCCTGTGT

GGATGGGGAAAATGGCTTCCGCTGCCTCTGCCCGCCTGGCTCCTTGCCCCCACTCTG

CCTCCCCCCGAGCCATCCCTGTGCCCATGAGCCCTGCAGTCACGGCATCTGCTATGA
```

-continued

TGCACCTGGCGGGTTCCGCTGTGTGTGTGAGCCTGGCTGGAGTGGCCCCCGCTGCAG

CCAGAGCCTGGCCCGAGACGCCTGTGAGTCCCAGCCGTGCAGGGCCGGTGGGACAT

GCAGCAGCGATGGAATGGGTTTCCACTGCACCTGCCCGCCTGGTGTCCAGGGACGTC

AGTGTGAACTCCTCTCCCCCTGCACCCCGAACCCCTGTGAGCATGGGGGCCGCTGCG

AGTCTGCCCCTGGCCAGCTGCCTGTCTGCTCCTGCCCCCAGGGCTGGCAAGGCCCAC

GATGCCAGCAGGATGTGGACGAGTGTGCTGGCCCCGCACCCTGTGGCCCTCATGGT

ATCTGCACCAACCTGGCAGGGAGTTTCAGCTGCACCTGCCATGGAGGGTACACTGG

CCCTTCCTGCGATCAGGACATCAATGACTGTGACCCCAACCCATGCCTGAACGGTGG

CTCGTGCCAAGACGGCGTGGGCTCCTTTTCCTGCTCCTGCCTCCCTGGTTTCGCCGGC

CCACGATGCGCCCGCGATGTGGATGAGTGCCTGAGCAACCCCTGCGGCCCGGGCAC

CTGTACCGACCACGTGGCCTCCTTCACCTGCACCTGCCCGCCAGGCTACGGAGGCTT

CCACTGCGAACAGGACCTGCCCGACTGCAGCCCCAGCTCCTGCTTCAATGGCGGGA

CCTGTGTGGACGGCGTGAACTCGTTCAGCTGCCTGTGCCGTCCCGGCTACACAGGAG

CCCACTGCCAACATGAGGCAGACCCCTGCCTCTCGCGGCCCTGCCTACACGGGGGC

GTCTGCAGCGCCGCCCACCCTGGCTTCCGCTGCACCTGCCTCGAGAGCTTCACGGGC

CCGCAGTGCCAGACGCTGGTGGATTGGTGCAGCCGCCAGCCTTGTCAAAACGGGGG

TCGCTGCGTCCAGACTGGGGCCTATTGCCTTTGTCCCCCTGGATGGAGCGGACGCCT

CTGTGACATCCGAAGCTTGCCCTGCAGGGAGGCCGCAGCCCAGATCGGGGTGCGGC

TGGAGCAGCTGTGTCAGGCGGGTGGGCAGTGTGTGGATGAAGACAGCTCCCACTAC

TGCGTGTGCCCAGAGGGCCGTACTGGTAGCCACTGTGAGCAGGAGGTGGACCCCTG

CTTGGCCCAGCCCTGCCAGCATGGGGGGACCTGCCGTGGCTATATGGGGGGCTACA

TGTGTGAGTGTCTTCCTGGCTACAATGGTGATAACTGTGAGGACGACGTGGACGAGT

GTGCCTCCCAGCCCTGCCAGCACGGGGGTTCATGCATTGACCTCGTGGCCCGCTATC

TCTGCTCCTGTCCCCCAGGAACGCTGGGGGTGCTCTGCGAGATTAATGAGGATGACT

GCGGCCCAGGCCCACCGCTGGACTCAGGGCCCCGGTGCCTACACAATGGCACCTGC

GTGGACCTGGTGGGTGGTTTCCGCTGCACCTGTCCCCCAGGATACACTGGTTTGCGC

TGCGAGGCAGACATCAATGAGTGTCGCTCAGGTGCCTGCCACGCGGCACACACCCG

GGACTGCCTGCAGGACCCAGGCGGAGGTTTCCGTTGCCTTTGTCATGCTGGCTTCTC

AGGTCCTCGCTGTCAGACTGTCCTGTCTCCCTGCGAGTCCCAGCCATGCCAGCATGG

AGGCCAGTGCCGTCCTAGCCCGGGTCCTGGGGGTGGGCTGACCTTCACCTGTCACTG

TGCCCAGCCGTTCTGGGGTCCGCGTTGCGAGCGGGTGGCGCGCTCCTGCCGGGAGCT

GCAGTGCCCGGTGGGCGTCCCATGCCAGCAGACGCCCCGCGGGCCGCGCTGCGCCT

GCCCCCCAGGGTTGTCGGGACCCTCCTGCCGCAGCTTCCCGGGGTCGCCGCCGGGGG

CCAGCAACGCCAGCTGCGCGGCCGCCCCCTGTCTCCACGGGGGCTCCTGCCGCCCCG

CGCCGCTCGCGCCCTTCTTCCGCTGCGCTTGCGCGCAGGGCTGGACCGGGCCGCGCT

GCGAGGCGCCCGCCGCGGCACCCGAGGTCTCGGAGGAGCCGCGGTGCCCGCGCGCC

GCCTGCCAGGCCAAGCGCGGGGACCAGCGCTGCGACCGCGAGTGCAACAGCCCAGG

CTGCGGCTGGGACGGCGGCGACTGCTCGCTGAGCGTGGGCGACCCCTGGCGGCAAT

GCGAGGCGCTGCAGTGCTGGCGCCTCTTCAACAACAGCCGCTGCGACCCCGCCTGC

AGCTCGCCCGCCTGCCTCTACGACAACTTCGACTGCCACGCCGGTGGCCGCGAGCGC

-continued

ACTTGCAACCCGGTGTACGAGAAGTACTGCGCCGACCACTTTGCCGACGGCCGCTGC

GACCAGGGCTGCAACACGGAGGAGTGCGGCTGGGATGGGCTGGATTGTGCCAGCGA

GGTGCCGGCCCTGCTGGCCCGCGGCGTGCTGGTGCTCACAGTGCTGCTGCCGCCAGA

GGAGCTACTGCGTTCCAGCGCCGACTTTCTGCAGCGGCTCAGCGCCATCCTGCGCAC

CTCGCTGCGCTTCCGCCTGGACGCGCACGGCCAGGCCATGGTCTTCCCTTACCACCG

GCCTAGTCCTGGCTCCGAACCCCGGGCCCGTCGGGAGCTGGCCCCCGAGGTGATCG

GCTCGGTAGTAATGCTGGAGATTGACAACCGGCTCTGCCTGCAGTCGCCTGAGAATG

ATCACTGCTTCCCCGATGCCCAGAGCGCCGCTGACTACCTGGGAGCGTTGTCAGCGG

TGGAGCGCCTGGACTTCCCGTACCCACTGCGGGACGTGCGGGGGGAGCCGCTGGAG

CCTCCAGAACCCAGCGTCCCGCTGCTGCCACTGCTAGTGGCGGGCGCTGTCTTGCTG

CTGGTCATTCTCGTCCTGGGTGTCATGGTGGCCCGGCGCAAGCGCGAGCACAGCACC

CTCTGGTTCCCTGAGGGCTTCTCACTGCACAAGGACGTGGCCTCTGGTCACAAGGGC

CGGCGGGAACCCGTGGGCCAGGACGCGCTGGGCATGAAGAACATGGCCAAGGGTG

AGAGCCTGATGGGGGAGGTGGCCACAGACTGGATGGACACAGAGTGCCCAGAGGC

CAAGCGGCTAAAGGTAGAGGAGCCAGGCATGGGGGCTGAGGAGGCTGTGGATTGCC

GTCAGTGGACTCAACACCATCTGGTTGCTGCTGACATCCGCGTGGCACCAGCCATGG

CACTGACACCACCACAGGGCGACGCAGATGCTGATGGCATGGATGTCAATGTGCGT

GGCCCAGATGGCTTCACCCCGCTAATGCTGGCTTCCTTCTGTGGGGGGGCTCTGGAG

CCAATGCCAACTGAAGAGGATGAGGCAGATGACACATCAGCTAGCATCATCTCCGA

CCTGATCTGCCAGGGGGCTCAGCTTGGGGCACGGACTGACCGTACTGGCGAGACTG

CTTTGCACCTGGCTGCCCGTTATGCCCGTGCTGATGCAGCCAAGCGGCTGCTGGATG

CTGGGGCAGACACCAATGCCCAGGACCACTCAGGCCGCACTCCCCTGCACACAGCT

GTCACAGCCGATGCCCAGGGTGTCTTCCAGATTCTCATCCGAAACCGCTCTACAGAC

TTGGATGCCCGCATGGCAGATGGCTCAACGGCACTGATCCTGGCGGCCCGCCTGGC

AGTAGAGGGCATGGTGGAAGAGCTCATCGCCAGCCATGCTGATGTCAATGCTGTGG

ATGAGCTTGGGAAATCAGCCTTACACTGGGCTGCGGCTGTGAACAACGTGGAAGCC

ACTTTGGCCCTGCTCAAAAATGGAGCCAATAAGGACATGCAGGATAGCAAGGAGGA

GACCCCCCTATTCCTGGCCGCCCGCGAGGGCAGCTATGAGGCTGCCAAGCTGCTGTT

GGACCACTTTGCCAACCGTGAGATCACCGACCACCTGGACAGGCTGCCGCGGGACG

TAGCCCAGGAGAGACTGCACCAGGACATCGTGCGCTTGCTGGATCAACCCAGTGGG

CCCCGCAGCCCCCCCGGTCCCCACGGCCTGGGGCCTCTGCTCTGTCCTCCAGGGGCC

TTCCTCCCTGGCCTCAAAGCGGCACAGTCGGGGTCCAAGAAGAGCAGGAGGCCCCC

CGGGAAGGCGGGGCTGGGGCCGCAGGGGCCCCGGGGGCGGGGCAAGAAGCTGACG

CTGGCCTGCCCGGGCCCCCTGGCTGACAGCTCGGTCACGCTGTCGCCCGTGGACTCG

CTGGACTCCCCGCGGCCTTTCGGTGGGCCCCCTGCTTCCCCTGGTGGCTTCCCCCTTG

AGGGGCCCTATGCAGCTGCCACTGCCACTGCAGTGTCTCTGGCACAGCTTGGTGGCC

CAGGCCGGGCGGGTCTAGGGCGCCAGCCCCCTGGAGGATGTGTACTCAGCCTGGGC

CTGCTGAACCCTGTGGCTGTGCCCCTCGATTGGGCCCGGCTGCCCCCACCTGCCCCT

CCAGGCCCCTCGTTCCTGCTGCCACTGGCGCCGGGACCCCAGCTGCTCAACCCAGGG

ACCCCCGTCTCCCCGCAGGAGCGGCCCCCGCCTTACCTGGCAGTCCCAGGACATGGC

GAGGAGTACCCGGCGGCTGGGGCACACAGCAGCCCCCCAAAGGCCCGCTTCCTGCG

-continued

GGTTCCCAGTGAGCACCCTTACCTGACCCCATCCCCCGAATCCCCTGAGCACTGGGC

CAGCCCCTCACCTCCCTCCCTCTCAGACTGGTCCGAATCCACGCCTAGCCCAGCCAC

TGCCACTGGGGCCATGGCCACCACCACTGGGGCACTGCCTGCCCAGCCACTTCCCTT

GTCTGTTCCCAGCTCCCTTGCTCAGGCCCAGACCCAGCTGGGGCCCCAGCCGGAAGT

TACCCCCAAGAGGCAAGTGTTGGCCTGAGACGCTCGTCAGTTCTTAGATCTTGGGGG

CCTAAAGAGACCCCCGTCCTGCCTCCTTTCTTTCTCTGTCTCTTCCTTCCTTTTAGTCT

TTTTCATCCTCTTCTCTTTCCACCAACCCTCCTGCATCCTTGCCTTGCAGCGTGACCG

AGATAGGTCATCAGCCCAGGGCTTCAGTCTTCCTTTATTTATAATGGGTGGGGGCTA

CCACCCACCCTCTCAGTCTTGTGAAGAGTCTGGGACCTCCTTCTTCCCCACTTCTCTC

TTCCCTCATTCCTTTCTCTCTCCTTCTGGCCTCTCATTTCCTTACACTCTGACATGAAT

GAATTATTATTATTTTTATTTTTCTTTTTTTTTTTACATTTTGTATAGAAACAAATTCA

TTTAAACAAACTTATTATTATTATTTTTTACAAAATATATATATGGAGATGCTCCCTC

CCCCTGTGAACCCCCCAGTGCCCCCGTGGGGCTGAGTCTGTGGGCCCATTCGGCCAA

GCTGGATTCTGTGTACCTAGTACACAGGCATGACTGGGATCCCGTGTACCGAGTACA

CGACCCAGGTATGTACCAAGTAGGCACCCTTGGGCGCACCCACTGGGGCCAGGGGT

CGGGGGAGTGTTGGGAGCCTCCTCCCCACCCCACCTCCCTCACTTCACTGCATTCCA

GATGGGACATGTTCCATAGCCTTGCTGGGGAAGGGCCCACTGCCAACTCCCTCTGCC

CCAGCCCCACCCTTGGCCATCTCCCTTTGGGAACTAGGGGGCTGCTGGTGGGAAATG

GGAGCCAGGGCAGATGTATGCATTCCTTTGTGTCCCTGTAAATGTGGGACTACAAGA

AGAGGAGCTGCCTGAGTGGTACTTTCTCTTCCTGGTAATCCTCTGGCCCAGCCTCAT

GGCAGAATAGAGGTATTTTTAGGCTATTTTTGTAATATGGCTTCTGGTCAAAATCCCT

GTGTAGCTGAATTCCCAAGCCCTGCATTGTACAGCCCCCCACTCCCCTCACCACCTA

ATAAAGGAATAGTTAACACTCAAAAAAAAAAAAAAAAAA

In a NOTCH3-encoding mRNA sequence, each “T” in the sequence above would be a “U”.

Another amino acid sequence for human NOTCH3 is publically available in the GenBank database under accession number AAB91371.1 and is as follows:

(SEQ ID No. 33)

MGPGARGRRRRRRPMSPPPPPPPVRALPLLLLLAGPGAAAPPCLDGSPCANGGRCTQLP

SREAACLCPPGWVGERCQLEDPCHSGPCAGRGVCQSSVVAGTARFSCRCPRGFRGPDCS

LPDPCLSSPCAHGARCSVGPDGRFLCSCPPGYQGRSCRSDVDECRVGEPCRHGGTCLNT

PGSFRCQCPAGYTGPLCENPAVPCAPSPCRNGGTCRQSGDLTYDCACLPGFEGQNCEVN

VDDCPGHRCLNGGTCVDGVNTYNCQCPPEWTGQFCTEDVDECQLQPNACHNGGTCFN

TLGGHSCVCVNGWTGESCSQNIDDCATAVCFHGATCHDRVASFYCACPMGKTGLLCH

LDDACVSNPCHEDAICDTNPVNGRAICTCPPGFTGGACDQDVDECSIGANPCEHLGRCV

NTQGSFLCQCGRGYTGPRCETDVNECLSGPCRNQATCLDRIGQFTCICMAGFTGTYCEV

DIDECQSSPCVNGGVCKDRVNGFSCTCPSGFSGSTCQLDVDECASTPCRNGAKCVDQPD

GYECRCAEGFEGTLCDRNVDDCSPDPCHHGRCVDGIASFSCACAPGYTGTRCESQVDEC

RSQPCRHGGKCLDLVDKYLCRCPSGTTGVNCEVNIDDCASNPCTFGVCRDGINRYDCV

CQPGFTGPLCNVEINECASSPCGEGGSCVDGENGFRCLCPPGSLPPLCLPPSHPCAHEPCS

-continued

HGICYDAPGGFRCVCEPGWSGPRCSQSLARDACESQPCRAGGTCSSDGMGFHCTCPPG
VQGRQCELLSPCTPNPCEHGGRCESAPGQLPVCSCPQGWQGPRCQQDVDECAGPAPCG
PHGICTNLAGSFSCTCHGGYTGPSCDQDINDCDPNPCLNGGSCQDGVGSFSCSCLPGFAG
PRCARDVDECLSNPCGPGTCTDHVASFTCTCPPGYGGFHCEQDLPDCSPSSCFNGGTCV
DGVNSFSCLCRPGYTGAHCQHEADPCLSRPCLHGGVCSAAHPGFRCTCLESFTGPQCQT
LVDWCSRQPCQNGGRCVQTGAYCLCPPGWSGRLCDIRSLPCREAAAQIGVRLEQLCQA
GGQCVDEDSSHYCVCPEGRTGSHCEQEVDPCLAQPCQHGGTCRGYMGGYMCECLPGY
NGDNCEDDVDECASQPCQHGGSCIDLVARYLCSCPPGTLGVLCEINEDDCGPGPPLDSG
PRCLHNGTCVDLVGGFRCTCPPGYTGLRCEADINECRSGACHAAHTRDCLQDPGGGFR
CLCHAGFSGPRCQTVLSPCESQPCQHGGQCRPSPGPGGGLTFTCHCAQPFWGPRCERVA
RSCRELQCPVGVPCQQTPRGPRCACPPGLSGPSCRSFPGSPPGASNASCAAAPCLHGGSC
RPAPLAPFFRCACAQGWTGPRCEAPAAAPEVSEEPRCPRAACQAKRGDQRCDRECNSP
GCGWDGGDCSLSVGDPWRQCEALQCWRLFNNSRCDPACSSPACLYDNFDCHAGGRER
TCNPVYEKYCADHFADGRCDQGCNTEECGWDGLDCASEVPALLARGVLVLTVLLPPEE
LLRSSADFLQRLSAILRTSLRFRLDAHGQAMVFPYHRPSPGSEPRARRELAPEVIGSVVM
LEIDNRLCLQSPENDHCFPDAQSAADYLGALSAVERLDFPYPLRDVRGEPLEPPEPSVPL
LPLLVAGAVLLLVILVLGVMVARRKREHSTLWFPEGFSLHKDVASGHKGRREPVGQDA
LGMKNMAKGESLMGEVATDWMDTECPEAKRLKVEEPGMGAEEAVDCRQWTQHHLV
AADIRVAPAMALTPPQGDADADGMDVNVRGPDGFTPLMLASFCGGALEPMPTEEDEA
DDTSASIISDLICQGAQLGARTDRTGETALHLAARYARADAAKRLLDAGADTNAQDHS
GRTPLHTAVTADAQGVFQILIRNRSTDLDARMADGSTALILAARLAVEGMVEELIASHA
DVNAVDELGKSALHWAAAVNNVEATLALLKNGANKDMQDSKEETPLFLAAREGSYEA
AKLLLDHFANREITDHLDRLPRDVAQERLHQDIVRLLDQPSGPRSPPGPHGLGPLLCPPG
AFLPGLKAAQSGSKKSRRPPGKAGLGPQGPRGRGKKLTLACPGPLADSSVTLSPVDSLD
SPRPFGGPPASPGGFPLEGPYAAATATAVSLAQLGGPGRAGLGRQPPGGCVLSLGLLNP
VAVPLDWARLPPPAPPGPSFLLPLAPGPQLLNPGTPVSPQERPPPYLAVPGHGEEYPVAG
AHSSPPKARFLRVPSEHPYLTPSPESPEHWASPSPPSLSDWSESTPSPATATGAMATTTGA
LPAQPLPLSVPSSLAQAQTQLGPQPEVTPKRQVLA

A nucleotide sequence that encodes human NOTCH3 is publically available in the GenBank database under accession number U97669.1 (SEQ ID NO: 11) and is as follows (the start and stop codons are underlined and bolded):

ACGCGGCGCGGAGGCTGGCCCGGGACGCGCCCGGAGCCCAGGGAAGGAGGGAGGA
GGGGAGGGTCGCGGCCGGCCGCC<u>ATG</u>GGGCCGGGGGCCCGTGGCCGCCGCCGCCG
CCGTCGCCCGATGTCGCCGCCACCGCCACCGCCACCCGTGCGGGCGCTGCCCCTGCT
GCTGCTGCTAGCGGGGCCGGGGGCTGCAGCCCCCCCTTGCCTGGACGGAAGCCCGT
GTGCAAATGGAGGTCGTTGCACCCAGCTGCCCTCCCGGGAGGCTGCCTGCCTGTGCC
CGCCTGGCTGGGTGGGTGAGCGGTGTCAGCTGGAGGACCCCTGTCACTCAGGCCCCT
GTGCTGGCCGTGGTGTCTGCCAGAGTTCAGTGGTGGCTGGCACCGCCCGATTCTCAT
GCCGGTGCCCCCGTGGCTTCCGAGGCCCTGACTGCTCCCTGCCAGATCCCTGCCTCA
GCAGCCCTTGTGCCCACGGTGCCCGCTGCTCAGTGGGGCCCGATGGACGCTTCCTCT

-continued

GCTCCTGCCCACCTGGCTACCAGGGCCGCAGCTGCCGAAGCGACGTGGATGAGTGC

CGGGTGGGTGAGCCCTGCCGCCATGGTGGCACCTGCCTCAACACACCTGGCTCCTTC

CGCTGCCAGTGTCCAGCTGGCTACACAGGGCCACTATGTGAGAACCCCGCGGTGCC

CTGTGCGCCCTCACCATGCCGTAACGGGGGCACCTGCAGGCAGAGTGGCGACCTCA

CTTACGACTGTGCCTGTCTTCCTGGGTTTGAGGGTCAGAATTGTGAAGTGAACGTGG

ACGACTGTCCAGGACACCGATGTCTCAATGGGGGGACATGCGTGGATGGCGTCAAC

ACCTATAACTGCCAGTGCCCTCCTGAGTGGACAGGCCAGTTCTGCACGGAGGACGT

GGATGAGTGTCAGCTGCAGCCCAACGCCTGCCACAATGGGGGTACCTGCTTCAACA

CGCTGGGTGGCCACAGCTGCGT

GTGTGTCAATGGCTGGACAGGTGAGAGCTGCAGTCAGAATATCGATGACTGTGCCA

CAGCCGTGTGCTTCCATGGGGCCACCTGCCATGACCGCGTGGCTTCTTTCTACTGTG

CCTGCCCCATGGGCAAGACTGGCCTCCTGTGTCACCTGGATGACGCCTGTGTCAGCA

ACCCCTGCCACGAGGATGCTATCTGTGACACAAATCCGGTGAACGGCCGGGCCATTT

GCACCTGTCCTCCCGGCTTCACGGGTGGGGCATGTGACCAGGATGTGGACGAGTGCT

CTATCGGCGCCAACCCCTGCGAGCACTTGGGCAGGTGCGTGAACACGCAGGGCTCC

TTCCTGTGCCAGTGCGGTCGTGGCTACACTGGACCTCGCTGTGAGACCGATGTCAAC

GAGTGTCTGTCGGGGCCCTGCCGAAACCAGGCCACGTGCCTCGACCGCATAGGCCA

GTTCACCTGTATCTGTATGGCAGGCTTCACAGGAACC

TATTGCGAGGTGGACATTGACGAGTGTCAGAGTAGCCCCTGTGTCAACGGTGGGGTC

TGCAAGGACCGAGTCAATGGCTTCAGCTGCACCTGCCCCTCGGGCTTCAGCGGCTCC

ACGTGTCAGCTGGACGTGGACGAATGCGCCAGCACGCCCTGCAGGAATGGCGCCAA

ATGCGTGGACCAGCCCGATGGCTACGAGTGCCGCTGTGCCGAGGGCTTTGAGGGCA

CGCTGTGTGATCGCAACGTGGACGACTGCTCCCCTGACCCATGCCACCATGGTCGCT

GCGTGGATGGCATCGCCAGCTTCTCATGTGCCTGTGCTCCTGGCTACACGGGCACAC

GCTGCGAGAGCCAGGTGGACGAATGCCGCAGCCAGCCCTGCCGCCATGGCGGCAAA

TGCCTAGACCTGGTGGACAAGTACCTCTGCCGCTGCCCTTCTGGGACCACAGGTGTG

AACTGCGAAGTGAACATTGACGACTGTGCCAGCAACC

CCTGCACCTTTGGAGTCTGCCGTGATGGCATCAACCGCTACGACTGTGTCTGCCAAC

CTGGCTTCACAGGGCCCCTTTGTAACGTGGAGATCAATGAGTGTGCTTCCAGCCCAT

GCGGCGAGGGAGGTTCCTGTGTGGATGGGGAAAATGGCTTCCGCTGCCTCTGCCCGC

CTGGCTCCTTGCCCCCACTCTGCCTCCCCCCGAGCCATCCCTGTGCCCATGAGCCCTG

CAGTCACGGCATCTGCTATGATGCACCTGGCGGGTTCCGCTGTGTGTGTGAGCCTGG

CTGGAGTGGCCCCCGCTGCAGCCAGAGCCTGGCCCGAGACGCCTGTGAGTCCCAGC

CGTGCAGGGCCGGTGGGACATGCAGCAGCGATGGAATGGGTTTCCACTGCACCTGC

CCGCCTGGTGTCCAGGGACGTCAGTGTGAACTCCTCTCCCCCTGCACCCCGAACCCC

TGTGAGCATGGGGGCCGCTGCGAGTCTGCCCCTGGCCAGCTGCCTGTCTGCTCCTGC

CCCCAGGGCTGGCAAGGCCCACGATGCCAGCAGGATGTGGACGAGTGTGCTGGCCC

CGCACCCTGTGGCCCTCATGGTATCTGCACCAACCTGGCAGGGAGTTTCAGCTGCAC

CTGCCATGGAGGGTACACTGGCCCTTCCTGTGATCAGGACATCAATGACTGTGACCC

CAACCCATGCCTGAACGGTGGCTCGTGCCAAGACGGCGTGGGCTCCTTTTCCTGCTC

-continued

CTGCCTCCCTGGTTTCGCCGGCCCACGATGCGCCCGCGATGTGGATGAGTGCCTGAG

CAACCCCTGCGGCCCGGGCACCTGTACCGACCACGTGGCCTCCTTCACCTGCACCTG

CCCGCCGGGCTACGGAGGCTTCCACTGCGAACAGGACCTGCCCGACTGCAGCCCCA

GCTCCTGCTTCAATGGCGGGACCTGTGTGGACGGCGTGAACTCGTTCAGCTGCCTGT

GCCGTCCCGGCTACACAGGAGCCCACTGCCAACATGAGGCAGACCCCTGCCTCTCG

CGGCCCTGCCTACACGGGGGCGTCTGCAGCGCCGCCCACCCTGGCTTCCGCTGCACC

TGCCTCGAGAGCTTCACGGGCCCGCAGTGCCAGACGCTGGTGGATTGGTGCAGCCG

CCAGCCTTGTCAAAACGGGGGTCGCTGCGTCCAGACTGGGGCCTATTGCCTTTGTCC

CCCTGGATGGAGCGGACGCCTCTGTGACATCCGAAGCTTGCCCTGCAGGGAGGCCG

CAGCCCAGATCGGGGTGCGGCTGGAGCAGCTGTGTCAGGCGGGTGGGCAGTGTGTG

GATGAAGACAGCTCCCACTACTGCGTGTGCCCAGAGGGCCGTACTGGTAGCCACTG

TGAGCAGGAGGTGGACCCCTGCTTGGCCCAGCCCTGCCAGCATGGGGGGACCTGCC

GTGGCTATATGGGGGGCTACATGTGTGAGTGTCTTCCTGGCTACAATGGTGATAACT

GTGAGGACGACGTGGACGAGTGTGCCTCCCAGCCCTGCCAGCACGGGGGTTCATGC

ATTGACCTCGTGGCCCGCTATCTCTGCTCCTGTCCCCCAGGAACGCTGGGGGTGCTC

TGCGAGATTAATGAGGATGACTGCGGCCCAGGCCCACCGCTGGACTCAGGGCCCCG

GTGCCTACACAATGGCACCTGCGTGGACCTGGTGGGTGGTTTCCGCTGCACCTGTCC

CCCAGGATACACTGGTTTGCGCTGCGAGGCAGACATCAATGAGTGTCGCTCAGGTGC

CTGCCACGCGGCACACACCCGGGACTGCCTGCAGGACCCAGGCGGAGGTTTCCGTT

GCCTTTGTCATGCTGGCTTCTCAGGTCCTCGCTGTCAGACTGTCCTGTCTCCCTGCGA

GTCCCAGCCATGCCAGCATGGAGGCCAGTGCCGTCCTAGCCCGGGTCCTGGGGGTG

GGCTGACCTTCACCTGTCACTGTGCCCAGCCGTTCTGGGGTCCGCGTTGCGAGCGGG

TGGCGCGCTCCTGCCGGGAGCTGCAGTGCCCGGTGGGCGTCCCATGCCAGCAGACG

CCCCGCGGGCCGCGCTGCGCCTGCCCCCCAGGGTTGTCGGGACCCTCCTGCCGCAGC

TTCCCGGGGTCGCCGCCGGGGGCCAGCAACGCCAGCTGCGCGGCCGCCCCCTGTCTC

CACGGGGGCTCCTGCCGCCCCGCGCCGCTCGCGCCCTTCTTCCGCTGCGCTTGCGCG

CAGGGCTGGACCGGGCCGCGCTGCGAGGCG

CCCGCCGCGGCACCCGAGGTCTCGGAGGAGCCGCGGTGCCCGCGCGCCGCCTGCCA

GGCCAAGCGCGGGGACCAGCGCTGCGACCGCGAGTGCAACAGCCCAGGCTGCGGCT

GGGACGGCGGCGACTGCTCGCTGAGCGTGGGCGACCCCTGGCGGCAATGCGAGGCG

CTGCAGTGCTGGCGCCTCTTCAACAACAGCCGCTGCGACCCCGCCTGCAGCTCGCCC

GCCTGCCTCTACGACAACTTCGACTGCCACGCCGGTGGCCGCGAGCGCACTTGCAAC

CCGGTGTACGAGAAGTACTGCGCCGACCACTTTGCCGACGGCCGCTGCGACCAGGG

CTGCAACACGGAGGAGTGCGGCTGGGATGGGCTGGATTGTGCCAGCGAGGTGCCGG

CCCTGCTGGCCCGCGGCGTGCTGGTGCTCACAGTGCTGCTGCCGCCGGAGGAGCTAC

TGCGTTCCAGCGCCGACTTTCTGCAGCGGCTCAGCGCCATCCTGCGCACCTCGCTGC

GCTTCCGCCTGGACGCGCACGGCCAGGCCATGGTCTTCCCTTACCACCGGCCTAGTC

CTGGCTCCGAACCCCGGGCCCGTCGGGAGCTGGCCCCCGAGGTGATCGGCTCGGTA

GTAATGCTGGAGATTGACAACCGGCTCTGCCTGCAGTCGCCTGAGAATGATCACTGC

TTCCCCGATGCCCAGAGCGCCGCTGACTACCTGGGAGCGTTGTCAGCGGTGGAGCG

-continued

CCTGGACTTCCCGTACCCACTGCGGGACGTGCGGGGGGAGCCGCTGGAGCCTCCAG

AACCCAGCGTCCCGCTGCTGCCACTGCTAGTGGCGGGCGCTGTCTTGCTGCTGGTCA

TTCTCGTCCTGGGTGTCATGGTGGCCCGGCGCAAGCGCGAGCACAGCACCCTCTGGT

TCCCTGAGGGCTTCTCACTGCACAAGGACGTGGCCTCTGGTCACAAGGGCCGGCGG

GAACCCGTGGGCCAGGACGCGCTGGGCATGAAGAACATGGCCAAGGGTGAGAGCC

TGATGGGGGAGGTGGCCACAGACTGGATGGACACAGAGTGCCCAGAGGCCAAGCG

GCTAAAGGTAGAGGAGCCAGGCATGGGGGCTGAGGAGGCTGTGGATTGCCGTCAGT

GGACTCAACACCATCTGGTTGCTGCTGACATCCGCGTGGCACCAGCCATGGCACTGA

CACCACCACAGGGCGACGCAGATGCTGATGGCATGGATGTCAATGTGCGTGGCCCA

GATGGCTTCACCCCGCTAATGCTGGCTTCCTTCTGTGGGGGGGCTCTGGAGCCAATG

CCAACTGAAGAGGATGAGGCAGATGACACATCAGCTAGCATCATCTCCGACCTGAT

CTGCCAGGGGGCTCAGCTTGGGGCACGGACTGACCGTACTGGCGAGACTGCTTTGC

ACCTGGCTGCCCGTTATGCCCGTGCTGATGCAGCCAAGCGGCTGCTGGATGCTGGGG

CAGAC

ACCAATGCCCAGGACCACTCAGGCCGCACTCCCCTGCACACAGCTGTCACAGCCGA

TGCCCAGGGTGTCTTCCAGATTCTCATCCGAAACCGCTCTACAGACTTGGATGCCCG

CATGGCAGATGGCTCAACGGCACTGATCCTGGCGGCCCGCCTGGCAGTAGAGGGCA

TGGTGGAAGAGCTCATCGCCAGCCATGCTGATGTCAATGCTGTGGATGAGCTTGGGA

AATCAGCCTTACACTGGGCTGCGGCTGTGAACAACGTGGAAGCCACTTTGGCCCTGC

TCAAAAATGGAGCCAATAAGGACATGCAGGATAGCAAGGAGGAGACCCCCCTATTC

CTGGCCGCCCGCGAGGGCAGCTATGAGGCTGCCAAGCTGCTGTTGGACCACTTTGCC

AACCGTGAGATCACCGACCACCTGGACAGGCTGCCGCGGGACGTAGCCCAGGAGAG

ACTGCACCAGGACATCGTGCGCTTGCTGGATCAACCCAGTGGGCCCCGCAGCCCCCC

CGGTCCCCACGGCCTGGGGCCTCTGCTCTGTCCTCCAGGGGCCTTCCTCCCTGGCCTC

AAAGCGGCACAGTCGGGGTCCAAGAAGAGCAGGAGGCCCCCCGGGAAGGCGGGGC

TGGGGCCGCAGGGGCCCCGGGGGCGGGGCAAGAAGCTGACGCTGGCCTGCCCGGG

CCCCCTGGCTGACAGCTCGGTCACGCTGTCGCCCGTGGACTCGCTGGACTCCCCGCG

GCCTTTCGGTGGGCCCCCTGCTTCCCCTGGTGGCTTCCCCCTTGAGGGGCCCTATGCA

GCTGCCACTGCCACTGCAGTGTCTCTGGCACAGCTTGGTGGCCCAGGCCGGGCAGGT

CTAGGGCGCCAGCCCCCTGGAGGATGTGTACTCAGCCTGGGCCTGCTGAACCCTGTG

GCTGTGCCCCTCGATTGGGCCCGGCTGCCCCCACCTGCCCCTCCAGGCCCCTCGTTC

CTGCTGCCACTGGCGCCGGGACCCCAGCTGCTCAACCCAGGGACCCCCGTCTCCCCG

CAGGAGCGGCCCCCGCCTTACCTGGCAGTCCCAGGACATGGCGAGGAGTACCCGGT

GGCTGGGGCACACAGCAGCCCCCCAAAGGCCCGCTTCCTGCGGGTTCCCAGTGAGC

ACCCTTACCTGACCCCATCCCCCGAATCCCCTGAGCACTGGGCCAGCCCCTCACCTC

CCTCCCTCTCAGACTGGTCCGAATCCACGCCTAGCCCAGCCACTGCCACTGGGGCCA

TGGCCACCACCACTGGGGCACTGCCTGCCCAGCCACTTCCCTTGTCTGTTCCCAGCT

CCCTTGCTCAGGCCCAGACCCAGCTGGGGCCCCAGCCGGAAGTTACCCCCAAGAGG

CAAGTGTTGGCCTGAGACGCTCGTCAGTTCTTAGATCTTGGGGGCCTAAAGAGACCC

CCGTCCTGCCTCCTTTCTTTCTCTGTCTCTTCCTTCCTTTTAGTCTTTTTCATCCTCTTC

-continued

```
TCTTTCCACCAACCCTCCTGCATCCTTGCCTTGCAGCGTGACCGAGATAGGTCATCA

GCCCAGGGCTTCAGTCTTCCTTTATTTATAATGGGTGGGGGCTACCACCCACCCTCTC

AGTCTTGTGAAGAGTCTGGGACCTCCTTCTTCCCCACTTCTCTCTTCCCTCATTCCTTT

CTCTCTCCTTCTGGCCTCTCATTTCCTTACACTCTGACATGAATGAATTATTATTATTT

TTCTTTTTCTTTTTTTTTTTACATTTTGTATAGAAACAAATTCATTTAAACAAACTTAT

TATTATTATTTTTTACAAAATATATATATGGAGATGCTCCCTCCCCCTGTGAACCCCC

CAGTGCCCCCGTGGGGCTGAGTCTGTGGGCCCATTCGGCCAAGCTGGATTCTGTGTA

CCTAGTACACAGGCATGACTGGGATCCCGTGTACCGAGTACACGACCCAGGTATGT

ACCAAGTAGGCACCCTTGGGCGCACCCACTGGGGCCAGGGGTCGGGGGAGTGTTGG

GAGCCTCCTCCCCACCCCACCTCCCTCACTTCACT

GCATTCCAGATTGGACATGTTCCATAGCCTTGCTGGGGAAGGGCCCACTGCCAACTC

CCTCTGCCCCAGCCCCACCCTTGGCCATCTCCCTTTGGGAACTAGGGGGCTGCTGGT

GGGAAATGGGAGCCAGGGCAGATGTATGCATTCCTTTATGTCCCTGTAAATGTGGGA

CTACAAGAAGAGGAGCTGCCTGAGTGGTACTTTCTCTTCCTGGTAATCCTCTGGCCC

AGCCTTATGGCAGAATAGAGGTATTTTTAGGCTATTTTTGTAATATGGCTTCTGGTCA

AAATCCCTGTGTAGCTGAATTCCCAAGCCCTGCATTGTACAGCCCCCCACTCCCCTC

ACCACCTAATAAAGGAATAGTTAACACTCAAAAAAAAAAAAAAAAAAA
```

In a NOTCH3-encoding mRNA sequence, each "T" in the sequence above would be a "U".

The human NOTCH3 ectodomain sequence comprises amino acid positions 40 to 1571 of accession number Q9UM47. With respect to embodiments relating to CADASIL, the ectodomain comprises the extracellular domain until the furin cleavage site. This excludes the signal peptide from positions 1 to 39 and also excludes the 1572 to 2321 amino acid region encompassing a small portion that is extracellular, the transmembrane domain, and the intracellular domain.

An amino acid sequence for human N3ECD is:

```
                                              (SEQ ID NO: 12)
APPCLDGSPC ANGGRCTQLP SREAACLCPP GWVGERCQLE

DPCHSGPCAG RGVCQSSVVAGTARFSCRCP RGFRGPDCSL

PDPCLSSPCA HGARCSVGPD GRFLCSCPPG

YQGRSCRSDVDECRVGEPCR HGGTCLNTPG SFRCQCPAGY

TGPLCENPAV PCAPSPCRNG GTCRQSGDLTYDCACLPGFE

GQNCEVNVDD CPGHRCLNGG TCVDGVNTYN

CQCPPEWTGQ FCTEDVDECQLQPNACHNGG TCFNTLGGHS

CVCVNGWTGE SCSQNIDDCA TAVCFHGATC HDRVASFYCA

CPMGKTGLLC HLDDACVSNP CHEDAICDTN PVNGRAICTC

PPGFTGGACD QDVDECSIGANPCEHLGRCVNTQGSFLCQC

GRGYTGPRCE TDVNECLSGP

CRNQATCLDRIGQFTCICMAGFTGTYCEVD IDECQSSPCV

NGGVCKDRVN GFSCTCPSGF SGSTCQLDVD

ECASTPCRNGAKCVDQPDGY ECRCAEGFEG TLCDRNVDDC
```

-continued

```
SPDPCHHGRC VDGIASFSCA CAPGYTGTRCESQVDECRSQ

PCRHGGKCLD LVDKYLCRCP SGTTGVNCEV NIDDCASNPC

TFGVCRDGIN RYDCVCQPGF TGPLCNVEIN

ECASSPCGEG GSCVDGENGF RCLCPPGSLP

PLCLPPSHPCAHEPCSHGIC YDAPGGFRCV CEPGWSGPRC

SQSLARDACE SQPCRAGGTC SSDGMGFHCTCPPGVQGRQC

ELLSPCTPNP CEHGGRCESA PGQLPVCSCP

QGWQGPRCQQ DVDECAGPAPCGPHGICTNL AGSFSCTCHG

GYTGPSCDQD INDCDPNPCL NGGSCQDGVG

SFSCSCLPGFAGPRCARDVD ECLSNPCGPG

TCTDHVASFT CTCPPGYGGF HCEQDLPDCS PSSCFNGGTC

VDGVNSFSCL CRPGYTGAHC QHEADPCLSR PCLHGGVCSA

AHPGFRCTCL ESFTGPQCQTLVDWCSRQPC

QNGGRCVQTG AYCLCPPGWS GRLCDIRSLP CREAAAQIGV

RLEQLCQAGGQCVDEDSSHY CVCPEGRTGS HCEQEVDPCL

AQPCQHGGTC RGYMGGYMCE CLPGYNGDNCEDDVDECASQ

PCQHGGSCID LVARYLCSCP PGTLGVLCEI

NEDDCGPGPP LDSGPRCLHNGTCVDLVGGF RCTCPPGYTG

LRCEADINEC RSGACHAAHT RDCLQDPGGG FRCLCHAGFS

GPRCQTVLSP CESQPCQHGG QCRPSPGPGG GLTFTCHCAQ

PFWGPRCERV ARSCRELQCPVGVPCQQTPR
```

-continued

GPRCACPPGL SGPSCRSFPG SPPGASNASC AAAPCLHGGS

CRPAPLAPFFRCACAQGWTG PRCEAPAAAP EVSEEPRCPR

AACQAKRGDQ RCDRECNSPG CGWDGGDCSLSVGDPWRQCE

ALQCWRLFNN SRCDPACSSP ACLYDNFDCH

AGGRERTCNP VYEKYCADHFADGRCDQGCN

TEECGWDGLD CASEVPALLA RGVLVLTVLL PPEELLRSSA

DFLQRLSAILR TSLRFRLDAHGQAM VFPYHR PSPGSEPRARR

The amino acid sequence for mouse N3ECD runs from positions 40 to 1572 of the amino acid sequence that is available in the UniProt database under accession number Q61982 (SEQ ID NO: 13), and is as follows:

(SEQ ID NO: 13)

APPCLDGSPC ANGGRCTHQQ PSLEAACLCL PGWVGERCQL

EDPCHSGPCA GRGVCQSSVVAGTARFSCRC

LRGFQGPDCS QPDPCVSRPC VHGAPCSVGP DGRFACACPP

GYQGQSCQSDIDECRSGTTC RHGGTCLNTP GSFRCQCPLG

YTGLLCENPV VPCAPSPCRN GGTCRQSSDVTYDCACLPGF

EGQNCEVNVD DCPGHRCLNG GTCVDGVNTY

NCQCPPEWTG QFCTEDVDECQLQPNACHNG GTCFNLLGGH

SCVCVNGWTGESCSQNIDDC ATAVCFHGAT CHDRVASFYC

ACPMGKTGLL CHLDDACVSN PCHEDAICDT NPVSGRAICT

CPPGFTGGAC DQDVDECSIGANPCEHLGRC

VNTQGSFLCQ CGRGYTGPRC ETDVNECLSG PCRNQATCLD

RIGQFTCICMAGFTGTYCEV DIDECQSSPC VNGGVCKDRV

NGFSCTCPSG FSGSMCQLDV DECASTPCRNGAKCVDQPDG

YECRCAEGFE GTLCERNVDD CSPDPCHHGR

CVDGIASFSC ACAPGYTGIRCESQVDECRS QPCRYGGKCL

DLVDKYLCRC PPGTTGVNCE VNIDDCASNP CTFGVCRDGI

NRYDCVCQPG FTGPLCNVEINECASSPCGE GGSCVDGENG

FHCLCPPGSL PPLCLPANHPCAHKPCSHGV

CHDAPGGFRC VCEPGWSGPR CSQSLAPDAC ESQPCQAGGT

CTSDGIGFRCTCAPGFQGHQ CEVLSPCTPS LCEHGGHCES

DPDRLTVCSC PPGWQGPRCQ QDVDECAGASPCGPHGTCTN

LPGNFRCICH RGYTGPFCDQ DIDDCDPNPC

LHGGSCQDGV GSFSCSCLDGFAGPRCARDV DECLSSPCGP

GTCTDHVASF TCACPPGYGG FHCEIDLPDC SPSSCFNGGT

CVDGVSSFSC LCRPGYTGTH CQYEADPCFS RPCLHGGICN

PTHPGFECTC REGFTGSQCQNPVDWCSQAP

CQNGGRCVQT GAYCICPPGW SGRLCDIQSL PCTEAAAQMG

VRLEQLCQEGGKCIDKGRSH YCVCPEGRTG SHCEHEVDPC

TAQPCQHGGT CRGYMGGYVC ECPAGYAGDSCEDNIDECAS

QPCQNGGSCI DLVARYLCSC PPGTLGVLCE

-continued

INEDDCDLGP SLDSGVQCLHNGTCVDLVGG FRCNCPPGYT

GLHCEADINE CRPGACHAAH TRDCLQDPGG HFRCVCHPGF

TGPRCQIALS PCESQPCQHG GQCRHSLGRG GGLTFTCHCV

PPFWGLRCER VARSCRELQCPVGIPCQQTA

RGPRCACPPG LSGPSCRVSR ASPSGATNAS CASAPCLHGG

SCLPVQSVPFFRCVCAPGWG GPRCETPSAA PEVPEEPRCP

RAACQAKRGD QNCDRECNTP GCGWDGGDCSLNVDDPWRQC

EALQCWRLFN NSRCDPACSS PACLYDNFDC

YSGGRDRTCNPVYEKYCADHFADGRCDQGC

NTEECGWDGL DCASEVPALL ARGVLVLTVL LPPEELLRSS

ADFLQRLSAIL RTSLRFRLDARGQAMVFPYH RPSPGSESRV RR

Endostatin

Endostatin is a naturally-occurring, 20-kDa C-terminal fragment derived collagen18α1 (which is encoded by the COL18A1 gene). Endostatin is cleaved off collagen18α1. It is reported to serve as an anti-angiogenic agent, similar to angiostatin and thrombospondin. Endostatin is a broad-spectrum angiogenesis inhibitor and may interfere with the pro-angiogenic action of growth factors such as basic fibroblast growth factor (bFGF/FGF-2) and vascular endothelial growth factor (VEGF).

A binding agent (e.g., an antibody) that specifically binds endostatin may also bind full-length collagen18α1. In various embodiments, it is not necessary to distinguish endostatin that is detected from collagen18α1 (i.e., it is not necessary to rule out or determine that a portion of the endostatin detected is full-length collagen18α1).

An amino acid sequence for human endostatin is publically available in the UniProt database as positions 1572-1754 of accession number P39060 (SEQ ID NO: 24) and is as follows:

HSHRDFQPVLHLVALNSPLSGGMRGIRGADFQCFQQARAVGLAGTFRAF

LSSRLQDLYSIVRRADRAAVPIVNLKDELLFPSWEALFSGSEGPLKPGA

RIFSFDGKDVLRHPTWPQKSVWHGSDPNGRRLTESYCETWRTEAPSATG

QASSLLGGRLLGQSAASCHHAYIVLCIENSFMTASK

A nucleotide sequence that encodes human endostatin is publically available in the GenBank database as positions 4021-4569 of accession number NM_030582.3 (SEQ ID NO: 25) and is as follows:

CACAGCCACC GCGACTTCCA GCCGGTGCTC CACCTGGTTG

CGCTCAACAG CCCCCTGTCAGGCGGCATGC

GGGGCATCCG CGGGGCCGAC TTCCAGTGCT TCCAGCAGGC

GCGGGCCGTGGGGCTGGCGG GCACCTTCCG CGCCTTCCTG

TCCTCGCGCC TGCAGGACCT GTACAGCATCGTGCGCCGTG

CCGACCGCGC AGCCGTGCCC ATCGTCAACC

TCAAGGACGA GCTGCTGTTT CCCAGCTGGG AGGCTCTGTT

CTCAGGCTCT GAGGGTCCGC TGAAGCCCGG GGCACGCAT

-continued

```
CTTCTCCTTTG ACGGCAAGGA CGTCCTGAGG CACCCCACCT
GGCCCCAGAA GAGCGTGTGGCATGGCTCGG
ACCCCAACGG GCGCAGGCTG ACCGAGAGCT
ACTGTGAGAC GTGGCGGACGGAGGCTCCCT CGGCCACGGG
CCAGGCCTCC TCGCTGCTGG GGGGCAGGCT
CCTGGGGCAG AGTGCCGCGA GCTGCCATCA CGCCTACATC
GTGCTCTGCA TTGAGAACAG CTTCATGACTGCCTCCAAG
```

IGFBP-1

IGFBP-1 is a member of the insulin-like growth factor binding protein (IGFBP) family and encodes a protein with an IGFBP domain and a thyroglobulin type-I domain. The protein binds both insulin-like growth factors (IGFs) I and II and circulates in the plasma. Binding of this protein prolongs the half-life of the IGFs and alters their interaction with cell surface receptors.

An amino acid sequence for human IGFBP-1 is publically available in the UniProt database under accession number P08833 (SEQ ID NO: 26) and is as follows.

```
MSEVPVARVWLVLLLLTVQVGVTAGAPWQCAPCSAEKLALCPPVSASCS
EVTRSAGCGCCPMCALPLGAACGVATARCARGLSCRALPGEQQPLHALT
RGQGACVQESDASAPHAAEAGSPESPESTEITEEELLDNFHLMAPSEED
HSILWDAISTYDGSKALHVTNIKKWKEPCRIELYRVVESLAKAQETSGE
EISKFYLPNCNKNGFYHSRQCETSMDGEAGLCWCVYPWNGKRIPGSPEI
RGDPNCQIYFNVQN
```

A nucleotide sequence that encodes human IGFBP-1 is publically available in the GenBank database under accession number NM_000596.2 (SEQ ID NO: 27) and is as follows (the start and stop codons are underlined and bolded):

```
GGTGCACTAGCAAAACAAACTTATTTTGAACACTCAGCTCCTAGCGTGC
GGCGCTGCCAATCATTAACCTCCTGGTGCAAGTGGCGCGGCCTGTGCCC
TTTATAAGGTGCGCGCTGTGTCCAGCGAGCATCGGCCACCGCCATCCCA
TCCAGCGAGCATCTGCCGCCGCGCCGCCGCCACCCTCCCAGAGAGCACT
GGCCACCGCTCCACCATCACTTGCCCAGAGTTTGGGCCACCGCCCGCCG
CCACCAGCCCAGAGAGCATCGGCCCCTGTCTGCTGCTCGCGCCTGGAGA
TGTCAGAGGTCCCCGTTGCTCGCGTCTGGCTGGTACTGCTCCTGCTGAC
TGTCCAGGTCGGCGTGACAGCCGGCGCTCCGTGGCAGTGCGCGCCCTGC
TCCGCCGAGAAGCTCGCGCTCTGCCCGCCGGTGTCCGCCTCGTGCTCGG
AGGTCACCCGGTCCGCCGGCTGCGGCTGTTGCCCGATGTGCGCCCTGCC
TCTGGGCGCCGCGTGCGGCGTGGCGACTGCACGCTGCGCCCGGGGACTC
AGTTGCCGCGCGCTGCCGGGGGAGCAGCAACCTCTGCACGCCCTCACCC
GCGGCCAAGGCGCCTGCGTGCAGGAGTCTGACGCCTCCGCTCCCCATGC
TGCAGAGGCAGGGAGCCCTGAAAGCCCAGAGAGCACGGAGATAACTGAG
GAGGAGCTCCTGGATAATTTCCATCTGATGGCCCCTTCTGAAGAGGATC
ATTCCATCCTTTGGGACGCCATCAGTACCTATGATGGCTCGAAGGCTCT
CCATGTCACCAACATCAAAAAATGGAAGGAGCCCTGCCGAATAGAACTC
TACAGAGTCGTAGAGAGTTTAGCCAAGGCACAGGAGACATCAGGAGAAG
AAATTTCCAAATTTTACCTGCCAAACTGCAACAAGAATGGATTTTATCA
CAGCAGACAGTGTGAGACATCCATGGATGGAGAGGCGGGACTCTGCTGG
TGCGTCTACCCTTGGAATGGGAAGAGGATCCCTGGGTCTCCAGAGATCA
GGGGAGACCCCAACTGCCAGATATATTTTAATGTACAAAACTGAAACCA
GATGAAATAATGTTCTGTCACGTGAAATATTTAAGTATATAGTATATTT
ATACTCTAGAACATGCACATTTATATATATATGTATATGTATATATATA
TAGTAACTACTTTTTATACTCCATACATAACTTGATATAGAAAGCTGTT
TATTTATTCACTGTAAGTTTATTTTTTCTACACAGTAAAAACTTGTACT
ATGTTAATAACTTGTCCTATGTCAATTTGTATATCATGAAACACTTCTC
ATCATATTGTATGTAAGTAATTGCATTTCTGCTCTTCCAAAGCTCCTGC
GTCTGTTTTTAAAGAGCATGGAAAAATACTGCCTAGAAAATGCAAAATG
AAATAAGAGAGAGTAGTTTTTCAGCTAGTTTGAAGGAGGACGGTTAACT
TGTATATTCCACCATTCACATTTGATGTACATGTGTAGGGAAAGTTAAA
AGTGTTGATTACATAATCAAAGCTACCTGTGGTGATGTTGCCACCTGTT
AAAATGTACACTGGATATGTTGTTAAACACGTGTCTATAATGGAAACAT
TTACAATAAATATTCTGCATGGAAATACTGTTAAAAAAAAAAA
```

HTRA1

HTRA1 is a serine protease with a variety of targets, including extracellular matrix proteins such as fibronectin. HTRA1-generated fibronectin fragments further induce synovial cells to up-regulate matrix metalloproteinase-1 (MMP1) and matrix metalloproteinase-3 (MMP3) production. HTRA1 may also degrade proteoglycans, such as aggrecan, decorin and fibromodulin. Through cleavage of proteoglycans, HTRA1 may release soluble fibroblast growth factor (FGF)-glycosaminoglycan complexes that promote the range and intensity of FGF signals in the extracellular space. HTRA1 is also thought to regulate the availability of insulin-like growth factors (IGFs) by cleaving IGF-binding proteins. HTRA1 is further believed to inhibit signaling mediated by transforming growth factor beta (TGF-β) family members. This activity requires the integrity of the catalytic site, although it is unclear whether TGF-β proteins are themselves degraded. By acting on TGF-β signaling, HTRA1 may regulate many physiological processes, including retinal angiogenesis and neuronal survival and maturation during development. Intracellularly, HTRA1 degrades Tuberous Sclerosis Complex 2 (TSC2), leading to the activation of TSC2 downstream targets.

An amino acid sequence for human HTRA1 is publically available in the UniProt database under accession number Q92743 (SEQ ID NO: 28) and is as follows:

```
MQIPRAALLPLLLLLLAAPASAQLSRAGRSAPLAAGCPDRCEPARCPPQ
PEHCEGGRARDACGCCEVCGAPEGAACGLQEGPCGEGLQCVVPFGVPAS
ATVRRRAQAGLCVCASSEPVCGSDANTYANLCQLRAASRRSERLHRPPV
IVLQRGACGQGQEDPNSLRHKYNFIADVVEKIAPAVVHIELFRKLPFSK
```

-continued

REVPVASGSGFIVSEDGLIVTNAHVVTNKHRVKVELKNGATYEAKIKDV

DEKADIALIKIDHQGKLPVLLLGRSSELRPGEFVVAIGSPFSLQNTVTT

GIVSTTQRGGKELGLRNSDMDYIQTDAIINYGNSGGPLVNLDGEVIGIN

TLKVTAGISFAIPSDKIKKFLTESHDRQAKGKAITKKKYIGIRMMSLTS

SKAKELKDRHRDFPDVISGAYIIEVIPDTPAEAGGLKENDVIISINGQS

VVSANDVSDVIKRESTLNMVVRRGNEDIMITVIPEEIDP

In the sequence shown above, positions 1-22 (SEQ ID NO: 29) correspond to the signal peptide, positions 204-364 (SEQ ID NO: 30) correspond to a serine protease domain.

A nucleotide sequence that encodes human HTRA1 is publically available in the GenBank database under accession number NM_002775.4 (SEQ ID NO: 31) and is as follows (the start and stop codons are underlined and bolded):

CAATGGGCTGGGCCGCGCGGCCGCGCGCACTCGCACCCGCTGCCCCCGA

GGCCCTCCTGCACTCTCCCCGGCGCCGCTCTCCGGCCCTCGCCCTGTCC

GCCGCCACCGCCGCCGCCGCCAGAGTCGCCATGCAGATCCCGCGCGCCG

CTCTTCTCCCGCTGCTGCTGCTGCTGCTGGCGGCGCCCGCCTCGGCGCA

GCTGTCCCGGGCCGGCCGCTCGGCGCCTTTGGCCGCCGGGTGCCCAGAC

CGCTGCGAGCCGGCGCGCTGCCCGCCGCAGCCGGAGCACTGCGAGGGCG

GCCGGGCCCGGGACGCGTGCGGCTGCTGCGAGGTGTGCGGCGCGCCCGA

GGGCGCCGCGTGCGGCCTGCAGGAGGGCCCGTGCGGCGAGGGGCTGCAG

TGCGTGGTGCCCTTCGGGGTGCCAGCCTCGGCCACGGTGCGGCGGCGCG

CGCAGGCCGGCCTCTGTGTGTGCGCCAGCAGCGAGCCGGTGTGCGGCAG

CGACGCCAACACCTACGCCAACCTGTGCCAGCTGCGCGCCGCCAGCCGC

CGCTCCGAGAGGCTGCACCGGCCGCCGGTCATCGTCCTGCAGCGCGGAG

CCTGCGGCCAAGGGCAGGAAGATCCCAACAGTTTGCGCCATAAATATAA

CTTTATCGCGGACGTGGTGGAGAAGATCGCCCCTGCCGTGGTTCATATC

GAATTGTTTCGCAAGCTTCCGTTTTCTAAACGAGAGGTGCCGGTGGCTA

GTGGGTCTGGGTTTATTGTGTCGGAAGATGGACTGATCGTGACAAATGC

CCACGTGGTGACCAACAAGCACCGGGTCAAAGTTGAGCTGAAGAACGGT

GCCACTTACGAAGCCAAAATCAAGGATGTGGATGAGAAAGCAGACATCG

CACTCATCAAAATTGACCACCAGGGCAAGCTGCCTGTCCTGCTGCTTGG

CCGCTCCTCAGAGCTGCGGCCGGGAGAGTTCGTGGTCGCCATCGGAAGC

CCGTTTTCCCTTCAAAACACAGTCACCACCGGGATCGTGAGCACCACCC

AGCGAGGCGGCAAAGAGCTGGGGCTCCGCAACTCAGACATGGACTACAT

CCAGACCGACGCCATCATCAACTATGGAAACTCGGGAGGCCCGTTAGTA

AACCTGGACGGTGAAGTGATTGGAATTAACACTTTGAAAGTGACAGCTG

GAATCTCCTTTGCAATCCCATCTGATAAGATTAAAAAGTTCCTCACGGA

GTCCCATGACCGACAGGCCAAAGGAAAAGCCATCACCAAGAAGAAGTAT

ATTGGTATCCGAATGATGTCACTCACGTCCAGCAAAGCCAAAGAGCTGA

AGGACCGGCACCGGGACTTCCCAGACGTGATCTCAGGAGCGTATATAAT

-continued

TGAAGTAATTCCTGATACCCCAGCAGAAGCTGGTGGTCTCAAGGAAAAC

GACGTCATAATCAGCATCAATGGACAGTCCGTGGTCTCCGCCAATGATG

TCAGCGACGTCATTAAAAGGGAAAGCACCCTGAACATGGTGGTCCGCAG

GGGTAATGAAGATATCATGATCACAGTGATTCCCGAAGAAATTGACCCA

TAGGCAGAGGCATGAGCTGGACTTCATGTTTCCCTCAAAGACTCTCCCG

TGGATGACGGATGAGGACTCTGGGCTGCTGGAATAGGACACTCAAGACT

TTTGACTGCCATTTTGTTTGTTCAGTGGAGACTCCCTGGCCAACAGAAT

CCTTCTTGATAGTTTGCAGGCAAAACAAATGTAATGTTGCAGATCCGCA

GGCAGAAGCTCTGCCCTTCTGTATCCTATGTATGCAGTGTGCTTTTTCT

TGCCAGCTTGGGCCATTCTTGCTTAGACAGTCAGCATTTGTCTCCTCCT

TTAACTGAGTCATCATCTTAGTCCAACTAATGCAGTCGATACAATGCGT

AGATAGAAGAAGCCCCACGGGAGCCAGGATGGGACTGGTCGTGTTTGTG

CTTTTCTCCAAGTCAGCACCCAAAGGTCAATGCACAGAGACCCCGGGTG

GGTGAGCGCTGGCTTCTCAAACGGCCGAAGTTGCCTCTTTTAGGAATCT

CTTTGGAATTGGGAGCACGATGACTCTGAGTTTGAGCTATTAAAGTACT

TCTTACACATTGCAAAAAAAAAAAAAAAAAA

Exemplary SVDs and the Treatment Thereof

Aspects of the present subject matter relate to the treatment of SVDs. Non-limiting examples of SVDs are discussed below.

Cerebral Small Vessel Disease

As used herein, the term "cerebral small vessel disease" or "cerebral SVD" refers to a group of pathological processes with various aetiologies that affect the small arteries, arterioles, venules, and capillaries of the brain. See, e.g., Pantoni (2010) Lancet Neurol, 9(7):689-701, the entire contents of which are incorporated herein by reference. Age-related and hypertension-related SVDs and cerebral amyloid angiopathy are the most common forms. The consequences of small vessel disease on the brain parenchyma are mainly lesions located in the subcortical structures such as lacunar infarcts, white matter lesions, large hemorrhages, and microbleeds. Small vessel disease has an important role in cerebrovascular disease and is a leading cause of cognitive decline and functional loss in the elderly.

Cerebral SVD may lead to vascular dementia (also known as vascular cognitive impairment). In vascular dementia, changes in thinking skills sometimes occur suddenly following strokes that block major brain blood vessels. See, e.g., Alzheimer's Association, Alzheimer's & Dementia, available at www.alz.org/dementia/vascular-dementia-symptoms.asp, the entire contents of which are incorporated herein by reference. Thinking problems also may begin as mild changes that worsen gradually as a result of multiple minor strokes or other conditions that affect smaller blood vessels, leading to cumulative damage. Symptoms can vary widely, depending on the severity of the blood vessel damage and the part of the brain affected. Memory loss may or may not be a significant symptom depending on the specific brain areas where blood flow is reduced. Vascular dementia symptoms may be most obvious when they happen soon after a major stroke. Sudden post-stroke changes in thinking and perception may include, e.g., (i) confusion; (ii) disorientation; (iii) trouble speaking or understanding speech; and/or (iv) vision loss. These changes may happen at the same time as stroke symptoms such as a sudden headache, difficulty walking, or numbness or paralysis on one side of the face or the body.

Multiple small strokes or other conditions that affect blood vessels and nerve fibers deep inside the brain may cause more gradual thinking changes as damage accumulates. Common early signs of widespread small vessel disease include impaired planning and judgment; uncontrolled laughing and crying; declining ability to pay attention; impaired function in social situations; and difficulty finding the right words.

The present subject matter provides methods for treating each subtype, symptom, and/or complication of cerebral SVD.

HTRA1-Associated Small Vessel Disease

As used herein, an "HTRA1-associated small vessel disease" or HTRA1-associated SVD is a SVD that results from a dominant HTRA1 mutation. In various embodiments, a subject is heterozygous for the mutation. Descriptions of exemplary heterozygous mutations of the HTRA1 gene in patients with familial cerebral small vessel disease are included in Donato et al. 2017 "Heterozygous mutations of HTRA1 gene in patients with familial cerebral small vessel disease" *CNS Neurosci Ther.* 23(9):759-765; and Verdura et al. (2015) "Heterozygous HTRA1 mutations are associated with autosomal dominant cerebral small vessel disease" *Brain* 138; 2347-2358, the entire contents of each of which are incorporated herein by reference.

Cerebral Autosomal Recessive Arteriopathy with Subcortical Infarcts and Leukoencephalopathy Cerebral autosomal recessive arteriopathy with subcortical infarcts and leukoencephalopathy, commonly known as CARASIL, is an inherited condition that causes stroke and other impairments. As its name suggests, this condition is inherited in an autosomal recessive pattern. Autosomal recessive inheritance means both copies of the gene in each cell have mutations. The parents of an individual with an autosomal recessive condition each carry one copy of the mutated gene, but they typically do not show signs and symptoms of the condition. See, e.g., the U.S. National Library of Medicine Genetics Home Reference, CARASIL, available at ghr.nlm.nih.gov/condition/cerebral-autosomal-recessive-arteriopathy-with-subcortical-infarcts-and-leukoencephalopathy#inheritance, the entire contents of which are incorporated herein by reference.

Abnormalities affecting the brain and other parts of the nervous system become apparent in an affected person's twenties or thirties. Often, muscle stiffness (spasticity) in the legs and problems with walking are the first signs of the disorder. About half of affected individuals have a stroke or similar episode before age 40. As the disease progresses, most people with CARASIL also develop mood and personality changes, a decline in thinking ability (dementia), memory loss, and worsening problems with movement.

Other characteristic features of CARASIL include premature hair loss (alopecia) and attacks of low back pain. The hair loss often begins during adolescence and is limited to the scalp. Back pain, which develops in early to mid-adulthood, results from the breakdown (degeneration) of the discs that separate the bones of the spine (vertebrae) from one another.

The signs and symptoms of CARASIL worsen slowly with time. Over the course of several years, affected individuals become less able to control their emotions and communicate with others. They increasingly require help with personal care and other activities of daily living; after a few years, they become unable to care for themselves. Most affected individuals die within a decade after signs and symptoms first appear, although few people with the disease have survived for 20 to 30 years.

The present subject matter provides methods for treating each subtype, symptom, and/or complication of CARASIL.

Cerebral Autosomal-Dominant Arteriopathy with Subcortical Infarcts and Leukoencephalopathy Cerebral autosomal dominant arteriopathy with subcortical infarcts and leukoencephalopathy, usually called CADASIL, is an inherited condition that causes stroke and other impairments. This condition affects blood flow in small blood vessels, particularly cerebral vessels within the brain. The muscle cells surrounding these blood vessels (vascular smooth muscle cells) are abnormal and gradually die. In the brain, the resulting blood vessel damage (arteriopathy) can cause migraines, often with visual sensations or auras, or recurrent seizures (epilepsy). See, e.g., the U.S. National Library of Medicine Genetics Home Reference, CADASIL, available at ghr.nlm.nih.gov/condition/cerebral-autosomal-dominant-arteriopathy-with-subcortical-infarcts-and-leukoencephalopathy#genes, the entire contents of which are incorporated herein by reference.

Damaged blood vessels reduce blood flow and can cause areas of tissue death (infarcts) throughout the body. An infarct in the brain can lead to a stroke. In individuals with CADASIL, a stroke can occur at any time from childhood to late adulthood, but typically happens during mid-adulthood. People with CADASIL often have more than one stroke in their lifetime. Recurrent strokes can damage the brain over time. Strokes that occur in the subcortical region of the brain, which is involved in reasoning and memory, can cause progressive loss of intellectual function (dementia) and changes in mood and personality.

Many people with CADASIL also develop leukoencephalopathy, which is a change in a type of brain tissue called white matter that can be seen with magnetic resonance imaging (MRI).

The age at which the signs and symptoms of CADASIL first begin varies greatly among affected individuals, as does the severity of these features.

CADASIL is not associated with the common risk factors for stroke and heart attack, such as high blood pressure and high cholesterol, although some affected individuals might also have these health problems.

Prior to the present invention, no specific treatment was available for CADASIL. However, anti-platelet agents such as aspirin, dipyridamole, ticlopidine, and clopidogrel are used to slow down the disease and help prevent strokes. Aspects of the present invention relate to administering an anti-platelet agent to a subject who is diagnosed with or determined to be at risk of developing CADASIL. In some embodiments, the subject receives therapy for primary or secondary prevention of stroke and myocardial infarction. Risk-reduction measures in primary stroke prevention may include the use of antihypertensive medications; platelet antiaggregants; 3-hydroxy-3-methylglutaryl coenzyme A (HMG-CoA) reductase inhibitors (statins); smoking cessation; dietary intervention; weight loss; and exercise. Secondary prevention may include the use of antiaggregants (aspirin, clopidogrel, extended-release dipyridamole, ticlopidine), cholesterol-reducing medications, and/or blood pressure-lowering medications, as well as the cessation of cigarette smoking, improving the diet (e.g., reducing red meat consumption and/or increasing vegetable consumption), and increased exercise.

The present subject matter provides methods for treating each subtype, symptom, and/or complication of CADASIL.

NOTCH3 Loss of Function-Associated Small Vessel Disease

NOTCH3 loss of function mutations cause an SVD phenotype strikingly similar to CADASIL but with key differences including the lack of accumulation of the NOTCH3 extracellular domain and the lack of GOM deposits. Typical mutations include changes leading to NOTCH 3 frame shifts, premature stop codons, or splicing defects. Partial or complete gene deletions or promoter or enhancer mutations leading to lower than normal NOTCH3 expression are also included. It has been reported that in some patients, typical CADASIL mutations also lead to NOTCH3 loss of function and in these, NOTCH3 loss of function contributes to SVD pathology. In most cases, patients with NOTCH3 loss of function are heterozygotes although a homozygote patient has been reported with earlier age at onset of SVD. This indicates that NOTCH3 is haploinsufficient in humans because one wild type copy of the gene is not sufficient to produce a wild type phenotype. Conditions that may indirectly lead to a decrease in NOTCH3 expression or function in the absence of mutations include cardiovascular, metabolic disease, disease, environmental factor, and aging.

Age-Related Macular Degeneration

Age-related macular degeneration (AMD) is an eye disease that is a leading cause of vision loss in older people in developed countries. The vision loss usually becomes noticeable in a person's sixties or seventies and tends to worsen over time. See, e.g., the U.S. National Library of Medicine Genetics Home Reference, Age-Related Macular Degeneration, available at ghr.nlm.nih.gov/condition/age-related-macular-degeneration, the entire contents of which are incorporated herein by reference.

AMD mainly affects central vision, which is needed for detailed tasks such as reading, driving, and recognizing faces. The vision loss in this condition results from a gradual deterioration of light-sensing cells in the tissue at the back of the eye that detects light and color (the retina). Specifically, age-related macular degeneration affects a small area near the center of the retina, called the macula, which is responsible for central vision. Side (peripheral) vision and night vision are generally not affected.

There are two major types of AMD, known as the dry form and the wet form. The dry form is much more common, accounting for 85 to 90 percent of all cases of age-related macular degeneration. It is characterized by a buildup of yellowish deposits called drusen beneath the retina and slowly progressive vision loss. The condition typically affects vision in both eyes, although vision loss often occurs in one eye before the other.

The wet form of AMD is associated with severe vision loss that can worsen rapidly. This form of the condition is characterized by the growth of abnormal, fragile blood vessels underneath the macula. These vessels leak blood and fluid, which damages the macula and makes central vision appear blurry and distorted.

AMD results from a combination of genetic and environmental factors. Many of these factors have been identified, but some remain unknown.

Without wishing to be bound by any scientific theory, changes in many genes may be risk factors for age-related macular degeneration. The best-studied of these genes are involved in a part of the body's immune response known as the complement system. This system is a group of proteins that work together to destroy foreign invaders (such as bacteria and viruses), trigger inflammation, and remove debris from cells and tissues. Genetic changes in and around several complement system genes, including the complement factor H (CFH) gene, contribute to a person's risk of developing age-related macular degeneration. It is unclear how these genetic changes are related to the retinal damage and vision loss characteristic of this condition. Changes on the long (q) arm of chromosome 10 in a region known as 10q26 are also associated with an increased risk of age-related macular degeneration. The 10q26 region contains two genes of interest, age-related maculopathy susceptibility 2 (ARMS2) and high-temperature requirement A serine peptidase 1 (HTRA1). Changes in both genes have been studied as possible risk factors for the disease. However, because the two genes are so close together, it is difficult to tell which gene is associated with age-related macular degeneration risk, or whether increased risk results from variations in both genes. An estimated 15 to 20 percent of people with age-related macular degeneration have at least one first-degree relative (such as a sibling) with the condition. Other genes that are associated with age-related macular degeneration include genes involved in transporting and processing high-density lipoprotein (HDL) and genes that have been associated with other forms of macular disease.

Nongenetic factors that contribute to the risk of age-related macular degeneration are also known. Age appears to be the most important risk factor; the chance of developing the condition increases significantly as a person gets older. Smoking is another established risk factor for age-related macular degeneration.

Aspects of the present subject matter relate to administering a treatment for AMD to a subject who is diagnosed with or determined to be at risk of developing AMD. In some embodiments, the subject is administered a statin. In some embodiments relating to neovascular AMD, the subject is administered an antiangiogenic steroid such as anecortave acetate or triamcinolone acetonide. In various embodiments relating to wet AMD, the subject can be treated with laser coagulation or a medication that stops and sometimes reverses the growth of blood vessels. In certain embodiments, the subject is treated with bevacizumab, ranibizumab, pegaptanib, or aflibercept. In some embodiments, photodynamic therapy is administered to the subject. For example, the drug verteporfin is administered intravenously and light of a certain wavelength (e.g., 689 nm) is then applied to the abnormal blood vessels, which activates the verteporfin to destroy the vessels.

The present subject matter provides diagnostic, prognostic, treatment, and monitoring methods, as well as related compositions, kits, and systems, for each subtype, symptom, and/or complication of AMD.

Retinopathy

Retinopathy is persistent or acute damage to the retina of the eye. Ongoing inflammation and vascular remodeling may occur over periods of time where the patient is not fully aware of the extent of the disease. Frequently, retinopathy is an ocular manifestation of systemic disease as seen in diabetes or hypertension. Diabetic retinopathy is the leading cause of blindness in working-aged people.

Causes of retinopathy include but are not limited to: (i) diabetes mellitus, which can cause diabetic retinopathy; (ii) arterial hypertension, which can cause hypertensive retinopathy; (iii) retinopathy of prematurity due to prematurity of a newborn (under the 9 months of human pregnancy); (iv) radiation retinopathy due to exposure to ionizing radiation; (v) solar retinopathy due to direct sunlight exposure; (vi) sickle cell disease; (vii) retinal vascular disease such as retinal vein or artery occlusion; (viii) trauma, especially to the head, and several diseases may cause Purtscher's retinopathy; and (ix) hyperviscosity-related retinopathy as seen in disorders which cause paraproteinemia.

Many types of retinopathy are proliferative, most often resulting from neovascularization or blood vessel overgrowth. Angiogenesis is the hallmark precursor that may result in blindness or severe vision loss, particularly if the macula becomes affected. Retinopathy may also be a symptom or complication of a ciliopathic genetic disorder such as Alström syndrome or Bardet-Biedl syndrome.

Aspects of the present subject matter relate to administering a treatment for retinopathy to a subject who is diagnosed with or determined to be at risk of developing retinopathy. Treatment may include laser therapy to the retina and/or the administration of a vascular endothelial growth factor (VEGF) inhibitor.

The present subject matter provides methods for the treatment of each subtype, symptom, and/or complication of retinopathy.

Microangiopathy

Microangiopathy (or microvascular disease, or small vessel disease) is an angiopathy (i.e. disease of blood vessels) affecting small blood vessels in the body. The condition can occur in any organ of the body. One cause of microangiopathy is long-term diabetes mellitus. In this case, high blood glucose levels cause the endothelial cells lining the blood vessels to take in more glucose than normal (these cells do not depend on insulin). They then form more glycoproteins on their surface than normal, and also cause the basement membrane in the vessel wall to grow abnormally thicker and weaker. Mural cell loss is also a hallmark of microangiopathy and is associated with hyperglycemia. Therefore vessels bleed, leak protein, and slow the flow of blood through the body. As a result, some organs and tissues do not get enough blood (carrying oxygen & nutrients) and are damaged, for example, the retina (diabetic retinopathy) or kidney (diabetic nephropathy). Nerves and neurons, if not sufficiently supplied with blood, are also damaged, which leads to loss of function (diabetic neuropathy, especially peripheral neuropathy).

Massive microangiopathy may cause microangiopathic hemolytic anemia (MAHA).

The present subject matter provides methods for the treatment of each subtype, symptom, and/or complication of microangiopathy.

Nephropathy and Small Vessel Diseases of the Kidney

SVD can occur in the kidneys during or as part of nephropathy. For example, diabetic nephropathy (or diabetic kidney disease) is a progressive kidney disease caused by damage to the capillaries in the kidneys' glomeruli. It is characterized by nephrotic syndrome and diffuse scarring of the glomeruli. It is due to longstanding diabetes mellitus, and is a prime reason for dialysis in many developed countries. It is classified as a small blood vessel complication of diabetes. During its early course, diabetic nephropathy often has no symptoms. Symptoms can take 5 to 10 years to appear after the kidney damage begins. These late symptoms include severe tiredness, headaches, a general feeling of illness, nausea, vomiting, frequent voiding, lack of appetite, itchy skin, and leg swelling.

The present subject matter provides methods for the treatment of each subtype, symptom, and/or complication of nephropathy.

Proximal 19p13.12 Microdeletion Syndrome

In embodiments, the SVD comprises proximal 19p13.12 microdeletion syndrome. Non-limiting descriptions relating to this syndrome are provided in Huynh et al. (2018) "First prenatal case of proximal 19p13.12 microdeletion syndrome: New insights and new delineation of the syndrome" *Eur J Med Genet. S*1769-7212(17)30466-4, the entire content of which is incorporated herein by reference.

In certain embodiments, proximal 19p13.12 microdeletion syndrome comprises intellectual disability, facial dysmorphism, and/or branchial arch defects. In some embodiments, proximal 19p13.12 microdeletion syndrome comprises hypertrichosis-synophrys-protruding front teeth. In various embodiments, a subject with proximal 19p13.12 microdeletion syndrome comprises a heterozygous interstitial deletion at 19p13.12 chromosome region. In certain embodiments, the deletion is a deletion of about 350 kb to about 750 kb. In some embodiments, the deletion is a deletion of about 745 kb. In various embodiments, the deletion includes at least a portion of the NOTCH3 gene. In certain embodiments, the deletion includes the entire NOTCH3 gene. In some embodiments, the deletion comprises (e.g., in addition to a mutation in part of all of the NOTCH3 gene) a portion of, or the entirety of any one of, any combination of the following genes: SYDE1, AKAP8, AKAP8L, WIZ and BRD4.

The present subject matter provides methods for the treatment of each subtype, symptom, and/or complication of proximal 19p13.12 microdeletion syndrome.

Myocardial Ischemia

NOTCH3 deficiency impairs coronary microvascular maturation and reduces cardiac recovery after myocardial ischemia. See, e.g., Tao et al. (2017) "Notch3 deficiency impairs coronary microvascular maturation and reduces cardiac recovery after myocardial ischemia" Int J Cardiol. 2017 Jun. 1; 236:413-422, the entire content of which is incorporated herein by reference. In various embodiments, a subject with myocardial ischemia has myocardial infarction.

In certain embodiments, reduced NOTCH3 results in a reduction of pericytes and small arterioles. In some embodiments, the reduction in pericytes and small arterioles increases the severity of myocardial ischemia, and/or reduces cardiac recovery after myocardial ischemia. In various embodiments, a subject with reduced NOTCH3 function (e.g., due to a mutation) is prone to ischemic injury with larger infarcted size and higher rates of mortality. In certain embodiments, the expression of CXCR-4 and VEGF/Ang-1 is decreased in a subject with reduced NOTCH3 function. In some embodiments, a subject with reduced NOTCH3 function has fewer NG2+/Scal+ and NG2+/c-kit+ progenitor cells in an ischemic area and exhibits worse cardiac function recovery at 2 weeks after myocardial ischemia compared to a corresponding subject with a normal level of NOTCH3 function. In certain embodiments, a subject with reduced NOTCH3 function has a significant reduction of pericyte/capillary coverage and arteriolar maturation compared to a corresponding subject with a normal level of NOTCH3 function. In various embodiments, a subject with a reduced level of NOTCH3 function and who has had myocardial ischemia has increased intracellular adhesion molecule-2 (ICAM-2) expression and CD11b+ macrophage infiltration into ischemic areas compared to that of a corresponding subject with a normal level of NOTCH3 function. In embodiments, a subject has a NOTCH3 mutation that impairs recovery of cardiac function post-myocardial ischemia by the mechanisms involving the pre-existing coronary microvascular dysfunction conditions, and impairment of pericyte/progenitor cell recruitment and microvascular maturation.

The present subject matter provides methods for the treatment of each subtype, symptom, and/or complication of myocardial ischemia.

Heart Failure

Heart failure is a chronic, progressive condition in which the heart muscle is unable to pump enough blood through to meet the body's needs for blood and oxygen. Loss of NOTCH3 signaling in vascular smooth muscle cells promotes severe heart failure upon hypertension. See, e.g., Ragot et al., (2016) Hypertension. 68(2):392-400; and the American Heart Association, What is Heart Failure? available at www.heart.org/HEARTORG/Conditions/HeartFailure/AboutHeartFailure/About-Heart-Failure_UCM_002044_Article.jsp#.WM16W_7lva8, the entire contents of each of which are incorporated herein by reference.

The heart tries to make up for this by enlarging, developing more muscle mass, and/or pumping faster. When the heart chamber enlarges, it stretches more and can contract more strongly, so it pumps more blood. With an enlarged heart, the body starts to retain fluid, the lungs get congested with fluid and the heart begins to beat irregularly. An increase in muscle mass occurs because the contracting cells of the heart get bigger. This lets the heart pump more strongly, at least initially. Increased heartrate helps to increase the heart's output.

The body also tries to compensate in other ways: (i) The blood vessels narrow to keep blood pressure up, trying to make up for the heart's loss of power; and (ii) The body diverts blood away from less important tissues and organs (like the kidneys), the heart and brain.

These temporary measures mask the problem of heart failure, but they do not solve it. Heart failure continues and worsens until these substitute processes no longer work. Eventually the subject experiences the fatigue, breathing problems or other symptoms that usually prompt a trip to the doctor.

Heart failure can involve the heart's left side, right side or both sides. However, it usually affects the left side first.

The present subject matter provides methods for the treatment of each subtype, symptom, and/or complication of heart failure.

Alagille Syndrome and Familial Tetralogy of Fallot

Alagille syndrome is a genetic disorder that can affect the liver, heart, and other parts of the body. See, e.g., the U.S. National Library of Medicine Genetics Home Reference, Alagille syndrome, available at ghr.nlm.nih.gov/condition/alagille-syndrome, the entire contents of which are incorporated herein by reference.

One of the major features of Alagille syndrome is liver damage caused by abnormalities in the bile ducts. These ducts carry bile (which helps to digest fats) from the liver to the gallbladder and small intestine. In Alagille syndrome, the bile ducts may be narrow, malformed, and reduced in number (bile duct paucity). As a result, bile builds up in the liver and causes scarring that prevents the liver from working properly to eliminate wastes from the bloodstream. Signs and symptoms arising from liver damage in Alagille syndrome may include a yellowish tinge in the skin and the whites of the eyes (jaundice), itchy skin, and deposits of cholesterol in the skin (xanthomas).

Alagille syndrome is also associated with several heart problems, including impaired blood flow from the heart into the lungs (pulmonic stenosis). Pulmonic stenosis may occur along with a hole between the two lower chambers of the heart (ventricular septal defect) and other heart abnormalities. This combination of heart defects is called tetralogy of Fallot.

People with Alagille syndrome may have distinctive facial features including a broad, prominent forehead; deep-set eyes; and a small, pointed chin. The disorder may also affect the blood vessels within the brain and spinal cord (central nervous system) and the kidneys. Affected individuals may have an unusual butterfly shape of the bones of the spinal column (vertebrae) that can be seen in an x-ray.

Problems associated with Alagille syndrome generally become evident in infancy or early childhood. The severity of the disorder varies among affected individuals, even within the same family. Symptoms range from so mild as to go unnoticed to severe heart and/or liver disease requiring transplantation.

Some people with Alagille syndrome may have isolated signs of the disorder, such as a heart defect like tetralogy of Fallot, or a characteristic facial appearance. These individuals do not have liver disease or other features typical of the disorder.

In more than 90 percent of cases, mutations in the JAGGED1 gene cause Alagille syndrome. Another 7 percent of individuals with Alagille syndrome have small deletions of genetic material on chromosome 20 that include the JAG1 gene, which encodes JAGGED1. A few people with Alagille syndrome have mutations in a different gene, called NOTCH2. The JAG1 and NOTCH2 genes provide instructions for making proteins that fit together to trigger interactions called Notch signaling between neighboring cells during embryonic development. This signaling influences how the cells are used to build body structures in the developing embryo. Changes in either the JAG1 gene or NOTCH2 gene probably disrupt the Notch signaling pathway. As a result, errors may occur during development, especially affecting the bile ducts, heart, spinal column, and certain facial features.

The present subject matter provides methods for the treatment of each subtype, symptom, and/or complication of Alagille syndrome and/or familial tetralogy of Fallot.

Patent Ductus Arteriosus

Patent ductus arteriosus (PDA) is a condition wherein the ductus arteriosus fails to close after birth. Early symptoms are uncommon, but in the first year of life include increased work of breathing and poor weight gain. An uncorrected PDA may lead to congestive heart failure with increasing age.

The ductus arteriosus is a fetal blood vessel that closes soon after birth. In a PDA, the vessel does not close and remains "patent" (open), resulting in irregular transmission of blood between the aorta and the pulmonary artery. PDA is common in newborns with persistent respiratory problems such as hypoxia, and has a high occurrence in premature newborns. Premature newborns are more likely to be hypoxic and have PDA due to underdevelopment of the heart and lungs.

A PDA allows a portion of the oxygenated blood from the left heart to flow back to the lungs by flowing from the aorta (which has higher pressure) to the pulmonary artery. If this shunt is substantial, the neonate becomes short of breath: the additional fluid returning to the lungs increases lung pressure, which in turn increases the energy required to inflate the lungs. This uses more calories than normal and often interferes with feeding in infancy. This condition, as a constellation of findings, is called congestive heart failure.

In some congenital heart defects (such as in transposition of the great vessels) a PDA may need to remain open, as it is the only way that oxygenated blood can mix with deoxygenated blood. In these cases, prostaglandins are used to keep the DA open until surgical correction of the heart defect is completed.

PDA is associated with NOTCH3 loss of function. See, e.g., Baeten et al., (2015) Genesis 53(12):738-48, the entire content of which is incorporated herein by reference.

The present subject matter provides methods for the treatment of each subtype, symptom, and/or complication of PDA.

Cerebral Cavernous Malformations

Cerebral cavernous malformations are collections of small blood vessels (capillaries) in the brain that are enlarged and irregular in structure. These capillaries have abnormally thin walls, and they lack other support tissues, such as elastic fibers, which normally make them stretchy. See, e.g., the U.S. National Library of Medicine Genetics Home Reference, Cerebral Cavernous Malformation, available at ghr.nlm.nih.gov/condition/cerebral-cavernous-malformation, the entire contents of which are incorporated herein by reference. As a result, the blood vessels are prone to leakage, which can cause the health problems related to this condition. Cavernous malformations can occur anywhere in the body, but usually produce serious signs and symptoms only when they occur in the brain and spinal cord (which are described as cerebral).

Approximately 25 percent of individuals with cerebral cavernous malformations never experience any related health problems. Other people with this condition may experience serious signs and symptoms such as headaches, seizures, paralysis, hearing or vision loss, and bleeding in the brain (cerebral hemorrhage). Severe brain hemorrhages can result in death. The location and number of cerebral cavernous malformations determine the severity of this disorder. These malformations can change in size and number over time.

There are two forms of the condition: familial and sporadic. The familial form is passed from parent to child, and affected individuals typically have multiple cerebral cavernous malformations. The sporadic form occurs in people with no family history of the disorder. These individuals typically have only one malformation.

Defective NOTCH3 signaling is associated with cerebral cavernous malformations. See, e.g., Schultz et al. (2015) Stroke 46(5):1337-43, the entire content of which is incorporated herein by reference.

The present subject matter provides methods for the treatment of each subtype, symptom, and/or complication of cerebral cavernous malformation.

Lacunar Strokes and Hemorrhagic Strokes

As disclosed herein, the consequences of SVD on the brain parenchyma are mainly lesions located in the subcortical structures such as lacunar infarcts (also termed "lacunar strokes"), white matter lesions, large hemorrhages, and microbleeds. Strokes, such as lacunar strokes and hemorrhagic strokes, are signs of (e.g., may result from) a SVD. A lacunar stroke is the most common type of stroke, and results from the occlusion of one or more small penetrating arteries that provide blood to the brain's deep structures. In some embodiments, a lacunar stroke comprises a small infarct (2-20 mm in diameter) in the deep cerebral white matter, basal ganglia, or pons, presumed to result from the occlusion of a single small perforating artery supplying the subcortical areas of the brain. Hemorrhagic strokes (bleeds) result from a weakened vessel that ruptures and bleeds into the surrounding brain. Pericytes have been reported to play different roles during the different phases of ischemic stroke (e.g., lacunar stroke). See, e.g., Yang et al. (2017), *Curr Neuropharmacol* 15(6): 892-905, the entire content of which is incorporated herein by reference. In some embodiments, pericyte constriction and death may be a cause of the no-reflow phenomenon in brain capillaries during the hyperacute phase of stroke. In certain embodiments, during the acute phase, pericytes detach from microvessels and participate in inflammatory-immunological response, resulting in blood brain barrier (BBB) damage and brain edema. In various embodiments, pericytes are neuroprotective by protecting endothelium, stabilizing BBB and releasing neurotrophins. In some embodiments, pericytes contribute to angiogenesis and neurogenesis, and thereby promote neurological recovery during the recovery phase of stroke.

In certain embodiments, a subject with a SVD has more difficulty recovering from a lacunar stroke. In some embodiments, a subject with a SVD has more difficulty recovering from a hemorrhagic stroke. In various embodiments, a treatment herein improves (e.g., the rate or degree of) treatment in a subject with a SVD who has had a lacunar stroke or a hemorrhagic stroke. In certain embodiments, a treatment herein reduces the likelihood that a subject who has a SVD will have a lacunar stroke or a hemorrhagic stroke. In various embodiments, NOTCH3 signaling manipulation (e.g., increasing NOTCH3 signaling) can stabilize mural cells after stroke (e.g., during the different phases after stroke).

The present subject matter provides methods for the treatment of each subtype, symptom, and/or complication of lacunar strokes and hemorrhagic strokes.

Subjects at Risk of Developing a Small Vessel Disease or a Symptom or Complication of a Small Vessel Disease Aspects of the present subject matter relate to inhibiting or preventing a SVD (or a complication or symptom thereof) in a subject who is at risk of developing the SVD (or a symptom or complication thereof). In some embodiments, a subject at risk of developing an SVD or a symptom or complication thereof is administered a therapeutic treatment for the SVD prior to the subject's diagnosis or perception of the SVD or a symptom or complication of the SVD.

Risk factors may vary from SVD to SVD. However, a subject may generally be considered to be at risk of suffering from a SVD or a symptom or complication thereof if the subject has at least 1 grandparent, parent, aunt, uncle, cousin, and/or sibling who suffers from the SVD or the symptom or complication thereof. Additional non-limiting examples of risk factors for SVDs are discussed below.

Cerebral SVD has frequently been found on computed tomography (CT) and magnetic resonance imaging (MRI) scans of elderly people. See, e.g., van Norden et al., (2011) BMC NeurologyBMC series 11:29, the entire contents of which are incorporated herein by reference. In various embodiments, an elderly subject (e.g., a subject who is at least about 70, 75, 80, 85, 90, or 95 years old) is deemed to be at risk of and treated and/or screened for (e.g., using a diagnostic or prognostic method disclosed herein) cerebral SVD and/or a complication or symptom of cerebral SVD. Symptoms and complications of cerebral SVD are disclosed herein and include, e.g., vascular cognitive impairment, hemorrhages and microbleeds, neuropathy, strokes, dementia, and/or parkinsonism. In various embodiments, a subject at risk of developing cerebral SVD or a complication or symptom thereof is a subject who has suffered from at least one stroke. In certain embodiments, a subject is at risk of developing cerebral SVD or a complication or symptom thereof if the subject has hypertension (e.g., a systolic pressure of at least 140 mmHg or a diastolic pressure of at least 90 mmHg) and/or amyloid deposits in the walls of the blood vessels of the central nervous system. There are also hereditary risk factors for cerebral SVD. See, e.g., Plancher et al. Case Rep Neurol. 2015 May-August; 7(2): 142-147, the entire contents of which are incorporated herein by reference. In some embodiments, the subject has a mutated gene that is associated with cerebral SVD. In certain embodiments, a subject is at risk of developing cerebral SVD if the subject has at least 1 grandparent, parent, aunt, uncle, cousin, or sibling who suffers or has suffered from cerebral SVD or a complication or symptom thereof, and/or who has a gene mutation that is associated with cerebral SVD.

In some embodiments, the subject (or at least 1 grandparent, parent, aunt, uncle, cousin, and/or sibling thereof) has a mutation in a COL4A1 gene (which encodes the type IV collagen alpha-1 chain). COL4A1-related brain SVD is part of a group of conditions called the COL4A1-related disorders. See, e.g., the U.S. National Library of Medicine Genetics Home Reference, COL4A1-related brain small-vessel disease, available at ghr.nlm.nih.gov/condition/col4a1-related-brain-small-vessel-disease#genes, the entire contents of which are incorporated herein by reference. The conditions in this group have a range of signs and symptoms that involve fragile blood vessels. COL4A1-related brain small-vessel disease is characterized by weakening of the blood vessels in the brain. Stroke is often the first symptom of this condition, typically occurring in mid-adulthood. In affected individuals, stroke is usually caused by bleeding in the brain (hemorrhagic stroke) rather than a lack of blood flow in the brain (ischemic stroke), although either type can occur. Individuals with this condition are at increased risk of having more than one stroke in their lifetime. People with COL4A1-related brain small vessel disease also have leukoencephalopathy, which is a change in a type of brain tissue called white matter that can be seen with MRI. Affected individuals may also experience seizures and migraine headaches accompanied by visual sensations known as auras. In various embodiments, a subject with a COL4A1 mutation is at risk of and treated and/or screened for (e.g., using a diagnostic or prognostic method disclosed herein) for a symptom or complication such as a ischemic stroke, a hemorrhagic stroke, a migraine, a seizure, leukomalacia, nephropathy, hematuria, chronic muscle cramps, and/or a ocular anterior segment disease.

In some embodiments, a subject is at risk of cerebral SVD (e.g., sporadic cerebral SVD). In certain embodiments, the subject (or at least 1 grandparent, parent, aunt, uncle, cousin, and/or sibling thereof) has a mutation in a COL4A2 gene. COL4A2 is associated with lacunar ischemic stroke and deep intracerebral hemorrhage (ICH). See, e.g., Rannikmae et al. (2017) "COL4A2 is associated with lacunar ischemic stroke and deep ICH: Meta-analyses among 21,500 cases and 40,600 controls" *Neurology October* 24; 89(17):1829-1839.

In embodiments, subjects at risk of ICH (e.g., deep or lobar ICH) and/or ischemic stroke (IS) (e.g., lacunar, cardioembolic, or large vessel disease) include subjects with a mutation in a COL4A1 or COL4A2 gene.

Subjects at risk of developing CARASIL or CADASIL and/or a symptom or complication thereof include subjects with at least 1 or 2 grandparents, parents, or siblings who suffer from CARASIL, or CADASIL, and/or the symptom or complication thereof. Subjects at risk of developing CARASIL also include subjects who carry a mutation in the HTRA1 gene, or who have a grandparent, parent, or sibling who carries such a mutation. Subjects at risk of developing CADASIL also include subjects who carry a mutation in the NOTCH3 gene, or who have a grandparent, parent, or sibling who carries such a mutation.

Subjects at risk of developing AMD (such as wet or dry AMD) and/or a symptom or complication thereof include subjects with high blood pressure, heart disease, a high-fat diet or one that is low in certain nutrients (such as antioxidants and zinc), obesity, repeated and/or prolonged exposure to ultraviolet (UV) rays from sunlight, or who smoke or have smoked for at least about 1, 5, 10, or more years. Subjects at risk of developing AMD and/or a symptom or complication thereof also include subjects with at least 1 or 2 grandparents, parents, or siblings who suffer from AMD, and/or the symptom or complication thereof. In various embodiments, a subject who carries a mutation in a CFH, ARMS2, HTRA1 gene, or a gene involved in transporting or processing HDL.

Subjects at risk of developing retinopathy include subjects with diabetes, arterial hypertension, sickle cell disease, a retinal vascular disease such as retinal vein or artery occlusion, Alström syndrome, or Bardet-Biedl syndrome. Subjects at risk of developing retinopathy also include premature human newborns (infants about 0, 1, 2, 3, 4, 5, 6, 7, 8, 9, 10 or more weeks old who were born after less than about 9, 8, or 7, months of pregnancy), subjects who have been exposed to ionizing radiation, and subjects whose retinas have been exposed to direct sunlight. In some embodiments, the retinopathy is diabetic retinopathy. Subjects at risk of developing diabetic retinopathy include, e.g., subjects with type 1 or type 2 diabetes. In various embodiments, the retinopathy is proliferative (e.g., proliferative diabetic retinopathy).

Subjects at risk of developing heart failure include subjects with high blood pressure, coronary artery disease, diabetes, sleep apnea, a congenital heart defect, valvular heart disease, or irregular heartbeats. Subjects at risk of heart failure also include alcoholics and former alcoholics, subjects who have used tobacco (e.g., who have smoked cigarettes for at least about 5, 10, 15, or 20 years), subjects who are obese, and subjects who have had a heart attack. Subjects who have taken rosiglitazone, pioglitazone, and nonsteroidal anti-inflammatory drugs (NSAIDs) [e.g., regularly (such as 1, 2, 3, 4, 5, 6, or 7 times per week) for at least about 1, 2, 3, 4, or 5 years] are also at risk for heart failure.

Subjects at risk of developing nephropathy (especially diabetic nephropathy) include subjects who have hyperglycemia, hypertension, at least 1 grandparent, parent, aunt, uncle, cousin, or sibling with nephropathy or hypertension. Additional non-limiting examples include subjects who smoke or have smoked for at least about 1, 5, 10, or more years.

Such subjects may be treated using the methods, agonists, and compositions disclosed herein.

Exemplary Agonists

Non-limiting examples of NOTCH3 agonists include any molecule, e.g., an antibody, that can produce an activated signaling form of the receptor, including soluble ligands of the receptor, antibodies and fragments thereof, small molecules that bind NOTCH3 extracellularly or that can enter the cell and act intracellularly, molecules that have enzymatic activity in cleaving the receptor to release the activated form, and molecules with the ability to destabilize the negative regulatory region of the receptor. In various embodiments, an agonist of NOTCH3, in addition to binding a NOTCH3 receptor, has a direct effect on a cell that comprises the NOTCH3 receptor. In embodiments, the NOTCH3 agonist will bind NOTCH3 receptor, and as well, initiate or mediate the signaling event associated with the NOTCH3 receptor, such as, for example, to cause the intracellular domain of NOTCH3 to be released for nuclear translocation.

In some embodiments (e.g., relating to CADASIL), a mechanism for reduced NOTCH3 function (e.g. inhibition) includes aberrant protein-protein interaction mediated by cysteine residues. In certain embodiments, a NOTCH3 agonist may operate by inhibiting the formation of these aberrant disulfide bridges, e.g., using small molecules or peptides or nucleic acids that neutralize disulfide bridges. See, e.g., Hague et al. (2014) "Inhibition of tau aggregation by a rosamine derivative that blocks tau intermolecular disulfide cross-linking" Amyloid 21(3):185-90, the entire content of which is incorporated herein by reference.

Small Molecules

In some embodiments, the NOTCH3 agonist is a small molecule.

In some embodiments, the small molecule comprises an Amaryllidaceae alkaloid. Non-limiting examples or small molecules include N-methylhemeanthidine chloride (NMHC), and pharmaceutically acceptable salts thereof. NMHC is an Amaryllidaceae alkaloid that may be isolated from *Zephyranthes candida*. See, e.g., Ye et al. (2016) Sci. Rep. 6, 26510; and Luo et al. (2012) J Nat Prod. 75, 2113-20, the entire contents of each of which are hereby incorporated herein by reference. The structure of NMHC is:

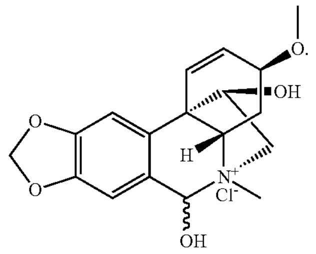 [SMILES: CO[C@@H]1C=C[C@@]23c4cc5c(cc4C(O)[N@@+](C)(C[C@@H]2O)[C@H]3C1)OCO5 ; [Cl-]]

In certain embodiments, the small molecule comprises a rosamine derivative bearing mild thiol reactivity. See, e.g., Hague et al. (2014) "Inhibition of tau aggregation by a rosamine derivative that blocks tau intermolecular disulfide cross-linking" Amyloid 21(3):185-90, the entire contents of which are incorporated herein by reference. In embodiments, the small molecule has the following structure:

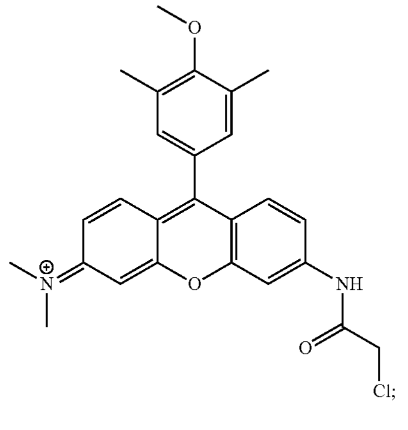

-continued

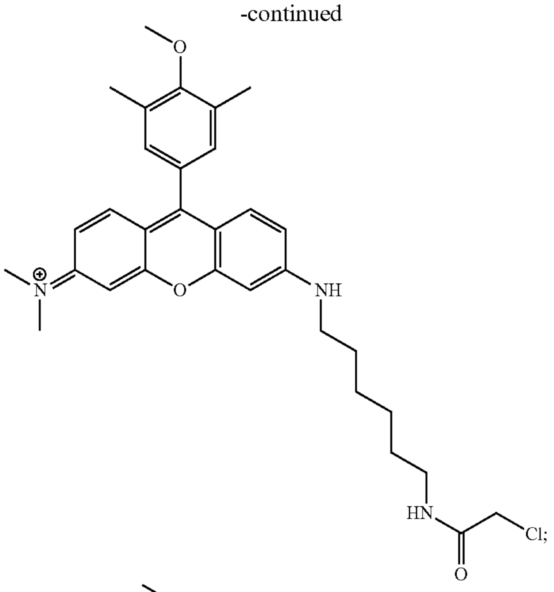

or

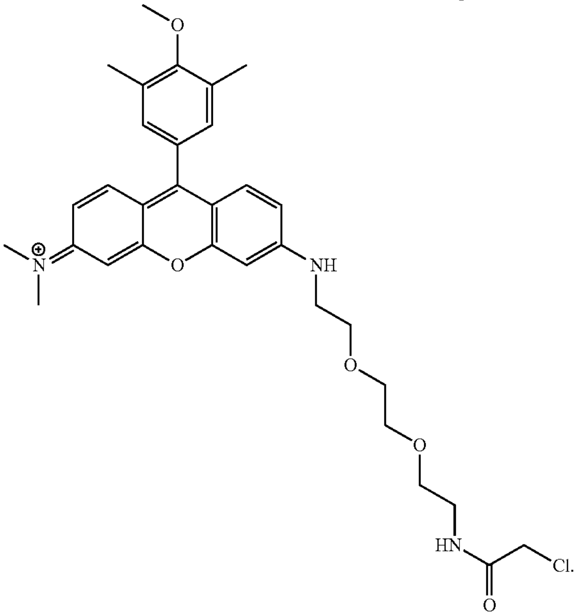 [SMILES: COc1c(C)cc(-c2c3ccc(=[N+](C)C)cc-3oc3cc(NCCOCCOCCNC(=O)CCl)ccc23)cc1C]

Antibodies

In some embodiments, the NOTCH3 agonist is an antibody or a fragment thereof.

As used herein, the term "antibody" refers to immunoglobulin molecules and immunologically active portions of immunoglobulin (Ig) molecules, i.e., molecules that contain an antigen binding site that specifically binds (immunoreacts with) an antigen. Such antibodies include, but are not limited to, polyclonal, monoclonal, chimeric, single chain, $F_{ab}$, $F_{ab'}$ and $F_{(ab')2}$ fragments, an $F_{ab}$ expression library, single-chain antibody molecules (e.g., scFv), and multispecific antibodies formed from antibody fragments. By "specifically bind" or "immunoreacts with" is meant that the antibody reacts with one or more antigenic determinants of the desired antigen and does not react (i.e., bind) with other polypeptides or binds at much lower affinity ($K_d > 10^{-6}$) with other polypeptides.

An "antibody fragment" refers to a molecule other than an intact antibody that comprises a portion of an intact antibody that binds the antigen to which the intact antibody binds. The terms "full length antibody," "intact antibody," and "whole antibody" are used herein interchangeably to refer to an antibody having a structure substantially similar to a native antibody structure or having heavy chains that contain an Fc region.

The basic antibody structural unit is known to comprise a tetramer. Each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. Human light chains are classified as kappa and lambda light chains. Heavy chains are classified as mu, delta, gamma, alpha, or epsilon, and define the antibody's isotype as IgM, IgD, IgA, and IgE, respectively. Within light and heavy chains, the variable and constant regions are joined by a "J" region of about 12 or more amino acids, with the heavy chain also including a "D" region of about 10 more amino acids. See generally, Fundamental Immunology Ch. 7 (Paul, W., ea., 2nd ed. Raven Press, N.Y. (1989)). The variable regions of each light/heavy chain pair form the antibody binding site.

In general, antibody molecules obtained from humans relate to any of the classes IgG, IgM, IgA, IgE and IgD, which differ from one another by the nature of the heavy chain present in the molecule. Certain classes have sub-classes as well, such as $IgG_1$, $IgG_2$, and others. Furthermore, in humans, the light chain may be a kappa chain or a lambda chain.

The term "antigen-binding site" or "binding portion" refers to the part of the immunoglobulin molecule that participates in antigen binding. The antigen binding site is formed by amino acid residues of the N-terminal variable ("V") regions of the heavy ("H") and light ("L") chains. Three highly divergent stretches within the V regions of the heavy and light chains, referred to as "hypervariable regions," are interposed between more conserved flanking stretches known as "framework regions," or "FRs." Thus, the term "FR" refers to amino acid sequences which are naturally found between, and adjacent to, hypervariable regions in immunoglobulins. In an antibody molecule, the three hypervariable regions of a light chain and the three hypervariable regions of a heavy chain are disposed relative to each other in three dimensional space to form an antigen-binding surface. The antigen-binding surface is complementary to the three-dimensional surface of a bound antigen, and the three hypervariable regions of each of the heavy and light chains are referred to as "complementarity-determining regions," or "CDRs." The assignment of amino acids to each domain is in accordance with the definitions of Kabat Sequences of Proteins of Immunological Interest (National Institutes of Health, Bethesda, Md. (1987 and 1991)), or Chothia & Lesk J. Mol. Biol. 196:901-917 (1987), Chothia et al. Nature 342:878-883 (1989).

An "Fv" fragment is an antibody fragment which contains a complete antigen recognition and binding site. This region consists of a dimer of one heavy and one light chain variable domain in tight association, which can be covalent in nature, for example in scFv. It is in this configuration that the three hypervariable regions (HVRs) of each variable domain interact to define an antigen binding site on the surface of the VH-VL dimer. Collectively, the six HVRs or a subset thereof confer antigen binding specificity to the antibody. However, even a single variable domain (or half of an Fv comprising only three HVRs specific for an antigen) has the ability to recognize and bind antigen, although usually at a lower affinity than the entire binding site.

A "Fab" fragment contains a variable and constant domain of the light chain and a variable domain and the first constant domain (CHI) of the heavy chain. F(ab') 2 antibody fragments comprise a pair of Fab fragments which are generally covalently linked near their carboxy termini by hinge cysteines between them. Other chemical couplings of antibody fragments are also known in the art, "Single-chain Fv" or "scFv" antibody fragments comprise the VH and VL domains of an antibody, wherein these domains are present in a single polypeptide chain. Generally the Fv polypeptide further comprises a polypeptide linker between the VH and L domains, which enables the scFv to form the desired structure for antigen binding. For a review of scFv, see Pluckthun in The Pharmacology of Monoclonal Antibodies, Vol 113, Rosenburg and Moore eds. Springer-Verlag, New York, pp. 269-31S (1994).

The term "diabodies" refers to small antibody fragments with two antigen-binding sites, which fragments comprise a heavy chain variable domain (VH) connected to a light chain variable domain (VL) in the same polypeptide chain (VH and VL). By using a linker that is too short to allow pairing between the two domains on the same chain, the domains are forced to pair with the complementary domains of another chain and create two antigen-binding sites. Diabodies are described more fully in, for example, BP 404,097; WO 93/11161; and Hollinger et al., Proc. Natl. Acad. Sci. USA, 90:6444-6448 (1993).

The expression "linear antibodies" refers to antibodies as described in Zapata et al., Protein Eng., 8 (10): 1057-1062 (1995). Briefly, these antibodies comprise a pair of tandem segments which, together with complementary light chain polypeptides, form a pair of antigen binding regions. Linear antibodies can be bispecific or monospecific.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

As used herein, the term "epitope" includes any protein determinant capable of specific binding to an antibody, an antibody fragment, or a T-cell receptor. Epitopic determinants usually consist of chemically active surface groupings of molecules such as amino acids or sugar side chains and usually have specific three dimensional structural characteristics, as well as specific charge characteristics. An antibody is said to specifically bind an antigen when the dissociation constant is ≤1 μM; preferably ≤100 nM and most preferably ≤10 nM.

Antibodies can be produced according to various methods known in the art.

Methods of preparing monoclonal antibodies are known in the art. For example, monoclonal antibodies may be prepared using hybridoma methods, such as those described by Kohler and Milstein (1975) Nature 256:495. In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro. The immunizing agent will typically include a full length protein or a fragment thereof. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (see pp. 59-103 in Goding (1986) Monoclonal Antibodies: Principles and Practice Academic Press). Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

In some examples, the antibodies to an epitope for an interested protein as described herein or a fragment thereof are humanized antibodies. Humanized forms of non-human (e.g., murine) antibodies are chimeric molecules of immunoglobulins, immunoglobulin chains or fragments thereof (such as Fv, $F_{ab}$, $F_{ab'}$, $F_{(ab')2}$ or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, a humanized antibody will comprise substantially all of at least one, and typically two, variable domains, in which all or substantially all of the CDR regions correspond to those of a non-human immunoglobulin and all or substantially all of the framework (FR) regions are those of a human immunoglobulin consensus sequence. The humanized antibody optimally also will comprise at least a portion of an immunoglobulin constant region (Fc), typically that of a human immunoglobulin (Jones et al. 1986. Nature 321:522-525; Riechmann et al. 1988. Nature 332:323-329; Presta. 1992. Curr. Op. Struct. Biol. 2:593-596). Humanization can be essentially performed following methods of Winter and co-workers (see, e.g., Jones et al. 1986. Nature 321:522-525; Riechmann et al. 1988. Nature 332:323-327; and Verhoeyen et al. 1988. Science 239:1534-1536), by substituting rodent CDRs or CDR sequences for the corresponding sequences of a human antibody. Accordingly, such humanized antibodies are chimeric antibodies (e.g., U.S. Pat. No. 4,816,567), wherein substantially less than an intact human variable domain has been substituted by the corresponding sequence from a non-human species.

In various examples the antibodies to an epitope of an interested protein as described herein or a fragment thereof are human antibodies. Human antibodies can also be produced using various techniques known in the art, including phage display libraries (Hoogenboom and Winter. 1991. J. Mol. Biol. 227:381-388; Marks et al. 1991. J. Mol. Biol. 222:581-597) or the preparation of human monoclonal antibodies [e.g., Cole et al. 1985. Monoclonal Antibodies and Cancer Therapy Liss; Boerner et al. 1991. J. Immunol. 147(1):86-95]. Similarly, human antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in most respects, including gene rearrangement, assembly, and antibody repertoire. This approach is described, e.g., in U.S. Pat. Nos. 5,545,807; 5,545,806; 5,569,825; 5,625,126; 5,633,425; 5,661,016, and in the following scientific publications: Marks et al. 1992. Bio/Technology 10:779-783; Lonberg et al. 1994. Nature 368:856-859; Morrison. 1994. Nature 368:812-13; Fishwild et al. 1996. Nature Biotechnology 14:845-51; Neuberger. 1996. Nature Biotechnology 14:826; Lonberg and Huszar. 1995. Intern. Rev. Immunol. 13:65-93. U.S. Pat. No. 6,719,971 also provides guidance to methods of generating humanized antibodies.

Aptamers

Aptamers are small, single stranded biomolecules, typically oligonucleotides (either DNA or RNA) or peptides, that bind to a specific target molecule (e.g. a protein or small molecule such as a steroid). They can be considered analogous to antibodies in their specificity but, unlike antibodies, aptamers are have a relatively low molecular weight. Peptide-based aptamers are generally less than thirty residues long while nucleotide-based aptamers are typically less than one hundred residues long.

Non-limiting examples of methods that are useful for designing aptamers that bind to a particular protein, such as NOTCH3, are described in U.S. Pat. Nos. 8,484,010; 5,582,981; PCT International Patent Application No. WO 2015/049356; Blackwell et al., (1993) Science 250:1104-1110; Blackwell, et al., (1990) Science 250:1149-1152; Tuerk and Gold (1990) Science 249:505-510; and Joyce (1989) Gene 82:83-87, the entire contents of each of which are incorporated herein by reference.

Peptides

Additional non-limiting examples of NOTCH3 agonists include NOTCH3 ligands and fragments (e.g., soluble fragments) thereof.

In some embodiments, the NOTCH3 agonist is a fragment of JAGGED1, JAGGED2, DELTA-LIKE1, DELTA-LIKE3, or DELTA-LIKE4.

In certain embodiments, the agonist comprises a fragment of JAGGED1 having the amino acid sequence CDDYYYGFGCNKFCRPR (SEQ ID NO:1) or CDDYYYGFGCNKFCRPRDDFFGH (SEQ ID NO:2). See, e.g., Li et al. (1998) Immunity 1998, 8, 43-55; Nickoloff et al. (2002) Cell Death Different. 9, 842; and Yamamura et al., (2014) Am J Physiol Cell Physiol. 306(9): C871-8, the entire contents of each of which are incorporated herein by reference. A polypeptide comprising the sequence CDDYYYGFGCNKFCRPR (SEQ ID NO:1) is commercially available from AnaSpec Inc. (Fremont, CA, USA). Additional non-limiting examples of NOTCH3 agonists include larger fragments of JAGGED1 that comprise CDDYYYGFGCNKFCRPR (SEQ ID NO:1), with the proviso that such fragments do not comprise the transmembrane domain (positions 1068-1093) or cytoplasmic domain (positions 1094-1218) of JAGGED1. Thus, in some embodiments, the NOTCH3 agonist comprises the extracellular domain of JAGGED1 (positions 34-1067; SEQ ID NO: 15) or a fragment thereof that comprises the amino acid sequence CDDYYYGFGCNKFCRPR (SEQ ID NO:1). In certain embodiments, the fragment of the JAGGED1 extracellular domain is a fragment that comprises the amino acid sequence of

```
                                  (SEQ ID NO: 2)
CDDYYYGFGCNKFCRPRDDFFGH.
```

The amino acid sequence for full-length human JAGGED1 is publically available in the UniProt database under accession number P78504 (SEQ ID NO: 14) and is as follows (an exemplary functional fragment that agonizes NOTCH3 is bolded and underlined):

MRSPRTRGRSGRPLSLLLALLCALRAKVCGASGQFELEILSMQNVNGELQNGNCCGGA

RNPGDRKCTRDECDTYFKVCLKEYQSRVTAGGPCSFGSGSTPVIGGNTFNLKASRGNDR

NRIVLPFSFAWPRSYTLLVEAWDSSNDTVQPDSIIEKASHSGMINPSRQWQTLKQNTGV

AHFEYOIRVTCDDYYYGFGCNKFCRPRDDFFGHYACDONGNKTCMEGWMGPECNRA

ICRQGCSPKHGSCKLPGDCRCQYGWQGLYCDKCIPHPGCVHGICNEPWQCLCETNWGG

QLCDKDLNYCGTHQPCLNGGTCSNTGPDKYQCSCPEGYSGPNCEIAEHACLSDPCHNR

GSCKETSLGFECECSPGWTGPTCSTNIDDCSPNNCSHGGTCQDLVNGFKCVCPPQWTGK

TCQLDANECEAKPCVNAKSCKNLIASYYCDCLPGWMGQNCDININDCLGQCQNDASCR

DLVNGYRCICPPGYAGDHCERDIDECASNPCLNGGHCQNEINRFQCLCPTGFSGNLCQL

DIDYCEPNPCQNGAQCYNRASDYFCKCPEDYEGKNCSHLKDHCRTTPCEVIDSCTVAM

ASNDTPEGVRYISSNVCGPHGKCKSQSGGKFTCDCNKGFTGTYCHENINDCESNPCRNG

GTCIDGVNSYKCICSDGWEGAYCETNINDCSQNPCHNGGTCRDLVNDFYCDCKNGWK

GKTCHSRDSQCDEATCNNGGTCYDEGDAFKCMCPGGWEGTTCNIARNSSCLPNPCHNG

GTCVVNGESFTCVCKEGWEGPICAQNTNDCSPHPCYNSGTCVDGDNWYRCECAPGFA

GPDCRININECQSSPCAFGATCVDEINGYRCVCPPGHSGAKCQEVSGRPCITMGSVIPDG

AKWDDDCNTCQCLNGRIACSKVWCGPRPCLLHKGHSECPSGQSCIPILDDQCFVHPCTG

VGECRSSSLQPVKTKCTSDSYYQDNCANITFTFNKEMMSPGLTTEHICSELRNLNILKNV

SAEYSIYIACEPSPSANNEIHVAISAEDIRDDGNPIKEITDKIIDLVSKRDGNSSLIAAVAEV

RVQRRPLKNRTDFLVPLLSSVLTVAWICCLVTAFYWCLRKRRKPGSHTHSASEDNTTNN

VREQLNQIKNPIEKHGANTVPIKDYENKNSKMSKIRTHNSEVEEDDMDKHQQKARFAK

QPAYTLVDREEKPPNGTPTKHPNWTNKQDNRDLESAQSLNRMEYIV

The amino acid sequence for the extracellular domain of human JAGGED1 is as follows (SEQ ID NO: 15):

QFELEILSMQNVNGELQNGNCCGGARNPGDRKCTRDECDTYFKVCLKEYQSRVTAGGP

CSFGSGSTPVIGGNTFNLKASRGNDRNRIVLPFSFAWPRSYTLLVEAWDSSNDTVQPDSII

EKASHSGMINPSRQWQTLKQNTGVAHFEYQIRVTCDDYYYGFGCNKFCRPRDDFFGHY

ACDQNGNKTCMEGWMGPECNRAICRQGCSPKHGSCKLPGDCRCQYGWQGLYCDKCIP

HPGCVHGICNEPWQCLCETNWGGQLCDKDLNYCGTHQPCLNGGTCSNTGPDKYQCSC

PEGYSGPNCEIAEHACLSDPCHNRGSCKETSLGFECECSPGWTGPTCSTNIDDCSPNNCS

HGGTCQDLVNGFKCVCPPQWTGKTCQLDANECEAKPCVNAKSCKNLIASYYCDCLPG

WMGQNCDININDCLGQCQNDASCRDLVNGYRCICPPGYAGDHCERDIDECASNPCLNG

GHCQNEINRFQCLCPTGFSGNLCQLDIDYCEPNPCQNGAQCYNRASDYFCKCPEDYEGK

-continued

NCSHLKDHCRTTPCEVIDSCTVAMASNDTPEGVRYISSNVCGPHGKCKSQSGGKFTCDC

NKGFTGTYCHENINDCESNPCRNGGTCIDGVNSYKCICSDGWEGAYCETNINDCSQNPC

HNGGTCRDLVNDFYCDCKNGWKGKTCHSRDSQCDEATCNNGGTCYDEGDAFKCMCP

GGWEGTTCNIARNSSCLPNPCHNGGTCVVNGESFTCVCKEGWEGPICAQNTNDCSPHPC

YNSGTCVDGDNWYRCECAPGFAGPDCRININECQSSPCAFGATCVDEINGYRCVCPPGH

SGAKCQEVSGRPCITMGSVIPDGAKWDDDCNTCQCLNGRIACSKVWCGPRPCLLHKGH

SECPSGQSCIPILDDQCFVHPCTGVGECRSSSLQPVKTKCTSDSYYQDNCANITFTFNKE

MMSPGLTTEHICSELRNLNILKNVSAEYSIYIACEPSPSANNEIHVAISAEDIRDDGNPIKEI

TDKIIDLVSKRDGNSSLIAAVAEVRVQRRPLKNRTD

In some embodiments, the agonist comprises a fragment of JAGGED2 comprising the amino acid sequence CDENYYSATCNKFCRPR (SEQ ID NO:3) or CDENYYSATCNKFCRPRNDFFGH (SEQ ID NO:4). Additional non-limiting examples of NOTCH3 agonists include larger fragments of JAGGED2 that comprise CDENYYSATCNKFCRPR (SEQ ID NO:3), with the proviso that such fragments do not comprise the transmembrane domain (positions 1081-1101) or cytoplasmic domain (positions 1102-1238) of JAGGED2. Thus, in some embodiments, the NOTCH3 agonist comprises the extracellular domain of JAGGED2 (positions 27-1080; SEQ ID NO: 17) or a fragment thereof that comprises the amino acid sequence CDENYYSATCNKFCRPR (SEQ ID NO:3). In certain embodiments, the fragment of the JAGGED2 extracellular domain is a fragment that comprises the amino acid sequence of CDENYYSATCNKFCRPRNDFFGH (SEQ ID NO:4).

The amino acid sequence for full-length human JAGGED2 is publically available in the UniProt database under accession number Q9Y219 (SEQ ID NO: 16) and is as follows (an exemplary functional fragment that agonizes NOTCH3 is bolded and underlined):

MRAQGRGRLPRRLLLLLALWVQAARPMGYFELQLSALRNVNGELLSGACCDGDGRTT

RAGGCGHDECDTYVRVCLKEYQAKVTPTGPCSYGHGATPVLGGNSFYLPPAGAAGDR

ARARARAGGDQDPGLVVIPFQFAWPRSFTLIVEAWDWDNDTTPNEELLIERVSHAGMIN

PEDRWKSLHFSGHVAHLELOIRVRCDENYYSATCNKFCRPRNDFFGHYTCDOYGNKA

CMDGWMGKECKEAVCKQGCNLLHGGCTVPGECRCSYGWQGRFCDECVPYPGCVHGS

CVEPWQCNCETNWGGLLCDKDLNYCGSHHPCTNGGTCINAEPDQYRCTCPDGYSGRN

CEKAEHACTSNPCANGGSCHEVPSGFECHCPSGWSGPTCALDIDECASNPCAAGGTCVD

QVDGFECICPEQWVGATCQLDANECEGKPCLNAFSCKNLIGGYYCDCIPGWKGINCHIN

VNDCRGQCQHGGTCKDLVNGYQCVCPRGFGGRHCELERDECASSPCHSGGLCEDLAD

GFHCHCPQGFSGPLCEVDVDLCEPSPCRNGARCYNLEGDYYCACPDDFGGKNCSVPRE

PCPGGACRVIDGCGSDAGPGMPGTAASGVCGPHGRCVSQPGGNFSCICDSGFTGTYCHE

NIDDCLGQPCRNGGTCIDEVDAFRCFCPSGWEGELCDTNPNDCLPDPCHSRGRCYDLVN

DFYCACDDGWKGKTCHSREFQCDAYTCSNGGTCYDSGDTFRCACPPGWKGSTCAVAK

NSSCLPNPCVNGGTCVGSGASFSCICRDGWEGRTCTHNTNDCNPLPCYNGGICVDGVN

WFRCECAPGFAGPDCRINIDECQSSPCAYGATCVDEINGYRCSCPPGRAGPRCQEVIGFG

RSCWSRGTPFPHGSSWVEDCNSCRCLDGRRDCSKVWCGWKPCLLAGQPEALSAQCPL

GQRCLEKAPGQCLRPPCEAWGECGAEEPPSTPCLPRSGHLDNNCARLTLHFNRDHVPQG

TTVGAICSGIRSLPATRAVARDRLLVLLCDRASSGASAVEVAVSFSPARDLPDSSLIQGA

AHAIVAAITQRGNSSLLLAVTEVKVETVVTGGSSTGLLVPVLCGAFSVLWLACVVLCV

WWTRKRRKERERSRLPREESANNQWAPLNPIRNPIERPGGHKDVLYQCKNFTPPPRRAD

EALPGPAGHAAVREDEEDEDLGRGEEDSLEAEKFLSHKFTKDPGRSPGRPAHWASGPK

VDNRAVRSINEARYAGKE

The amino acid sequence for the extracellular domain of human JAGGED2 is as follows (SEQ ID NO: 17):

MGYFELQLSALRNVNGELLSGACCDGDGRTTRAGGCGHDECDTYVRVCLKEYQAKVT

PTGPCSYGHGATPVLGGNSFYLPPAGAAGDRARARARAGGDQDPGLVVIPFQFAWPRS

FTLIVEAWDWDNDTTPNEELLIERVSHAGMINPEDRWKSLHFSGHVAHLELQIRVRCDE

NYYSATCNKFCRPRNDFFGHYTCDQYGNKACMDGWMGKECKEAVCKQGCNLLHGGC

TVPGECRCSYGWQGRFCDECVPYPGCVHGSCVEPWQCNCETNWGGLLCDKDLNYCGS

HHPCTNGGTCINAEPDQYRCTCPDGYSGRNCEKAEHACTSNPCANGGSCHEVPSGFECH

CPSGWSGPTCALDIDECASNPCAAGGTCVDQVDGFECICPEQWVGATCQLDANECEGK

PCLNAFSCKNLIGGYYCDCIPGWKGINCHINVNDCRGQCQHGGTCKDLVNGYQCVCPR

GFGGRHCELERDECASSPCHSGGLCEDLADGFHCHCPQGFSGPLCEVDVDLCEPSPCRN

GARCYNLEGDYYCACPDDFGGKNCSVPREPCPGGACRVIDGCGSDAGPGMPGTAASG

VCGPHGRCVSQPGGNFSCICDSGFTGTYCHENIDDCLGQPCRNGGTCIDEVDAFRCFCPS

GWEGELCDTNPNDCLPDPCHSRGRCYDLVNDFYCACDDGWKGKTCHSREFQCDAYTC

SNGGTCYDSGDTFRCACPPGWKGSTCAVAKNSSCLPNPCVNGGTCVGSGASFSCICRDG

WEGRTCTHNTNDCNPLPCYNGGICVDGVNWFRCECAPGFAGPDCRINIDECQSSPCAYG

ATCVDEINGYRCSCPPGRAGPRCQEVIGFGRSCWSRGTPFPHGSSWVEDCNSCRCLDGR

RDCSKVWCGWKPCLLAGQPEALSAQCPLGQRCLEKAPGQCLRPPCEAWGECGAEEPPS

TPCLPRSGHLDNNCARLTLHFNRDHVPQGTTVGAICSGIRSLPATRAVARDRLLVLLCD

RASSGASAVEVAVSFSPARDLPDSSLIQGAAHAIVAAITQRGNSSELLAVTEVKVETVVT

GGSST

In some embodiments, the agonist comprises a fragment of DELTA-LIKE1 comprising the amino acid sequence CDEHYYGEGCSVFCRPR (SEQ ID NO:5) or CDEHYYGEGCSVFCRPRDDAFGH (SEQ ID NO:6). Additional non-limiting examples of NOTCH3 agonists include larger fragments of DELTA-LIKE1 that comprise CDEHYYGEGCSVFCRPR (SEQ ID NO:5), with the proviso that such fragments do not comprise the transmembrane domain (positions 546-568) or cytoplasmic domain (positions 569-723) of DELTA-LIKE1. Thus, in some embodiments, the NOTCH3 agonist comprises the extracellular domain of DELTA-LIKE1 (positions 18-545; SEQ ID NO: 19) or a fragment thereof that comprises the amino acid sequence CDEHYYGEGCSVFCRPR (SEQ ID NO:5). In certain embodiments, the fragment of the DELTA-LIKE1 extracellular domain is a fragment that comprises the amino acid sequence of CDEHYYGEGCSVFCRPRDDAFGH (SEQ ID NO:6).

The amino acid sequence for full-length human DELTA-LIKE1 is publically available in the UniProt database under accession number 000548 (SEQ ID NO: 18) and is as follows (an exemplary functional fragment that agonizes NOTCH3 is bolded and underlined):

MGSRCALALAVLSALLCQVWSSGVFELKLQEFVNKKGLLGNRNCCRGGAGPPPCACRT

FFRVCLKHYQASVSPEPPCTYGSAVTPVLGVDSFSLPDGGGADSAFSNPIRFPFGFTWPG

TFSLIIEALHTDSPDDLATENPERLISRLATQRHLTVGEEWSQDLHSSGRTDLKYSYRFVC

DEHYYGEGCSVFCRPRDDAFGHFTCGERGEKVCNPGWKGPYCTEPICLPGCDEOHGF

CDKPGECKCRVGWQGRYCDECIRYPGCLHGTCQQPWQCNCQEGWGGLFCNQDLNYC

THHKPCKNGATCTNTGQGSYTCSCRPGYTGATCELGIDECDPSPCKNGGSCTDLENSYS

CTCPPGFYGKICELSAMTCADGPCFNGGRCSDSPDGGYSCRCPVGYSGFNCEKKIDYCS

SSPCSNGAKCVDLGDAYLCRCQAGFSGRHCDDNVDDCASSPCANGGTCRDGVNDFSCT

CPPGYTGRNCSAPVSRCEHAPCHNGATCHERGHRYVCECARGYGGPNCQFLLPELPPGP

AVVDLTEKLEGQGGPFPWVAVCAGVILVLMLLLGCAAVVVCVRLRLQKHRPPADPCR

GETETMNNLANCQREKDISVSIIGATQIKNTNKKADFHGDHSADKNGFKARYPAVDYN

-continued

LVQDLKGDDTAVRDAHSKRDTKCQPQGSSGEEKGTPTTLRGGEASERKRPDSGCSTSK

DTKYQSVYVISEEKDECVIATEV

The amino acid sequence for the extracellular domain of human DELTA-LIKE1 is as follows (SEQ ID NO: 19):

QVWSSGVFELKLQEFVNKKGLLGNRNCCRGGAGPPPCACRTFFRVCLKHYQASVSPEP

PCTYGSAVTPVLGVDSFSLPDGGGADSAFSNPIRFPFGFTWPGTFSLIIEALHTDSPDDLA

TENPERLISRLATQRHLTVGEEWSQDLHSSGRTDLKYSYRFVCDEHYYGEGCSVFCRPR

DDAFGHFTCGERGEKVCNPGWKGPYCTEPICLPGCDEQHGFCDKPGECKCRVGWQGR

YCDECIRYPGCLHGTCQQPWQCNCQEGWGGLFCNQDLNYCTHHKPCKNGATCTNTGQ

GSYTCSCRPGYTGATCELGIDECDPSPCKNGGSCTDLENSYSCTCPPGFYGKICELSAMT

CADGPCFNGGRCSDSPDGGYSCRCPVGYSGFNCEKKIDYCSSSPCSNGAKCVDLGDAYL

CRCQAGFSGRHCDDNVDDCASSPCANGGTCRDGVNDFSCTCPPGYTGRNCSAPVSRCE

HAPCHNGATCHERGHRYVCECARGYGGPNCQFLLPELPPGPAVVDLTEKLEGQGGPFP

W

In some embodiments, the agonist comprises a fragment of DELTA-LIKE3 comprising the amino acid sequence CEPPAVGTACTRLCRPR (SEQ ID NO:7). Additional non-limiting examples of NOTCH3 agonists include larger fragments of DELTA-LIKE3 that comprise CEPPAVGTACTRLCRPR (SEQ ID NO:7), with the proviso that such fragments do not comprise the transmembrane domain (positions 493-513) or cytoplasmic domain (positions 514-618) of DELTA-LIKE3. Thus, in some embodiments, the NOTCH3 agonist comprises the extracellular domain of DELTA-LIKE3 (positions 27-492; SEQ ID NO: 21) or a fragment thereof that comprises the amino acid sequence CEPPAVGTACTRLCRPR (SEQ ID NO:7).

The amino acid sequence for full-length human DELTA-LIKE3 is publically available in the UniProt database under accession number Q9NYJ7 (SEQ ID NO: 20) and is as follows (an exemplary functional fragment that agonizes NOTCH3 is bolded and underlined):

MVSPRMSGLLSQTVILALIFLPQTRPAGVFELQIHSFGPGPGPGAPRSPCSARLPCRLFFRV

CLKPGLSEEAAESPCALGAALSARGPVYTEQPGAPAPDLPLPDGLLQVPFRDAWPGTFSF

IIETWREELGDQIGGPAWSLLARVAGRRRLAAGGPWARDIQRAGAWELRFSYRARCEP

PAVGTACTRLCRPRSAPSRCGPGLRPCAPLEDECEAPLVCRAGCSPEHGFCEOPGECRC

LEGWTGPLCTVPVSTSSCLSPRGPSSATTGCLVPGPGPCDGNPCANGGSCSETPRSFECT

CPRGFYGLRCEVSGVTCADGPCFNGGLCVGGADPDSAYICHCPPGFQGSNCEKRVDRCS

LQPCRNGGLCLDLGHALRCRCRAGFAGPRCEHDLDDCAGRACANGGTCVEGGGAHRC

SCALGFGGRDCRERADPCAARPCAHGGRCYAHFSGLVCACAPGYMGARCEFPVHPDG

ASALPAAPPGLRPGDPQRYLLPPALGLLVAAGVAGAALLLVHVRRRGHSQDAGSRLLA

GTPEPSVHALPDALNNLRTQEGSGDGPSSSVDWNRPEDVDPQGIYVISAPSIYAREVATP

LFPPLHTGRAGQRQHLLFPYPSSILSVK

The amino acid sequence for the extracellular domain of human DELTA-LIKE3 is as follows (SEQ ID NO: 21):

AGVFELQIHSFGPGPGPGAPRSPCSARLPCRLFFRVCLKPGLSEEAAESPCALGAALSARG

PVYTEQPGAPAPDLPLPDGLLQVPFRDAWPGTFSFIIETWREELGDQIGGPAWSLLARVA

GRRRLAAGGPWARDIQRAGAWELRFSYRARCEPPAVGTACTRLCRPRSAPSRCGPGLR

PCAPLEDECEAPLVCRAGCSPEHGFCEQPGECRCLEGWTGPLCTVPVSTSSCLSPRGPSS

ATTGCLVPGPGPCDGNPCANGGSCSETPRSFECTCPRGFYGLRCEVSGVTCADGPCFNG

GLCVGGADPDSAYICHCPPGFQGSNCEKRVDRCSLQPCRNGGLCLDLGHALRCRCRAG

FAGPRCEHDLDDCAGRACANGGTCVEGGGAHRCSCALGFGGRDCRERADPCAARPCA

HGGRCYAHFSGLVCACAPGYMGARCEFPVHPDGASALPAAPPGLRPGDPQRYL

In some embodiments, the agonist comprises a fragment of DELTA-LIKE4 comprising the amino acid sequence CSDNYYGDNCSRLCKKR (SEQ ID NO:8) or CSDNYYGDNCSRLCKKRNDHFGH (SEQ ID NO:9). Additional non-limiting examples of NOTCH3 agonists include larger fragments of DELTA-LIKE4 that comprise CSDNYYGDNCSRLCKKR (SEQ ID NO:8), with the proviso that such fragments do not comprise the transmembrane domain (positions 530-550) or cytoplasmic domain (positions 551-685) of DELTA-LIKE4. Thus, in some embodiments, the NOTCH3 agonist comprises the extracellular domain of DELTA-LIKE4 (positions 27-529; SEQ ID NO: 23) or a fragment thereof that comprises the amino acid sequence CSDNYYGDNCSRLCKKR (SEQ ID NO:8). In certain embodiments, the fragment of the DELTA-LIKE4 extracellular domain is a fragment that comprises the amino acid sequence of CSDNYYGDNCSRLCKKRNDHFGH (SEQ ID NO:9).

The amino acid sequence for full-length human DELTA-LIKE4 is publically available in the UniProt database under accession number Q9NR61 (SEQ ID NO: 22) and is as follows (an exemplary functional fragment that agonizes NOTCH3 is bolded and underlined):

MAAASRSASGWALLLLVALWQQRAAGSGVFQLQLQEFINERGVLASGRPCEPGCRTFF

RVCLKHFQAVVSPGPCTFGTVSTPVLGTNSFAVRDDSSGGGRNPLQLPFNFTWPGTFSLI

IEAWHAPGDDLRPEALPPDALISKIAIQGSLAVGQNWLLDEQTSTLTRLRYSYRVICSDN

YYGDNCSRLCKKRNDHFGHYVCQPDGNLSCLPGWTGEYCQQPICLSGCHEONGYCSK

PAECLCRPGWQGRLCNECIPHNGCRHGTCSTPWQCTCDEGWGGLFCDQDLNYCTHHSP

CKNGATCSNSGQRSYTCTCRPGYTGVDCELELSECDSNPCRNGGSCKDQEDGYHCLCP

PGYYGLHCEHSTLSCADSPCFNGGSCRERNQGANYACECPPNFTGSNCEKKVDRCTSNP

CANGGQCLNRGPSRMCRCRPGFTGTYCELHVSDCARNPCAHGGTCHDLENGLMCTCP

AGFSGRRCEVRTSIDACASSPCFNRATCYTDLSTDTFVCNCPYGFVGSRCEFPVGLPPSFP

WVAVSLGVGLAVLLVLLGMVAVAVRQLRLRRPDDGSREAMNNLSDFQKDNLIPAAQL

KNTNQKKELEVDCGLDKSNCGKQQNHTLDYNLAPGPLGRGTMPGKFPHSDKSLGEKA

PLRLHSEKPECRISAICSPRDSMYQSVCLISEERNECVIATEV

The amino acid sequence for the extracellular domain of human DELTA-LIKE4 is as follows (SEQ ID NO: 23):

SGVFQLQLQEFINERGVLASGRPCEPGCRTFFRVCLKHFQAVVSPGPCTFGTVSTPVLGT

NSFAVRDDSSGGGRNPLQLPFNFTWPGTFSLIIEAWHAPGDDLRPEALPPDALISKIAIQG

SLAVGQNWLLDEQTSTLTRLRYSYRVICSDNYYGDNCSRLCKKRNDHFGHYVCQPDGN

LSCLPGWTGEYCQQPICLSGCHEQNGYCSKPAECLCRPGWQGRLCNECIPHNGCRHGTC

STPWQCTCDEGWGGLFCDQDLNYCTHHSPCKNGATCSNSGQRSYTCTCRPGYTGVDC

ELELSECDSNPCRNGGSCKDQEDGYHCLCPPGYYGLHCEHSTLSCADSPCFNGGSCRER

NQGANYACECPPNFTGSNCEKKVDRCTSNPCANGGQCLNRGPSRMCRCRPGFTGTYCE

LHVSDCARNPCAHGGTCHDLENGLMCTCPAGFSGRRCEVRTSIDACASSPCFNRATCYT

DLSTDTFVCNCPYGFVGSRCEFPVGLPPSFPW

Pharmaceutical Formulations and Delivery

Dosages, formulations, dosage volumes, regimens, and methods for administering a NOTCH3 agonist may vary. Thus, minimum and maximum effective dosages vary depending on the method of administration.

"Administering" an agonist described herein can be effected or performed using any of the various methods and delivery systems known to those skilled in the art. The administering can be, for example, intravenous, oral, ocular (e.g., subconjunctival, intravitreal, retrobulbar, or intracameral), intramuscular, intravascular, intra-arterial, intracoronary, intramyocardial, intraperitoneal, subcutaneous, inhaled, or intrathecal. Other non-limiting examples include topical administration, or coating of a device to be placed within the subject. In embodiments, administration is effected by injection or via a catheter.

As used herein, "effective" when referring to an amount of a therapeutic compound refers to the quantity of the compound that is sufficient to yield a desired therapeutic response without undue adverse side effects (such as toxicity, irritation, or allergic response) commensurate with a reasonable benefit/risk ratio when used in the manner of this disclosure.

As used herein, "pharmaceutically acceptable" carrier or excipient refers to a carrier or excipient that is suitable for use with humans and/or animals without undue adverse side effects (such as toxicity, irritation, and allergic response) commensurate with a reasonable benefit/risk ratio. It can be, e.g., a pharmaceutically acceptable solvent, suspending agent or vehicle, for delivering the instant compounds to the subject.

As used herein, a "monotherapy" is therapy that is administered to inhibit, treat, or prevent a disorder, such as a SVD, without any other therapy that is used to treat the disorder. A monotherapy for treating a disorder may optionally be combined with another treatment that is used to ameliorate a symptom of the disorder while not being directed against the disorder, for example an analgesic compound, an anti-pyretic compound, and/or an anti-inflammatory compound (e.g., aspirin, ibuprofen, naproxen, or acetaminophen) may be administered concurrently with the monotherapy.

In various embodiments, a composition comprising a NOTCH3 agonist may be administered only once or multiple times. For example, a NOTCH3 agonist may be administered using a method disclosed herein at least about once, twice, three times, four times, five times, six times, or seven times per day, week, month, or year. In some embodiments, a composition comprising a NOTCH3 agonist is administered once per month. In certain embodiments, the composition is administered once per month via intravitreal injection. In various embodiments, such as embodiments involving eye drops, a composition is self-administered.

For the treatment of an ocular disorder, a NOTCH3 agonist (e.g., a pharmaceutical composition comprising a NOTCH3 agonist) may be administered locally, e.g., as a topical eye drop, peri-ocular injection (e.g., sub-tenon), intraocular injection, intravitreal injection, retrobulbar injection, intraretinal injection, subretinal injection, subconjunctival injection, or using iontophoresis, or peri-ocular devices which can actively or passively deliver drug.

Sustained release of drug may be achieved by the use of technologies such as implants (e.g., solid implants) (which may or may not be bio-degradable) or bio-degradable polymeric matrices (e.g., micro-particles). These may be administered, e.g., peri-ocularly or intravitreally.

Pharmaceutical formulations adapted for topical administration may be formulated as aqueous solutions, ointments, creams, suspensions, lotions, powders, solutions, pastes, gels, sprays, aerosols, liposomes, microcapsules, microspheres, or oils.

For treatments of the eye or other external tissues, such as the mouth or skin, the formulations (e.g., a pharmaceutical composition comprising a NOTCH3 agonist) may be applied as a topical ointment or cream. When formulated in an ointment, a NOTCH3 agonist may be employed with either a paraffinic or a water-miscible ointment base. Alternatively, a NOTCH3 agonist may be formulated in a cream with an oil-in-water cream base or a water-in-oil base.

The present subject matter provides compositions comprising a NOTCH3 agonist and a carrier or excipient suitable for administration to ocular tissue. Such carriers and excipients are suitable for administration to ocular tissue (e.g., sclera, lens, iris, cornea, uvea, retina, macula, or vitreous tissue) without undue adverse side effects (such as toxicity, irritation, and allergic response) commensurate with a reasonable benefit/risk ratio.

Pharmaceutical formulations adapted for topical administrations to the eye include eye drops wherein a NOTCH3 agonist is dissolved or suspended in a suitable carrier, especially an aqueous solvent. Formulations to be administered to the eye will have ophthalmically compatible pH and osmolality. The term "ophthalmically acceptable vehicle" means a pharmaceutical composition having physical properties (e.g., pH and/or osmolality) that are physiologically compatible with ophthalmic tissues.

In some embodiments, an ophthalmic composition of the present invention is formulated as sterile aqueous solutions having an osmolality of from about 200 to about 400 milliosmoles/kilogram water ("mOsm/kg") and a physiologically compatible pH. The osmolality of the solutions may be adjusted by means of conventional agents, such as inorganic salts (e.g., NaCl), organic salts (e.g., sodium citrate), polyhydric alcohols (e.g., propylene glycol or sorbitol) or combinations thereof.

In various embodiments, the ophthalmic formulations may be in the form of liquid, solid or semisolid dosage form. The ophthalmic formulations may comprise, depending on the final dosage form, suitable ophthalmically acceptable excipients. In some embodiments, the ophthalmic formulations are formulated to maintain a physiologically tolerable pH range. In certain embodiments, the pH range of the ophthalmic formulation is in the range of from about 5 to about 9. In some embodiments, pH range of the ophthalmic formulation is in the range of from about 6 to about 8, or is about 6.5, about 7, or about 7.5.

In some embodiments, the composition is in the form of an aqueous solution, such as one that can be presented in the form of eye drops. By means of a suitable dispenser, a desired dosage of the active agent can be metered by administration of a known number of drops into the eye, such as by one, two, three, four, or five drops.

One or more ophthalmically acceptable pH adjusting agents and/or buffering agents can be included in a composition, including acids such as acetic, boric, citric, lactic, phosphoric, and hydrochloric acids; bases such as sodium hydroxide, sodium phosphate, sodium borate, sodium citrate, sodium acetate, and sodium lactate; and buffers such as citrate/dextrose, sodium bicarbonate, and ammonium chloride. Such acids, bases, and buffers can be included in an amount required to maintain pH of the composition in an ophthalmically acceptable range. One or more ophthalmically acceptable salts can be included in the composition in an amount sufficient to bring osmolality of the composition into an ophthalmically acceptable range. Such salts include those having sodium, potassium, or ammonium cations and chloride, citrate, ascorbate, borate, phosphate, bicarbonate, sulfate, thiosulfate, or bisulfite anions.

The ocular delivery device may be designed for the controlled release of one or more therapeutic agents with multiple defined release rates and sustained dose kinetics and permeability. Controlled release may be obtained through the design of polymeric matrices incorporating different choices and properties of biodegradable/bioerodable polymers (e.g., poly(ethylene vinyl)acetate (EVA), superhydrolyzed PVA), hydroxyalkyl cellulose (HPC), methylcellulose (MC), hydroxypropyl methyl cellulose (HPMC), polycaprolactone, poly(glycolic) acid, poly(lactic) acid, polyanhydride, of polymer molecular weights, polymer crystallinity, copolymer ratios, processing conditions, surface finish, geometry, excipient addition, and polymeric coatings that will enhance drug diffusion, erosion, dissolution, and osmosis.

Formulations for drug delivery using ocular devices may combine one or more active agents and adjuvants appropriate for the indicated route of administration. For example, a NOTCH3 agonist (optionally with another agent) may be admixed with any pharmaceutically acceptable excipient, lactose, sucrose, starch powder, cellulose esters of alkanoic acids, stearic acid, talc, magnesium stearate, magnesium oxide, sodium and calcium salts of phosphoric and sulphuric acids, acacia, gelatin, sodium alginate, polyvinylpyrrolidine, and/or polyvinyl alcohol, tableted or encapsulated for conventional administration. Alternatively, the compounds may be dissolved in polyethylene glycol, propylene glycol, carboxymethyl cellulose colloidal solutions, ethanol, corn oil, peanut oil, cottonseed oil, sesame oil, tragacanth gum, and/or various buffers. The compounds may also be mixed with compositions of both biodegradable and non-biodegradable polymers, and a carrier or diluent that has a time delay property. Representative examples of biodegradable compositions can include albumin, gelatin, starch, cellulose, dextrans, polysaccharides, poly(D,L-lactide), poly(D,L-lactide-co-glycolide), poly(glycolide), poly(hydroxybutyrate), poly(alkylcarbonate) and poly(orthoesters), and mixtures thereof. Representative examples of non-biodegradable polymers can include EVA copolymers, silicone rubber and poly(methylacrylate), and mixtures thereof.

Pharmaceutical compositions for ocular delivery also include in situ gellable aqueous composition. Such a composition comprises a gelling agent in a concentration effective to promote gelling upon contact with the eye or with lacrimal fluid. Suitable gelling agents include but are not limited to thermosetting polymers. The term “in situ gellable” as used herein includes not only liquids of low viscosity that form gels upon contact with the eye or with lacrimal fluid, but also includes more viscous liquids such as semi-fluid and thixotropic gels that exhibit substantially increased viscosity or gel stiffness upon administration to the eye. See, for example, Ludwig, Adv. Drug Deliv. Rev. 3; 57:1595-639 (2005), the entire content of which is incorporated herein by reference.

Biocompatible implants for placement in the eye have been disclosed in a number of patents, such as U.S. Pat. Nos. 4,521,210; 4,853,224; 4,997,652; 5,164,188; 5,443,505; 5,501,856; 5,766,242; 5,824,072; 5,869,079; 6,074,661; 6,331,313; 6,369,116; 6,699,493; and 8,293,210, the entire contents of each of which are incorporated herein by reference.

The implants may be monolithic, i.e. having the active agent (e.g., a NOTCH3 agonist) or agents homogenously distributed through the polymeric matrix, or encapsulated, where a reservoir of active agent is encapsulated by the polymeric matrix. Due to ease of manufacture, monolithic implants are usually preferred over encapsulated forms. However, the greater control afforded by the encapsulated, reservoir-type implant may be of benefit in some circumstances, where the therapeutic level of the drug falls within a narrow window. In addition, the therapeutic component, including a NOTCH3 agonist, may be distributed in a non-homogenous pattern in the matrix. For example, the implant may include a portion that has a greater concentration of a NOTCH3 agonist relative to a second portion of the implant.

The intraocular implants disclosed herein may have a size of between about 5 um and about 2 mm, or between about 10 um and about 1 mm for administration with a needle, greater than 1 mm, or greater than 2 mm, such as 3 mm or up to 10 mm, for administration by surgical implantation. The vitreous chamber in humans is able to accommodate relatively large implants of varying geometries, having lengths of, for example, 1 to 10 mm. The implant may be a cylindrical pellet (e.g., rod) with dimensions of about 2 mm×0.75 mm diameter. The implant may be a cylindrical pellet with a length of about 7 mm to about 10 mm, and a diameter of about 0.75 mm to about 1.5 mm.

The implants may also be at least somewhat flexible so as to facilitate both insertion of the implant in the eye, such as in the vitreous, and accommodation of the implant. The total weight of the implant is usually about 250-5000 μg, more preferably about 500-1000 μg. For example, an implant may be about 500 μg, or about 1000 μg. For non-human subject, the dimensions and total weight of the implant(s) may be larger or smaller, depending on the type of subject. For example, humans have a vitreous volume of approximately 3.8 ml, compared with approximately 30 ml for horses, and approximately 60-100 ml for elephants. An implant sized for use in a human may be scaled up or down accordingly for other animals, for example, about 8 times larger for an implant for a horse, or about, for example, 26 times larger for an implant for an elephant.

Implants can be prepared where the center may be of one material and the surface may have one or more layers of the same or a different composition, where the layers may be cross-linked, or of a different molecular weight, different density or porosity, or the like. For example, where it is desirable to quickly release an initial bolus of drug, the center may be a polylactate coated with a polylactate-polyglycolate copolymer, so as to enhance the rate of initial degradation. Alternatively, the center may be polyvinyl alcohol coated with polylactate, so that upon degradation of the polylactate exterior the center would dissolve and be rapidly washed out of the eye.

The implants may be of any geometry including fibers, sheets, films, microspheres, spheres, circular discs, plaques, and the like. The upper limit for the implant size will be determined by factors such as toleration for the implant, size limitations on insertion, ease of handling, etc. Where sheets or films are employed, the sheets or films will be in the range of at least about 0.5 mm×0.5 mm, usually about 3-10 mm×5-10 mm with a thickness of about 0.1-1.0 mm for ease of handling. Where fibers are employed, the fiber diameter will generally be in the range of about 0.05 to 3 mm and the fiber length will generally be in the range of about 0.5-10 mm. Spheres may be in the range of 0.5 μm to 4 mm in diameter, with comparable volumes for other shaped particles.

The size and form of the implant can also be used to control the rate of release, period of treatment, and drug concentration at the site of implantation. Larger implants will deliver a proportionately larger dose, but depending on the surface to mass ratio, may have a slower release rate. The particular size and geometry of the implant are chosen to suit the site of implantation.

Microspheres for ocular delivery are described, for example, in U.S. Pat. Nos. 5,837,226; 5,731,005; 5,641,750; 7,354,574; and U.S. Pub. No. 2008-0131484, the entire contents of each of which are incorporated herein by reference.

For oral or enteral formulations for use with the present invention, tablets can be formulated in accordance with conventional procedures employing solid carriers well-known in the art. Capsules employed for oral formulations to be used with the methods of the present invention can be made from any pharmaceutically acceptable material, such as gelatin or cellulose derivatives. Sustained release oral delivery systems and/or enteric coatings for orally administered dosage forms are also contemplated, such as those described in U.S. Pat. Nos. 4,704,295; 4, 556,552; 4,309, 404; and 4,309,406, the entire contents of each of which are incorporated herein by reference.

General Definitions

Unless specifically defined otherwise, all technical and scientific terms used herein shall be taken to have the same meaning as commonly understood by one of ordinary skill in the art (e.g., in cell culture, molecular genetics, and biochemistry).

As used herein, the term "about" in the context of a numerical value or range means±10% of the numerical value or range recited or claimed, unless the context requires a more limited range.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." In addition, use of the term "based on," above and in the claims is intended to mean, "based at least in part on," such that an unrecited feature or element is also permissible.

It is understood that where a parameter range is provided, all integers within that range, and tenths thereof, are also provided by the invention. For example, "0.2-5 mg" is a disclosure of 0.2 mg, 0.3 mg, 0.4 mg, 0.5 mg, 0.6 mg etc. up to and including 5.0 mg.

A small molecule is a compound that is less than 2000 daltons in mass. The molecular mass of the small molecule is preferably less than 1000 daltons, more preferably less than 600 daltons, e.g., the compound is less than 500 daltons, 400 daltons, 300 daltons, 200 daltons, or 100 daltons.

As used herein, an "isolated" or "purified" nucleic acid molecule, polynucleotide, polypeptide, or protein, is substantially free of other cellular material, or culture medium when produced by recombinant techniques, or chemical precursors or other chemicals when chemically synthesized. Purified compounds are at least 60% by weight (dry weight) the compound of interest. Preferably, the preparation is at least 75%, more preferably at least 90%, and most preferably at least 99%, by weight the compound of interest. For example, a purified compound is one that is at least 90%, 91%, 92%, 93%, 94%, 95%, 98%, 99%, or 100% (w/w) of the desired compound by weight. Purity is measured by any appropriate standard method, for example, by column chromatography, thin layer chromatography, or high-performance liquid chromatography (HPLC) analysis. A purified or isolated polynucleotide (RNA or DNA) is free of the genes or sequences that flank it in its naturally-occurring state. Purified also defines a degree of sterility that is safe for administration to a human subject, e.g., lacking infectious or toxic agents.

Similarly, by "substantially pure" is meant a nucleotide or polypeptide that has been separated from the components that naturally accompany it. Typically, the nucleotides and polypeptides are substantially pure when they are at least 60%, 70%, 80%, 90%, 95%, or even 99%, by weight, free from the proteins and naturally-occurring organic molecules with they are naturally associated.

The term "sample" as used herein refers to a biological sample obtained for the purpose of evaluation in vitro. In embodiments, the sample may comprise a body fluid. In some embodiments, the body fluid includes, but is not limited to, whole blood, plasma, serum, lymph, breast milk, saliva, mucous, semen, cellular extracts, inflammatory fluids, cerebrospinal fluid, vitreous humor, tears, vitreous, aqueous humor, or urine obtained from the subject. In some aspects, the sample is a composite panel of two or more body fluids. In exemplary aspects, the sample comprises blood or a fraction thereof (e.g., plasma, serum, or a fraction obtained via leukapheresis). In embodiments, the sample is a tissue sample, such as a biopsy.

A "control" sample or value refers to a sample that serves as a reference, usually a known reference, for comparison to a test sample. For example, a test sample can be taken from a test subject, e.g., a subject with a small vessel disease or in need of diagnosis for a small vessel disease, and compared to samples from known conditions, e.g., a subject (or subjects) that does not have the small vessel disease (a negative or normal control), or a subject (or subjects) who does have the small vessel disease (positive control). A control can also represent an average value gathered from a number of tests or results. One of skill in the art will recognize that controls can be designed for assessment of any number of parameters. One of skill in the art will understand which controls are valuable in a given situation and be able to analyze data based on comparisons to control values. Controls are also valuable for determining the significance of data. For example, if values for a given parameter are variable in controls, variation in test samples will not be considered as significant.

The term, "normal amount" with respect to a compound (e.g., a protein or mRNA) refers to a normal amount of the compound in an individual who does not have a SVD or in a healthy or general population. The amount of a compound can be measured in a test sample and compared to the "normal control" level, utilizing techniques such as reference limits, discrimination limits, or risk defining thresholds to define cutoff points and abnormal values (e.g., for a particular SVD or a symptom thereof). The normal control level means the level of one or more compounds or combined compounds typically found in a subject known not suffering from an SVD. Such normal control levels and cutoff points may vary based on whether a compounds is used alone or in a formula combining with other compounds into an index. Alternatively, the normal control level can be a database of compounds patterns from previously tested subjects who did not develop a SVD or a particular symptom thereof (e.g., in the event the SVD develops or a subject already having the SVD is tested) over a clinically relevant time horizon.

The level that is determined may be the same as a control level or a cut off level or a threshold level, or may be increased or decreased relative to a control level or a cut off level or a threshold level. In some aspects, the control subject is a matched control of the same species, gender, ethnicity, age group, smoking status, body mass index (BMI), current therapeutic regimen status, medical history, or a combination thereof, but differs from the subject being diagnosed in that the control does not suffer from the disease (or a symptom thereof) in question or is not at risk for the disease.

Relative to a control level, the level that is determined may an increased level. As used herein, the term "increased" with respect to level (e.g., protein or mRNA level) refers to any % increase above a control level. In various embodiments, the increased level may be at least or about a 5% increase, at least or about a 10% increase, at least or about a 15% increase, at least or about a 20% increase, at least or about a 25% increase, at least or about a 30% increase, at least or about a 35% increase, at least or about a 40% increase, at least or about a 45% increase, at least or about a 50% increase, at least or about a 55% increase, at least or about a 60% increase, at least or about a 65% increase, at least or about a 70% increase, at least or about a 75% increase, at least or about a 80% increase, at least or about a 85% increase, at least or about a 90% increase, at least or about a 95% increase, relative to a control level.

Relative to a control level, the level that is determined may a decreased level. As used herein, the term "decreased" with respect to level (e.g., protein or mRNA level) refers to any % decrease below a control level. In various embodiments, the decreased level may be at least or about a 5% decrease, at least or about a 10% decrease, at least or about a 15% decrease, at least or about a 20% decrease, at least or about a 25% decrease, at least or about a 30% decrease, at least or about a 35% decrease, at least or about a 40% decrease, at least or about a 45% decrease, at least or about a 50% decrease, at least or about a 55% decrease, at least or about a 60% decrease, at least or about a 65% decrease, at least or about a 70% decrease, at least or about a 75% decrease, at least or about a 80% decrease, at least or about a 85% decrease, at least or about a 90% decrease, at least or about a 95% decrease, relative to a control level.

The transitional term "comprising," which is synonymous with "including," "containing," or "characterized by," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

The terms "subject," "patient," "individual," and the like as used herein are not intended to be limiting and can be generally interchanged. An individual described as a "subject," "patient," "individual," and the like does not necessarily have a given disease, but may be merely seeking medical advice. The terms "subject," "patient," "individual," and the like as used herein include all members of the animal kingdom that may suffer from the indicated disorder. In some aspects, the subject is a mammal, and in some aspects, the subject is a human.

As used herein, the singular forms "a," "an," and "the" include the plural reference unless the context clearly dictates otherwise. Thus, for example, a reference to "a disease," "a disease state", or "a nucleic acid" is a reference to one or more such embodiments, and includes equivalents thereof known to those skilled in the art and so forth.

As used herein, "treating" encompasses, e.g., inhibition, regression, or stasis of the progression of a disorder. For purposes of this disclosure, beneficial or desired clinical results include, but are not limited to, alleviation or amelioration of any symptom or symptoms, diminishment of extent of disease, stabilized (i.e., not worsening) state of disease, preventing spread of disease, delay or slowing of disease progression, amelioration or palliation of the disease state, and recovery (whether partial or total), whether detectable or undetectable. As used herein, "inhibition" of disease progression or a disease complication in a subject means preventing or reducing the disease progression and/or disease complication in the subject.

As used herein, a "symptom" associated with a disorder includes any clinical or laboratory manifestation associated with the disorder, and is not limited to what the subject can feel or observe.

Embodiments and examples are provided below to facilitate a more complete understanding of the invention. The following embodiments and examples illustrate the exemplary modes of making and practicing the invention. However, the scope of the invention is not limited to specific embodiments disclosed in these embodiments and examples, which are for purposes of illustration only, since alternative methods can be utilized to obtain similar results.

EMBODIMENTS

Embodiments include Embodiments P1 to P48 following.

Embodiment P1. A method for treating or preventing a small vessel disease (SVD) in a subject, comprising administering to the subject an effective amount of a Neurogenic Locus NOTCH Homolog Protein 3 (NOTCH3) agonist.

Embodiment P2. The method of Embodiment P1, wherein the SVD comprises cerebral SVD.

Embodiment P3. The method of Embodiment P1, wherein the SVD comprises cerebral autosomal-dominant arteriopathy with subcortical infarcts and leukoencephalopathy (CADASIL).

Embodiment P4. The method of Embodiment P1, wherein the SVD comprises cerebral autosomal recessive arteriopathy with subcortical infarcts and leukoencephalopathy (CARASIL).

Embodiment P5. The method of Embodiment P1, wherein the SVD comprises a NOTCH3 loss-of-function associated SVD.

Embodiment P6. The method of Embodiment P1, wherein the SVD comprises diabetic retinopathy.

Embodiment P7. The method of Embodiment P1, wherein the SVD comprises age-related macular degeneration (AMD), nephropathy, microangiopathy, heart failure, Alagille syndrome, familial tetralogy of Fallot, patent ductus arteriosus, or a cerebral cavernous malformation.

Embodiment P8. The method of any one of Embodiments P1-P7, wherein the subject has at least 1, 2, 3, or 4 grandparents, parents, aunts, uncles, cousins, or siblings who comprise the SVD.

Embodiment P9. The method of any one of Embodiments P1-P8, wherein the subject comprises diabetes.

Embodiment P10. The method of Embodiment P9, wherein the diabetes is type 1 diabetes or type 2 diabetes.

Embodiment P11. The method of any one of Embodiments P1-P10, wherein the subject is at least about 80 years old.

Embodiment P12. The method of any one of Embodiments P1-P11, wherein a test sample obtained from the subject comprises a level of NOTCH3 protein or mRNA that is different than a normal control.

Embodiment P13. The method of Embodiment P12, wherein the test sample comprises a level of NOTCH3 protein or mRNA that is at least about 5%, 10%, 15%, 20%, 25%, 30%, 40%, 45%, 50%, 55%, 60%, 65%, 70%, 75%, 80%, 90%, 95%, 99%, 100%, 5-50%, 50-75%, or 75-100% lower in the test sample compared to a normal control.

Embodiment P14. The method of Embodiment P12, wherein the test sample comprises a level of NOTCH3 activity that is at least about 5%, 10%, 15%, 20%, 25%, 30%, 40%, 45%, 50%, 55%, 60%, 65%, 70%, 75%, 80%, 90%, 95%, 99%, 100%, 5-50%, 50-75%, or 75-100% lower in the test sample compared to a normal control.

Embodiment P15. The method of Embodiment P12, wherein the test sample comprises blood, serum, or plasma.

Embodiment P16. The method of Embodiment P12, wherein the test sample comprises saliva, tears, vitreous, cerebrospinal fluid, sweat, cerebrospinal fluid, or urine.

Embodiment P17. The method of any one of Embodiments P1-P16, wherein a test sample obtained from the subject comprises a level of collagen18$\alpha$1, endostatin, NOTCH3, N3ECD, insulin-like growth factor binding protein 1 (IGFBP-1), and/or High-Temperature Requirement A Serine Peptidase 1 (HTRA1) protein or mRNA that is different than a normal control.

Embodiment P18. The method of any one of Embodiments P12-P17, wherein the test sample comprises a level of collagen18$\alpha$1, endostatin, IGFBP-1, and/or HTRA1 protein or mRNA that is at least about 5%, 10%, 15%, 20%, 25%, 30%, 40%, 45%, 50%, 55%, 60%, 65%, 70%, 75%, 80%, 90%, 5-50%, 50-75%, 1-fold, 2-fold, 3-fold, 4-fold, or 5-fold higher in the test sample compared to a normal control.

Embodiment P19. The method of any one of Embodiments P12-P17, wherein the test sample comprises a level of HTRA1 protein or mRNA that is at least about 5%, 10%, 15%, 20%, 25%, 30%, 40%, 45%, 50%, 55%, 60%, 65%, 70%, 75%, 80%, 90%, 95%, 99%, 100%, 5-50%, 50-75%, or 75-100% lower in the test sample compared to a normal control.

Embodiment P20. The method of any one of Embodiments P1-P19, wherein the NOTCH3 agonist is administered as a monotherapy.

Embodiment P21. The method of Embodiment P3, wherein the subject is not administered a thrombolytic agent.

Embodiment P22. The method of any one of Embodiments P1-P21, wherein the NOTCH3 agonist comprises a polypeptide, an antibody or a fragment thereof, an aptamer, or a small molecule.

Embodiment P23. The method of any one of Embodiments P1-P22, wherein the NOTCH3 agonist comprises a polypeptide.

Embodiment P24. The method of any one of Embodiments P1-P3, wherein the polypeptide comprises a fragment of a NOTCH3 ligand.

Embodiment P25. The method of Embodiment P24, wherein the ligand comprises JAGGED1 or a fragment thereof, JAGGED2 or a fragment thereof, or DELTA-LIKE1 or a fragment thereof.

Embodiment P26. The method of Embodiment P25, wherein the polypeptide comprises a fragment of JAGGED1.

Embodiment P27. The method of Embodiment P26, wherein the fragment of JAGGED1 is the extracellular domain of JAGGED1 or a fragment thereof comprising a stretch of amino acids having the sequence CDDYYYGFGCNKFCRPR (SEQ ID NO:1).

Embodiment P28. The method of Embodiment P26, wherein the fragment of JAGGED1 comprises a stretch of amino acids having the sequence or CDDYYYGFGCNKFCRPRDDFFGH (SEQ ID NO:2).

Embodiment P29. The method of Embodiment P25, wherein the polypeptide comprises a fragment of JAGGED2.

Embodiment P30. The method of Embodiment P29, wherein the fragment of JAGGED2 is the extracellular domain of JAGGED2 or a fragment thereof comprising a stretch of amino acids having the sequence CDENYYSATCNKFCRPR (SEQ ID NO:3).

Embodiment P31. The method of Embodiment P29, wherein the fragment of JAGGED2 comprises a stretch of amino acids having the sequence CDENYYSATCNKFCRPRNDFFGH (SEQ ID NO:4).

Embodiment P32. The method of Embodiment P25, wherein the polypeptide comprises a fragment of DELTA-LIKE1.

Embodiment P33. The method of Embodiment P32, wherein the fragment of DELTA-LIKE1 is the extracellular domain of DELTA-LIKE1 or a fragment thereof comprising a stretch of amino acids having the sequence CDEHYYGEGCSVFCRPR (SEQ ID NO:5).

Embodiment P34. The method of Embodiment P32, wherein the fragment of DELTA-LIKE1 comprises a stretch of amino acids having the sequence CDEHYYGEGCSVFCRPRDDAFGH (SEQ ID NO:6).

Embodiment P35. The method of Embodiment P25, wherein the polypeptide comprises a fragment of DELTA-LIKE3.

Embodiment P36. The method of Embodiment P35, wherein the fragment of DELTA-LIKE3 is the extracellular domain of DELTA-LIKE1 or a fragment thereof comprising a stretch of amino acids having the sequence CEPPAVGTACTRLCRPR (SEQ ID NO:7).

Embodiment P37. The method of Embodiment P25, wherein the polypeptide comprises a fragment of DELTA-LIKE4.

Embodiment P38. The method of Embodiment P37, wherein the fragment of DELTA-LIKE4 is the extracellular domain of DELTA-LIKE1 or a fragment thereof comprising a stretch of amino acids having the sequence CSDNYYGDNCSRLCKKR (SEQ ID NO:8).

Embodiment P39. The method of Embodiment P37, wherein the fragment of DELTA-LIKE4 comprises a stretch of amino acids having the sequence CSDNYYGDNCSRLCKKRNDHFGH (SEQ ID NO:9).

Embodiment P40. The method of any one of Embodiments P1-P21, wherein the NOTCH3 agonist comprises an antibody or a fragment thereof.

Embodiment P41. The method of any one of Embodiments P1-P40, wherein the NOTCH3 agonist increases or decreases the expression or activity of a known modulator of NOTCH3 signaling.

Embodiment P42. A composition comprising an effective amount of a NOTCH3 agonist and an ophthalmically acceptable vehicle.

Embodiment P43. The composition of Embodiment P42, which is in the form of an aqueous solution comprising an osmolality of about 200 to about 400 milliosmoles/kilogram water.

Embodiment P44. The composition of Embodiment P42 or P43, wherein the NOTCH3 agonist comprises a polypeptide, an antibody or a fragment thereof, an aptamer, or a small molecule.

Embodiment P45. The composition of Embodiment P44, wherein the polypeptide comprises a fragment of a NOTCH3 ligand.

Embodiment P46. The composition of Embodiment P44, wherein the NOTCH3 agonist comprises an antibody or a fragment thereof.

Embodiment P47. A composition comprising a NOTCH3 agonist and a pharmaceutically acceptable carrier for treating or preventing a SVD in a subject.

Embodiment P48. Use of a NOTCH3 agonist in the manufacture of a medicament for treating or preventing a SVD in a subject.

Additional embodiments include Embodiments 1 to 60 following.

Embodiment 1. A method for treating or preventing a small vessel disease (SVD) in a subject, comprising administering to the subject an effective amount of a Neurogenic Locus Notch Homolog Protein 3 (NOTCH3) agonist.

Embodiment 2. The method of Embodiment 1, wherein the NOTCH3 agonist comprises an antibody that binds to the NOTCH3 ectodomain (N3ECD) and increases NOTCH3 activity, wherein said N3ECD comprises SEQ ID NO: 12.

Embodiment 3. The method of Embodiment 1, wherein the NOTCH3 agonist comprises a polypeptide, an antibody or a fragment thereof, an aptamer, or a small molecule.

Embodiment 4. The method of Embodiment 3, wherein the NOTCH3 agonist comprises a polypeptide.

Embodiment 5. The method of Embodiment 4, wherein the polypeptide comprises a fragment of a NOTCH3 ligand.

Embodiment 6. The method of Embodiment 5, wherein the ligand comprises JAGGED1 or a fragment thereof, JAGGED2 or a fragment thereof, or DELTA-LIKE1 or a fragment thereof.

Embodiment 7. The method of Embodiment 6, wherein the polypeptide comprises a fragment of JAGGED1.

Embodiment 8. The method of Embodiment 7, wherein the fragment of JAGGED1 is the extracellular domain of JAGGED1 or a fragment thereof comprising a stretch of amino acids having the sequence CDDYYYGFGCNKFCRPR (SEQ ID NO:1).

Embodiment 9. The method of Embodiment 7, wherein the fragment of JAGGED1 comprises a stretch of amino acids having the sequence or CDDYYYGFGCNKFCRPRDDFFGH (SEQ ID NO:2).

Embodiment 10. The method of Embodiment 6, wherein the polypeptide comprises a fragment of JAGGED2.

Embodiment 11. The method of Embodiment 10, wherein the fragment of JAGGED2 is the extracellular domain of JAGGED2 or a fragment thereof comprising a stretch of amino acids having the sequence CDENYYSATCNKFCRPR (SEQ ID NO:3).

Embodiment 12. The method of Embodiment 10, wherein the fragment of JAGGED2 comprises a stretch of amino acids having the sequence CDENYYSATCNKFCRPRNDFFGH (SEQ ID NO:4).

Embodiment 13. The method of Embodiment 6, wherein the polypeptide comprises a fragment of DELTA-LIKE1.

Embodiment 14. The method of Embodiment 13, wherein the fragment of DELTA-LIKE1 is the extracellular domain of DELTA-LIKE1 or a fragment thereof comprising a stretch of amino acids having the sequence CDEHYYGEGCSVFCRPR (SEQ ID NO:5).

Embodiment 15. The method of Embodiment 13, wherein the fragment of DELTA-LIKE1 comprises a stretch of amino acids having the sequence CDEHYYGEGCSVFCRPRDDAFGH (SEQ ID NO:6).

Embodiment 16. The method of Embodiment 6, wherein the polypeptide comprises a fragment of DELTA-LIKE3.

Embodiment 17. The method of Embodiment 16, wherein the fragment of DELTA-LIKE3 is the extracellular domain of DELTA-LIKE1 or a fragment thereof comprising a stretch of amino acids having the sequence CEPPAVGTACTRLCRPR (SEQ ID NO:7).

Embodiment 18. The method of Embodiment 6, wherein the polypeptide comprises a fragment of DELTA-LIKE4.

Embodiment 19. The method of Embodiment 18, wherein the fragment of DELTA-LIKE4 is the extracellular domain of DELTA-LIKE1 or a fragment thereof comprising a stretch of amino acids having the sequence CSDNYYGDNCSRLCKKR (SEQ ID NO:8).

Embodiment 20. The method of Embodiment 18, wherein the fragment of DELTA-LIKE4 comprises a stretch of amino acids having the sequence CSDNYYGDNCSRLCKKRNDHFGH (SEQ ID NO:9).

Embodiment 21. The method of Embodiment 3, wherein the NOTCH3 agonist comprises an antibody or a fragment thereof.

Embodiment 22. The method of any one of Embodiments 1-21, wherein the NOTCH3 agonist increases or decreases the expression or activity of a known modulator of NOTCH3 signaling.

Embodiment 23. The method of any one of Embodiments 1-22, wherein the SVD comprises cerebral SVD.

Embodiment 24. The method of any one of Embodiments 1-22, wherein the SVD comprises cerebral autosomal-dominant arteriopathy with subcortical infarcts and leukoencephalopathy (CADASIL).

Embodiment 25. The method of any one of Embodiments 1-22, wherein the SVD comprises cerebral autosomal recessive arteriopathy with subcortical infarcts and leukoencephalopathy (CARASIL).

Embodiment 26. The method of any one of Embodiments 1-22, wherein the SVD comprises a NOTCH3 loss-of-function associated SVD.

Embodiment 27. The method of any one of Embodiments 1-22, wherein the SVD comprises diabetic retinopathy.

Embodiment 28. The method of any one of Embodiments 1-22, wherein the SVD comprises age-related macular degeneration (AMD), nephropathy, microangiopathy, heart failure, Alagille syndrome, familial tetralogy of Fallot, patent ductus arteriosus, or a cerebral cavernous malformation.

Embodiment 29. The method of any one of Embodiments 1-28, wherein the subject has at least 1, 2, 3, or 4 grandparents, parents, aunts, uncles, cousins, or siblings who comprise the SVD.

Embodiment 30. The method of any one of Embodiments 1-29, wherein the subject comprises diabetes.

Embodiment 31. The method of Embodiment 30, wherein the diabetes is type 1 diabetes or type 2 diabetes.

Embodiment 32. The method of any one of Embodiments 1-31, wherein the subject is at least about 80 years old.

Embodiment 33. The method of any one of Embodiments 1-32, wherein the subject comprises a level of NOTCH3 protein or mRNA that is different than a normal control.

Embodiment 34. The method of Embodiment 33, wherein the subject comprises a level of NOTCH3 protein or mRNA that is at least about 5%, 10%, 15%, 20%, 25%, 30%, 40%, 45%, 50%, 55%, 60%, 65%, 70%, 75%, 80%, 90%, 95%, 99%, 100%, 5-50%, 50-75%, or 75-100% lower compared to a normal control.

Embodiment 35. The method of any one of Embodiments 1-34, wherein the subject comprises a level of collagen18α1pha1 or endostatin protein or mRNA that is at least about 5%, 10%, 15%, 20%, 25%, 30%, 40%, 45%, 50%, 55%, 60%, 65%, 70%, 75%, 80%, 90%, 95%, 99%, 100%, 5-50%, 50-75%, or 75-100% lower compared to a normal control.

Embodiment 36. The method of any one of Embodiments 1-35, wherein the subject comprises a level of NOTCH3 protein bound to collagen18α1 and/or endostatin and/or HTRA1 and/or IGFBP-1 that is at least about 5%, 10%, 15%, 20%, 25%, 30%, 40%, 45%, 50%, 55%, 60%, 65%, 70%, 75%, 80%, 90%, 5-50%, 50-75%, 1-fold, 2-fold, 3-fold, 4-fold, or 5-fold higher compared to a normal control.

Embodiment 37. The method of any one of Embodiments 1-36, wherein the subject comprises a white mater hyperintensity and/or a lacunar stroke as observed by magnetic resonance imaging.

Embodiment 38. The method of any one of Embodiments 1-37, wherein the subject comprises a level of neurofilament light chain (NF-L) protein or activity that is at least about 5%, 10%, 15%, 20%, 25%, 30%, 40%, 45%, 50%, 55%, 60%, 65%, 70%, 75%, 80%, 90%, 5-50%, 50-75%, 1-fold, 2-fold, 3-fold, 4-fold, or 5-fold higher compared to a normal control.

Embodiment 39. The method of any one of Embodiments 1-38, wherein the subject comprises a level of NOTCH3 activity that is at least about 5%, 10%, 15%, 20%, 25%, 30%, 40%, 45%, 50%, 55%, 60%, 65%, 70%, 75%, 80%, 90%, 95%, 99%, 100%, 5-50%, 50-75%, or 75-100% lower compared to a normal control.

Embodiment 40. The method of any one of Embodiments 33-39, wherein the level is in a test sample obtained from the subject.

Embodiment 41. The method of Embodiment 40, wherein the test sample comprises blood, serum, or plasma.

Embodiment 42. The method of Embodiment 40, wherein the test sample comprises saliva, tears, vitreous, cerebrospinal fluid, sweat, cerebrospinal fluid, or urine.

Embodiment 43. The method of any one of Embodiments 1-42, wherein the subject comprises a level of collagen18α1, endostatin, NOTCH3, N3ECD, IGFBP-1, HTRA1, and/or NF-L protein or mRNA that is different than a normal control.

Embodiment 44. The method of any one of Embodiments 1-43, wherein the subject comprises a level of collagen18α1, endostatin, IGFBP-1, HTRA1, and/or NF-L protein or mRNA that is at least about 5%, 10%, 15%, 20%, 25%, 30%, 40%, 45%, 50%, 55%, 60%, 65%, 70%, 75%, 80%, 90%, 5-50%, 50-75%, 1-fold, 2-fold, 3-fold, 4-fold, or 5-fold higher compared to a normal control.

Embodiment 45. The method of any one of Embodiments 1-44, wherein the subject comprises a level of HTRA1 protein or mRNA that is at least about 5%, 10%, 15%, 20%, 25%, 30%, 40%, 45%, 50%, 55%, 60%, 65%, 70%, 75%, 80%, 90%, 95%, 99%, 100%, 5-50%, 50-75%, or 75-100% lower compared to a normal control.

Embodiment 46. The method of any one of Embodiments 1-45, wherein the subject comprises a protein-protein complex comprising NOTCH3 bound to collagen18α1/endostatin, HTRA1, IGFBP-1, and/or NOTCH3.

Embodiment 47. The method of Embodiment 46, wherein NOTCH3 is the NOTCH3 extracellular domain (N3ECD).

Embodiment 48. The method of any one of Embodiments 1-47, wherein the subject comprises a N3ECD homodimer.

Embodiment 49. The method of any one of Embodiments 1-48, wherein the NOTCH3 agonist is administered as a monotherapy.

Embodiment 50. The method of Embodiment 24, wherein the subject is not administered a thrombolytic agent.

Embodiment 51. The method of any one of Embodiments 1-50, wherein the subject has had a lacunar stroke.

Embodiment 52. The method of any one of Embodiments 1-51, wherein the subject has had a hemorrhagic stroke.

Embodiment 53. A composition comprising an effective amount of a NOTCH3 agonist and an ophthalmically acceptable vehicle.

Embodiment 54. The composition of Embodiment 53, which is in the form of an aqueous solution comprising an osmolality of about 200 to about 400 milliosmoles/kilogram water.

Embodiment 55. The composition of Embodiment 53 or 54, wherein the NOTCH3 agonist comprises a polypeptide, an antibody or a fragment thereof, an aptamer, or a small molecule.

Embodiment 56. The composition of Embodiment 55, wherein the small molecule comprises the following structure

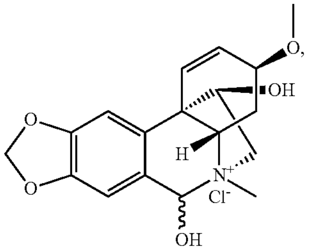

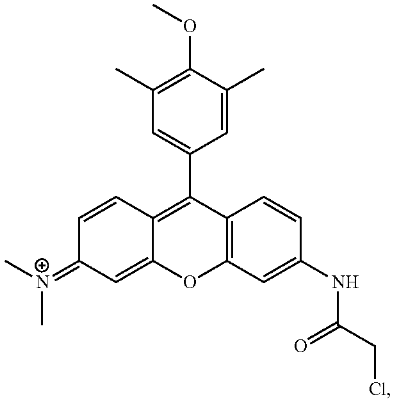

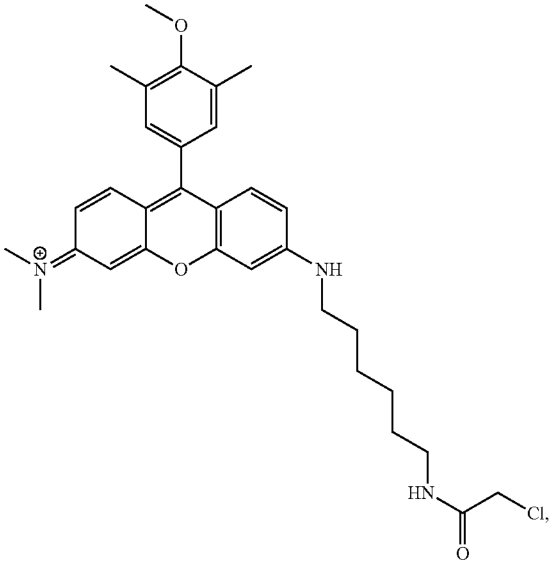

or

-continued

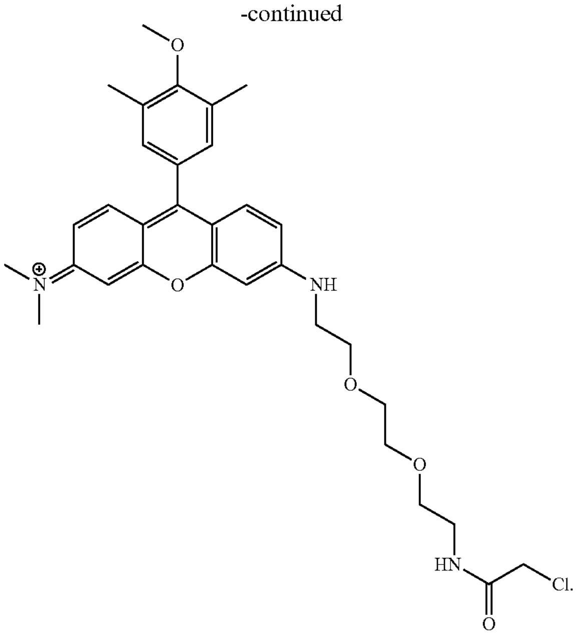

Embodiment 57. The composition of Embodiment 55, wherein the polypeptide comprises a fragment of a NOTCH3 ligand.

Embodiment 58. The composition of Embodiment 55, wherein the NOTCH3 agonist comprises an antibody or a fragment thereof.

Embodiment 59. A composition comprising a NOTCH3 agonist and a pharmaceutically acceptable carrier for treating or preventing a SVD in a subject.

Embodiment 60. Use of a NOTCH3 agonist in the manufacture of a medicament for treating or preventing a SVD in a subject.

Example 1: Therapeutic Targeting of NOTCH3 Signaling Prevents Mural Cell Loss in Small Vessel Disease The present disclosure is not limited by any particular scientific theory. However, discussions regarding the potential role of NOTCH3 in SVD are provided to facilitate the understanding of possible mechanisms involved with SVD in various embodiments described herein.

This Example discloses the characterization of a mouse model of SVD in which mural cell coverage in arteries depends upon human NOTCH3 function, a cell signaling mechanism associated with SVD and mural cell pathology in humans. The data presented herein shows that arteriolar degeneration linked to Notch mutations is suppressed by Notch signaling activation. Without being bound by any scientific theory, the data herein show Notch loss-of-function (and not Notch toxic gain-of-function or neomorphism) as the relevant mechanism in SVD.

A modality of treatment focused on preventing mural cell loss (a mechanistic cause of SVD) was tested. For that purpose mouse models of NOTCH3 were utilized. NOTCH3 is a gene strongly associated to SVD in humans (Arboleda-Velasquez et al., 2011, *Proc Natl Acad Sci USA* 108:E128-135; Arboleda-Velasquez et al., 2008, *Proc Natl Acad Sci USA* 105:4856-4861; Chabriat et al., 2009, Cadasil. *Lancet Neurol* 8:643-653; Henshall et al., 2015, *Arterioscler Thromb Vasc Biol* 35:409-420; Joutel et al., 1996, *Nature*

383:707-710). In mammalian cells, Notch receptors at the plasma membrane are heterodimers resulting from an S1 proteolytic cleavage mediated by Furin (Louvi and Artavanis-Tsakonas, 2012, *Semin Cell Dev Biol* 23:473-480). In the absence of the ligand, a Negative Regulatory Region (NRR) comprising the Lin12-Notch repeats (LNR) and the heterodimerization domain keep the receptor in an autoinhibited configuration stabilized via non-covalent bonds (Xu et al., 2015, *Structure* 23:1227-1235). Interactions with Notch ligands (DELTA-LIKE or JAGGED) expose an S2 cleavage site within the NRR to proteolysis by ADAM (A Disintegrin And Metalloproteinase Domain) (Louvi and Artavanis-Tsakonas, 2012, *Semin Cell Dev Biol* 23:473-480). Presenilin-containing gamma secretase constitutively cuts S-2 cleaved Notch receptors at a transmembrane site (S3) leading to nuclear translocation of the Notch intracellular domain and regulation of transcriptional downstream targets (Kopan, 2012, *Cold Spring Harb Perspect Biol* 4(10). pii: a011213).

Mutations in NOTCH3 leading to a NOTCH3 receptor with unpaired cysteines in the extracellular domain are a cause of CADASIL, the most common monogenic cause of cerebral SVD (Joutel et al., 1996, *Nature* 383:707-710). It has been proposed that CADASIL mutations trigger aggregation of the NOTCH3 extracellular domain and aberrant interactions between it and other proteins, leading to neomorphic effects (Arboleda-Velasquez et al., 2005, *Hum Mol Genet* 14:1631-1639; Chabriat et al., 2009, *Lancet Neurol* 8:643-653; Joutel et al., 2015, *J Cereb Blood Flow Metab* 36(1):143-57). CADASIL mutations located in the ligand-binding domain of the NOTCH3 receptor and those that impair plasma membrane localization overtly impair NOTCH3 downstream signaling (Arboleda-Velasquez et al., 2002, *Neurology* 59:277-279; Arboleda-Velasquez et al., 2011, *Proc Natl Acad Sci USA* 108:E128-135; Joutel et al., 2004, *Am J Hum Genet* 74:338-347). A distinct class of NOTCH3 mutations including premature stop codons or frame shift mutations in NOTCH3 are also associated with cerebral SVD; patients with these loss-of-function mutations in NOTCH3 develop symptoms later in life, show incomplete penetrance compared to CADASIL patients, and lack CADASIL's characteristic vascular deposits (e.g. NOTCH3 extracellular domain and granular osmiophilic material, GOM)(Dotti et al., 2004, *Arch Neurol* 61:942-945; Erro et al., 2015, *Folia Neuropathol* 53:168-171; Moccia et al., 2015, *Neurobiol Aging* 36:547 e545-511; Pippucci et al., 2015, *EMBO Mol Med* 7(6):848-58; Rutten et al., 2013, *Hum Mutat* 34:1486-1489; Yoon et al., 2015, *Neurobiol Aging* 36:2443 e2441-2447). Consistent with the pathobiology of these human conditions, CADASIL and NOTCH3 knockout mice develop progressive loss of mural cells (Arboleda-Velasquez et al., 2011, *Proc Natl Acad Sci USA* 108:E128-135; Ghosh et al., 2015, *Ann Neurol* 78(6):887-900; Henshall et al., 2015, *Arterioscler Thromb Vasc Biol* 35:409-420; Kofler et al., 2015, *Sci Rep* 5:16449).

The data herein show that targeting NOTCH3 signaling in mural cells is a useful therapeutic modality in SVD. To examine efficacy of treatment, a roster of morphological and biomarkers and retinal vascular leakage were leveraged.

Results and Discussion

Mural Cell Coverage in Vessels is Mechanistically Linked to Notch 3 Signaling

To investigate cell autonomous effects of Notch 3 signaling in mural cells, mural cell coverage was examined in retinal vessels from NOTCH3 knockout (N3KO) mice and N3KO mice conditionally expressing wild type (hN3WT) or CADASIL mutant (C455R) alleles of human Notch 3 in mural cells (FIG. 1A). Morphometric software separated main and branching vessel analyses, quantifying α-smooth muscle actin (SMA) coverage in both (FIG. 4). SMA staining was chosen to detect mural cells because expression of this marker is not impacted by changes in NOTCH3 activity (Arboleda-Velasquez et al., 2014, *Invest Ophthalmol Vis Sci* 55:5191-5199; Arboleda-Velasquez et al., 2008, *Proc Natl Acad Sci USA* 105:4856-4861). The retina has a very stereotypic vessel distribution and therefore offers unique advantages for quantitative assessments of changes in vascular structure. Moreover, there is clinical evidence for retinal changes in CADASIL patients (Robinson et al., 2001, *Surv Ophthalmol* 45:445-448; Rufa et al., 2011, *Cerebrovasc Dis* 31:77-82).

Figure 1B:
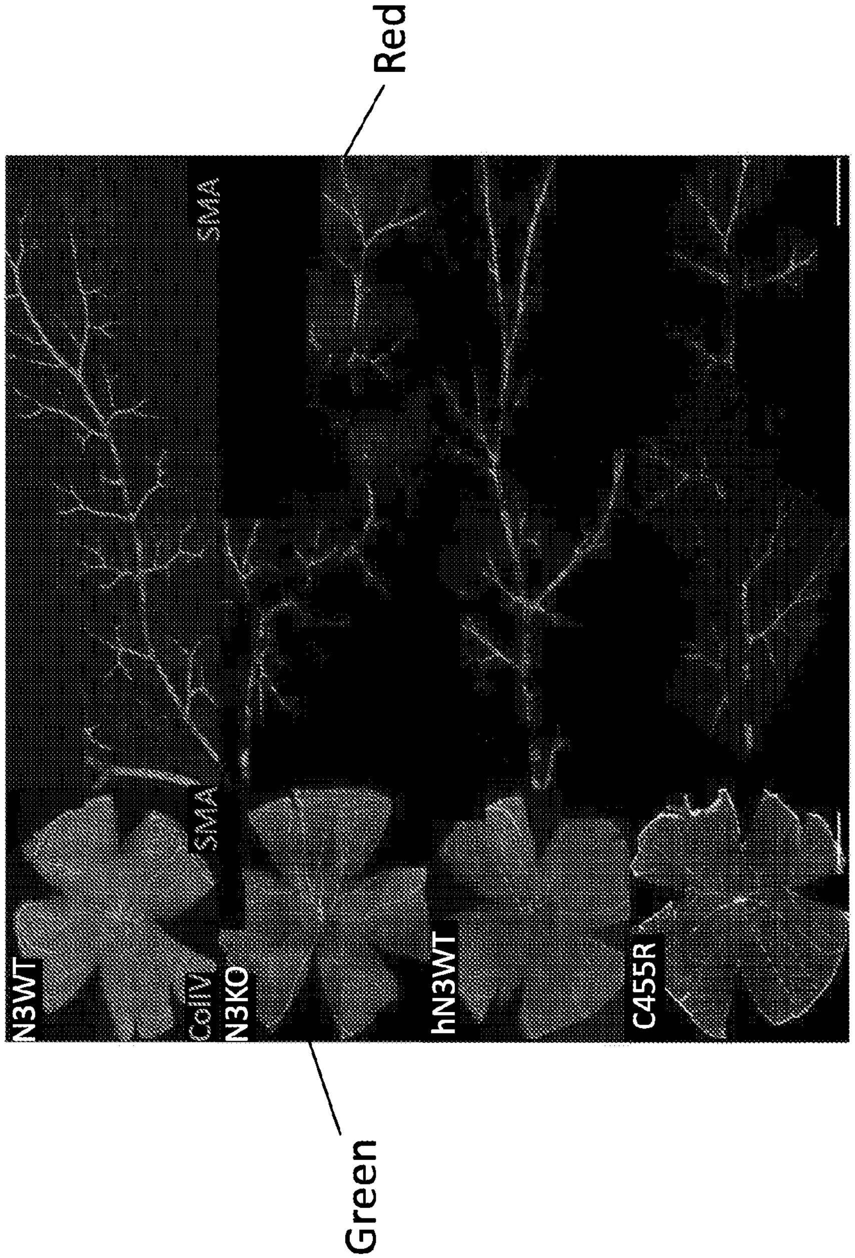
(FIG. 1B) Representative immunofluorescence images of retinal whole mounts showing SMA staining in red and collagen IV (ColIV) in green (left, scale bar=2.5 mm). Red dashed rectangles in left panels indicate regions displayed in center panels. (right, scale bar=250 μm) (FIG. 1C) Quantification of SMA coverage in main retinal arteries and branching arterioles. n=5 for each group, *$p<0.05$,**$p<0.01$, statistical analysis was done via ANOVA.
Figure 1C:
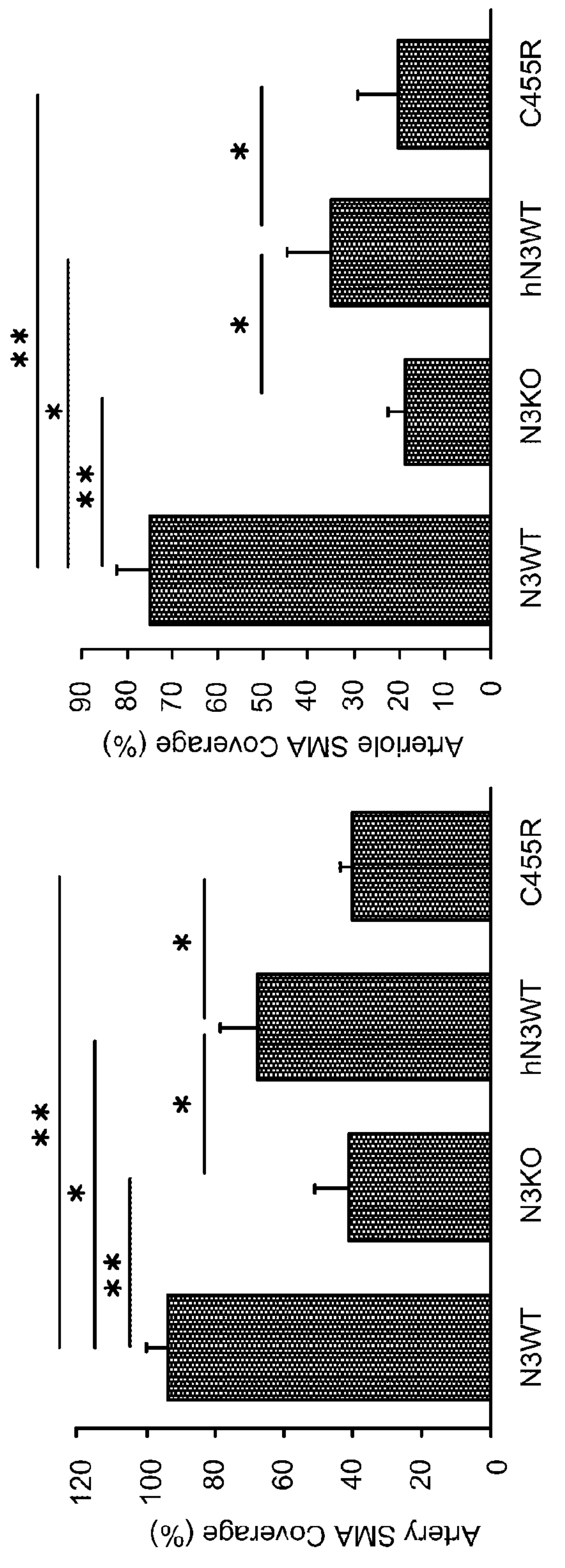
FIG. 1C is a set of graphs and FIGS. 1D, E, F, and G are images showing human Notch 3 rescue of mural cell loss in N3KO mice.
Figures 1D, 1E, 1F, 1G:
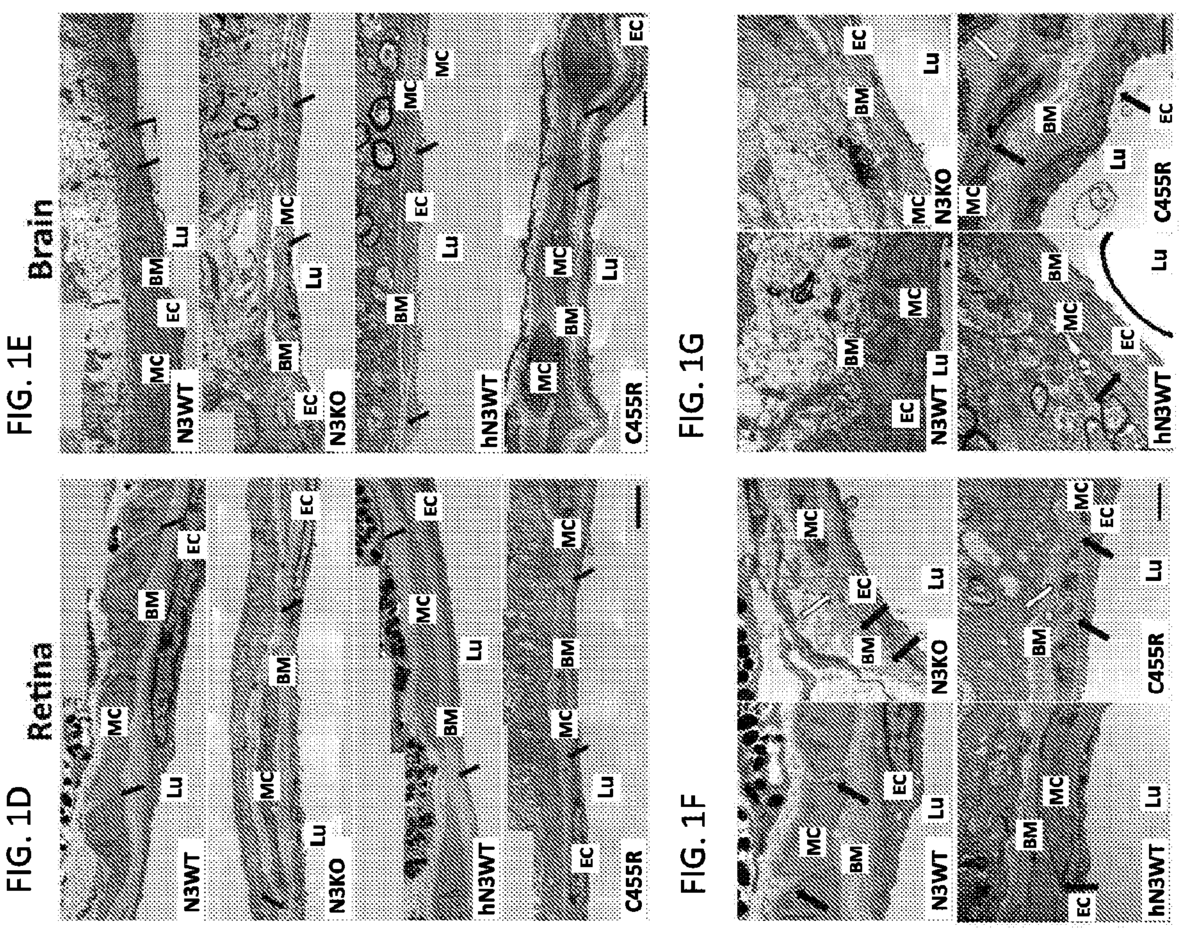
(FIG. 1D) Representative ultra structural images of retinal vessels (scale bar=200 μm) and cerebral vessels from the left hemisphere of the cerebral cortex cut at the bregma, (scale bar=2 μm) (FIG. 1E) obtained by transmission electron microscopy. Lumen (Lu), vascular endothelial cell (EC), basement membrane (BM), mural cell (MC), gaps in MC (black arrows) and apoptotic bodies (white arrows). Similarly, six features, listed above are highlighted on each image from retina (FIG. 1F) and brain (FIG. 1G). The N3WT mice exhibit large block-like MC that are in contact or are closely associated whereas the N3KO and C455R mice exhibit large gaps and elongated MCs. hN3WT exhibits elongated MCs juxtaposed to each other. Scale bar=1 μm.
Figure 2:
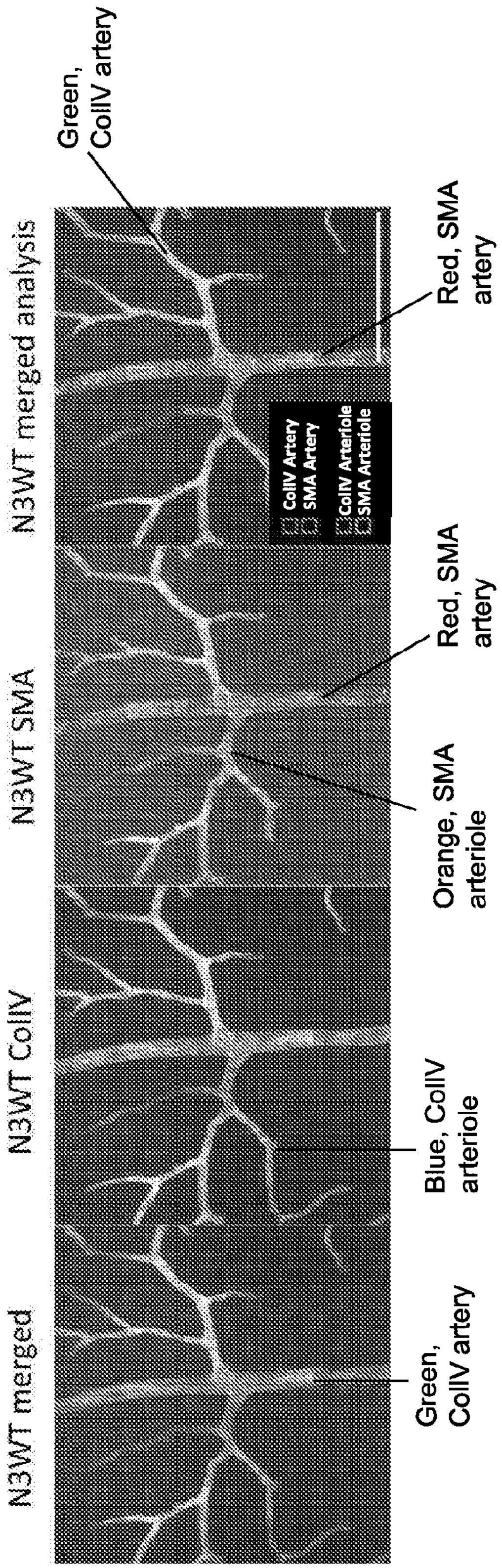
FIG. 2 is a set of images showing image processing of vessels via FIJI-based macro. Images of retinal whole mounts stained with collagen IV (Col IV) in green and smooth muscle actin (SMA) in red were processed. Seven images tracing a single vessel from optic nerve to periphery were stitched together using FIJI's MosaicJ macro. This was done for three vessels per retina/animal. The vascular analysis macro generates an outline of the vascularized area based on the Col IV silhouette, and is then cut up into small rectangles, each of which is identified as part of the main vessel, shown as green rectangles, or as part of branching vessels, shown as blue rectangles. The squares are then superimposed onto the red, SMA binary image and determined to have or not to have SMA staining. Rectangles containing a value of 0, having no SMA staining are qualified as gaps. The SMA positive areas are analyzed and qualified as main vessel coverage, shown as red outlined areas, or branching vessels, shown as orange outlined areas. The macro then saves parameters for each of the vessel types as an excel spreadsheet. Scale bar=200 μm.
Figure 3A:
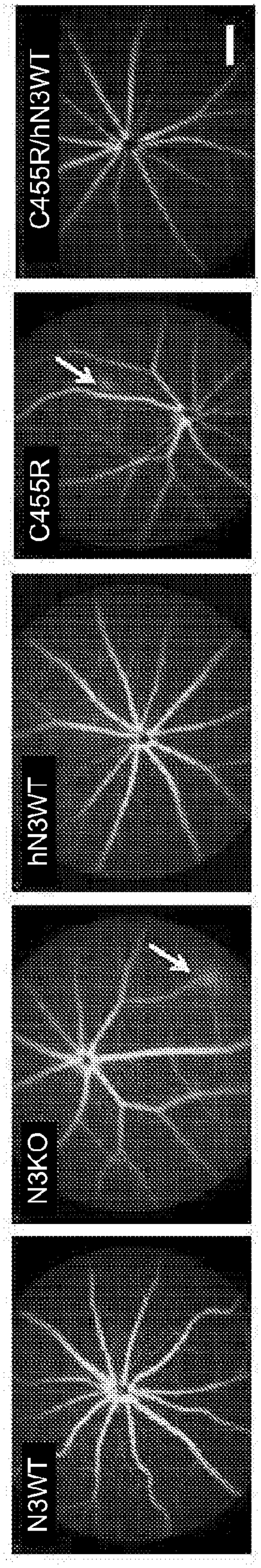
FIG. 3A are images of fluorescein angiography (FA) of the retina.
Figure 3B:
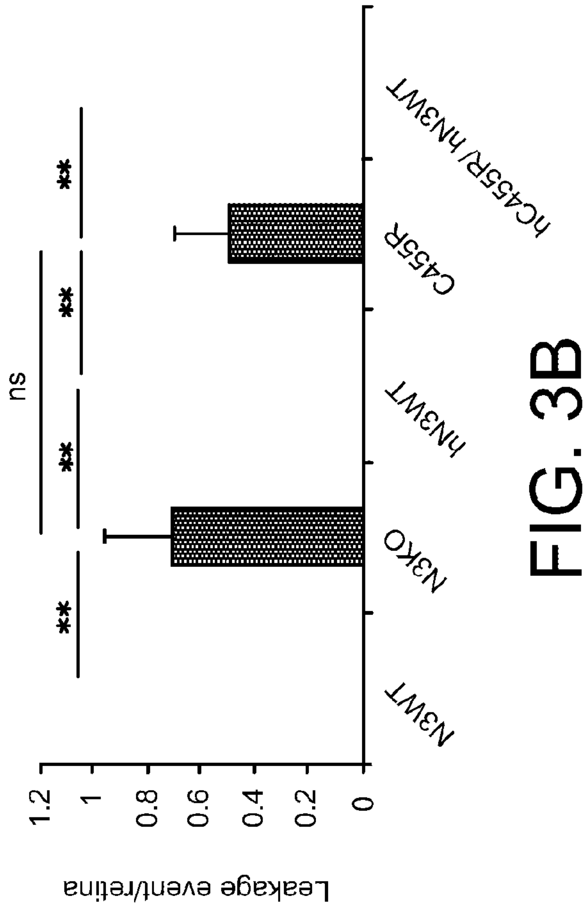
FIG. 3B is a graph relating to leakage events.

Absence of NOTCH3 expression was found to dramatically reduce mural cell coverage in retinal arteries and arterioles of six-month old animals (FIG. 1B, C). Furthermore, expression of hN3WT was sufficient to rescue mural cell loss in both large vessels and smaller caliber arteriole branches of N3KO mice (FIG. 1B, C). Indicative of a systemic phenotype, electron microscopy showed large gaps in mural cell coverage in vessels from the brain cortex and the retina in N3KO mice, whereas mural cells were juxtaposed to each other in knockout animals expressing human NOTCH3 in mural cells (FIG. 1D, E). Mural cells undergoing apoptosis were detected within the arterial gaps in N3KO animals (FIG. 1F, G). Altogether, these findings indicate that NOTCH3 signaling is both necessary and sufficient to support mural cell coverage in arteries and is indicative of a cell autonomous effect.

The impact of human NOTCH3 receptor with the C455R mutation was further investigated, because this mutation was identified in a family with early age at onset of CADASIL and can impair ligand-mediated Notch 3 signaling (Arboleda-Velasquez et al., 2002, *Neurology* 59:277-279; Arboleda-Velasquez et al., 2011, *Proc Natl Acad Sci USA* 108:E128-135). The C455R mutant did not rescue nor did it worsen mural cell loss in the N3KO animals (FIG. 1C). It was concluded that the C455R is a loss-of-function mutation and neomorphic effects, previously reported for CADASIL mutations, likely do not contribute to mural cell loss in this SVD model.

Additionally, genetic rescue of mural cell loss in N3KO mice by hN3WT supports the notion that patients with SVD due to reduced NOTCH3 signaling may benefit from therapeutic approaches leading to NOTCH3 signaling normalization.

Consistent with the morphological observations, wild type mice showed no evidence of vascular leakage in the retina using fluorescein angiography whereas Notch 3 knockout mice and Notch 3 knockout mice expressing the C455R CADASIL mutation in Notch 3 showed equally high number of leakage events in the retina. Expression of the human wild type Notch 3 was able to significantly reduce the frequency of leakage events in Notch 3 knockout animals and in Notch 3 knockout mice expressing the C455R CADASIL mutation.

Abbreviations

SVD: small vessel disease

NRR: negative regulatory region

SMA: α-smooth muscle actin

Materials and Methods

Statistical Analyses.

Pairwise comparisons were assessed using an unpaired two-tailed Student's t-test. One way ANOVA was used to compare more than two experimental groups. Results were considered significant for P<0.05. Analyses were performed and displayed using Prism software (GraphPad).

Animal Models.

All mouse models used in this study were previously described and were in a C57BL/6 (Arboleda-Velasquez et al., 2011, *Proc Natl Acad Sci USA* 108:E128-135; Arboleda-Velasquez et al., 2008, *Proc Natl Acad Sci USA* 105:4856-4861; Mitchell et al., 2001, *Nat Genet* 28:241-249). Both male and female littermates were included in the study. Briefly, mice are either wild type (N3WT), lacking endogenous mouse Notch 3 (N3KO), or express either a wild type human NOTCH3 transgene (hN3WT, MMRRC:032998 B6; 129 Gt(ROSA)26Sor$^{tm1(NOTCH3)Sat}$/Mmjax;) or a mutated human NOTCH3 transgene (C455R, MMRRC:033000 129-Gt(ROSA)26Sor$^{tm2(NOTCH3*C455R)Sat}$/Mmjax) in a N3KO background. Transgenes were inserted into the ROSA26 locus (Soriano, 1999, *Nat Genet* 21:70-71) and expression of this transgene occurs through Cre-mediated recombination under the smooth muscle cell promoter SM22 (Holtwick et al., 2002, *Proc Natl Acad Sci USA* 99:7142-7147). The hN3WT and C455R mouse models are available from the Jackson Laboratory under the auspices of the Mutant Mouse Regional Resource Centers program and National Institutes of Health (NIH).

Immunofluorescence.

Eyes were harvested and fixed in 4% paraformaldehyde overnight at 4° C. The eyes were then washed three times in phosphate buffered saline (Sigma, D5652-10×1 L), at which point retinas were dissected out of each eye and washed as described above. Retinas were then placed in borosilicate glass vials (VWR, 16218-126) and 300 μl of blocking buffer for 6 hrs. Blocking buffer was prepared as previously described (Primo et al., 2016, *Brain Res* 1644:118-126). Retinas were washed again as above, and double stained with primary antibodies against; goat anti-mouse, smooth muscle actin (Novus, NB300-978) at 1:100 concentration and rabbit anti-mouse collagen IV (Abcam, ab6586) in blocking buffer overnight at 4° C. on a rocker. Retinas were then washed as described above, and immersed for four h at room temperature in secondary antibodies; Donkey Anti-Goat IgG H&L (Cy3®) preadsorbed (Abcam, ab6949), Donkey Anti-Rabbit IgG H&L (Alexa Fluor® 488) (Abcam, ab150073), all at a 1:100 concentration in blocking buffer. Retinas were then washed as described above and whole mounted on glass slides, (Azer Scientific, EMSC200L), coated with 50% Glycerol in PBS under a rectangular cover slip (Fisher Scientific, 12-545-F) and sealed with nail polish (REVLON, 8435-76). Entire retinas were imaged at 5×1.25 magnification and three vessels from each retina were imaged at 20×1.25 magnification with an Axioscope 2 Mot Plus (Zeiss).

Electron Microscopy (EM).

Tissue was fixed in 2.5% glutaraldehyde and 2% paraformaldehyde (PFA) in 0.1 M sodium cacodylate buffer (pH 7.4), rinsed, dehydrated in a series of ethanol dilutions (50-100%), and embedded in epoxy resin (Embed 812; Electron Microscopy Sciences). Ultrathin sections (60 nm) were cut on a Reichert ultramicrotome and collected on Formvar- and carboncoated grids. Samples were stained with 2% uranyl acetate and lead citrate and examined on a Philips Tecnai 12 BioTWIN electron microscope. Images were captured digitally using a CCD camera (Morada; Soft Imaging Systems).

Fluorescein Angiography.

A Micron III (Phoenix Research) system was used to take fundus photographs in anesthetized mice according to manufacturers instructions. The animals' pupils were dilated using a drop of 1% Tropicamide followed by a drop of 1% cyclopentolate hydrochloride applied on the corneal surface. Eyes were kept moist with ocular lubricant (Genteal). The mice were placed in front of the Fundus camera and pictures of the retina taken. FA was performed after intraperitoneal injection of 0.05 ml of 25% fluorescein sodium (Akron, pharmaceutical grade). Photographs were taken with a pre-set 20D lens appositioned to the camera lens at regular time (from 1 min to 4 min post IP injection). Fluorescein leakage was noted as diffuse opacity in the vitreous over-time.

OTHER EMBODIMENTS

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. Genbank and NCBI submissions indicated by accession number cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method for treating a small vessel disease (SVD) in a subject, comprising administering to the subject an effective amount of a Neurogenic Locus Notch Homolog Protein 3 (NOTCH3) agonist polypeptide comprising a polypeptide comprising the extracellular domain of DELTA-LIKE4 (SEQ ID NO: 23) or a fragment thereof comprising a stretch of amino acids having the sequence CSDNYYGDNCSRLCKKR (SEQ ID NO:8).

2. The method of claim 1, wherein the SVD is cerebral SVD.

3. The method of claim 2, wherein the cerebral SVD is cerebral autosomal-dominant arteriopathy with subcortical infarcts and leukoencephalopathy (CADASIL), or cerebral autosomal recessive arteriopathy with subcortical infarcts and leukoencephalopathy (CARASIL).

4. The method of claim 1, wherein the subject has a loss-of-function mutation in NOTCH3.

5. The method of claim 1, wherein the subject has diabetic retinopathy, age-related macular degeneration (AMD), nephropathy, microangiopathy, heart failure, Alagille syndrome, familial tetralogy of Fallot, patent ductus arteriosus, or a cerebral cavernous malformation.

6. The method of claim 1, wherein the subject comprises a level of collagen18α1, endostatin, NOTCH3, N3ECD, IGFBP-1, HTRA1, and/or NF-L protein or mRNA that is different than a normal control.

7. The method of claim 1, wherein the extracellular domain of DELTA-LIKE4 or fragment thereof comprises a stretch of amino acids having the sequence CSDNYYGDNCSRLCKKRNDHFGH (SEQ ID NO:9).

8. The method of claim 7, wherein the SVD is cerebral SVD.

9. The method of claim 8, wherein the cerebral SVD is cerebral autosomal-dominant arteriopathy with subcortical infarcts and leukoencephalopathy (CADASIL), or cerebral autosomal recessive arteriopathy with subcortical infarcts and leukoencephalopathy (CARASIL).

10. The method of claim 1, wherein the agonist polypeptide consists of CSDNYYGDNCSRLCKKR (SEQ ID NO:8).

11. The method of claim 10, wherein the SVD is cerebral SVD.

12. The method of claim 11, wherein the cerebral SVD is cerebral autosomal-dominant arteriopathy with subcortical infarcts and leukoencephalopathy (CADASIL), or cerebral autosomal recessive arteriopathy with subcortical infarcts and leukoencephalopathy (CARASIL).

13. The method of claim 1, wherein the agonist polypeptide consists of CSDNYYGDNCSRLCKKRNDHFGH (SEQ ID NO:9).

14. The method of claim 13, wherein the SVD is cerebral SVD.

15. The method of claim 14, wherein the cerebral SVD is cerebral autosomal-dominant arteriopathy with subcortical infarcts and leukoencephalopathy (CADASIL), or cerebral autosomal recessive arteriopathy with subcortical infarcts and leukoencephalopathy (CARASIL).

* * * * *